US008431121B2

(12) United States Patent
Davis et al.

(10) Patent No.: US 8,431,121 B2
(45) Date of Patent: Apr. 30, 2013

(54) SPECIFICALLY TARGETED CATALYTIC ANTAGONISTS AND USES THEREOF

(75) Inventors: Benjamin G. Davis, Durham (GB); John Bryan Jones, Lakefield (CA); Richard R. Bott, Burlingame, CA (US); Karl John Sanford, Cupertino, CA (US); David Aaron Estell, San Mateo, CA (US)

(73) Assignees: Danisco US Inc., Palo Alto, CA (US); Governing Council of the University of Toronto (CA)

( * ) Notice: Subject to any disclaimer, the term of this patent is extended or adjusted under 35 U.S.C. 154(b) by 0 days.

(21) Appl. No.: 12/953,378

(22) Filed: Nov. 23, 2010

(65) Prior Publication Data

US 2011/0262419 A1    Oct. 27, 2011

Related U.S. Application Data

(63) Continuation of application No. 10/791,628, filed on Mar. 1, 2004, now abandoned, which is a continuation of application No. 09/556,466, filed on Apr. 21, 2000, now abandoned.

(60) Provisional application No. 60/131,362, filed on Apr. 28, 1999.

(51) Int. Cl.
*A61K 38/48* (2006.01)

(52) U.S. Cl.
USPC ........................................................ 424/94.3

(58) Field of Classification Search ........................ None
See application file for complete search history.

(56) References Cited

U.S. PATENT DOCUMENTS

| 5,208,158 A | 5/1993 | Bech et al. |
|---|---|---|
| 5,244,791 A | 9/1993 | Estell |
| 5,316,935 A | 5/1994 | Arnold et al. |
| 5,316,941 A | 5/1994 | Estell et al. |
| 5,403,737 A | 4/1995 | Abrahmsen et al. |
| 5,436,150 A | 7/1995 | Chandrasegaran |
| 5,629,173 A | 5/1997 | Abrahmsen et al. |
| 5,955,340 A | 9/1999 | Bott |
| 6,159,447 A * | 12/2000 | Budny et al. ............... 424/49 |

FOREIGN PATENT DOCUMENTS

| EP | 3 328 229 A1 | 8/1989 |
|---|---|---|
| WO | WO 91/16423 | 4/1991 |
| WO | WO 94/15644 | 7/1994 |
| WO | WO 96/27671 | 2/1996 |
| WO | WO 97/37007 | 10/1997 |
| WO | WO 98/23732 | 6/1998 |

OTHER PUBLICATIONS

Abrahmsen et al., "Engineering Subtilisin and Its Subtrates for Efficient Ligation of Peptide Bonds in Aqueous Solution," *Biochemistry*, 30:4151-59 (1991).

Akabas et al., "Acetylcholine Receptor Channel Structure Probed in Cysteine-Substitution Mutants," *Science*, 258:307-310 (1992).

Alvear et al., "Inactivation of Chicken Liver Mevalonate 5-Diphosphate Decarboxylase by Sulfhydryl-Directed Reagents: Evidence of a Functional Dithiol," *Biochimica et Biophysica Acta*, 994:7-11 (1998).

Barbas et al., "A Search for Peptide Ligase: Cosolvent-Mediated Conversion of Proteases to Esterases for Irreversible Synthesis of Peptides," *J. Am. Chem. Soc.*, 110:5162-66 (1988).

Barbas, et al., "Papain Catalysed Peptide Synthesis: Control of Amidase Activity and the Introduction of Unusual Amino Acids," *J. Chem. Soc., Chem. Commun.*, 533-34 (1987).

Bech et al., "Significance of Hydrophobic $S_4$-$P_4$ Interactions in Subtilisin, 309 from *Bacillus lentus*," *Biochemistry*, 32:2847-2852 (1993).

Bell et al., "Kinetic Studies on the Peroxidase Activity of Selenosubtilisin," *Biochemistry*, 32:3754-3762 (1993).

Berglund et al., "Altering the Specificity of Subtilisin *B. Lentus* by Combining Site-Directed Mutagenesis and Chemical Modification," *Bioorganic & Mechanical Chemistry* Letters 6:2507-2512 (1996).

Berglund et al., "Chemical Modification of Cysteine Mutants of Subtilisin *Bacillus lentus* Can Create Better Catalysts Than The Wild-Type Enzyme," *J. Am. Chem. Soc.*, 119:5265-5266 (1997).

Betzel et al., "Crystal Structure of the Alkaline Proteinase Savinase™ from *Bacillus lentus* at 1 4 Å Resolution," *J. Mol. Biol.*, 223:427-445(1992).

Bodwell et al., "Sulfhydryl-Modifying Reagents Reversibly Inhibit Binding of Glucocorticoid-Receptor Complexes to DNA-Cellulos," *Biochemistry*, 23:1392-1398 (1984).

Bonneau et al., "Alteration of the Specificity of Subtilisin BPN' by Site-Directed Mutagenesis in its $S_1$ and $S_1$' Binding Sites," *J. Am. Chem. Soc.*, 113:1026-30 (1991).

Brocklehurst, "Specific Covalent Modification of Thiols: Applications in the Study of Enzymes and Other Biomolecules," *Int. J. Biochem.*, 10:259-274 (1979).

Bruice et al., "Novel Alkyl Alkanethiolsulfonate Sulfhydryl Reagents. Modification of Derivatives of L-Cysteine," *Journal of Protein Chemistry*, 1:47-58 (1982).

Buckwalter et al., "Improvement in the Solution Stability of Porcine Somatotropin by Chemical Modification of Cysteine Residues," *J. Agric. Food Chem.*, 40:356-362 (1992).

(Continued)

*Primary Examiner* — Tekchand Saidha
*Assistant Examiner* — Younus Meah
(74) *Attorney, Agent, or Firm* — Danisco US Inc.

(57) ABSTRACT

This invention provides chimeric molecules that are catalytic antagonists of a target molecule. The catalytic antagonists of this invention preferably comprise a targeting moiety attached to an enzyme that degrades the molecule specifically bound by the targeting moiety. The catalytic antagonists of this invention thus bind to a target recognized by the targeting moiety (e.g., a receptor) the enzyme component of the chimera then degrades all or part of the target. This typically results in a reduction or loss of activity of the target and release of the chimeric molecule. The chimeric molecule is then free to attack and degrade another target molecule.

13 Claims, 13 Drawing Sheets

OTHER PUBLICATIONS

Chen et al., "Incorporation of Unnatural Amino Acid Derivatives into a Peptide Bond via an Oxime Ester Catalysed by Papain or Lipase," *Chem. Commun.*, 165-66 (1996).

Chen et al., "Kinetically Controlled Peptide Bond Formation in Anhydrous Alcohol Catalyzed by the Industrial Protease Alcalase," *J. Org. Chem.*, 57:6960-65 (1992).

Chen et al., "Probing the S-1' Subsite Selectivity of an Industrial Alkaline Protease in Anhydrous t-Butanol," *Bioorganic & Medicinal Chemistry Letters*, 3(4):727-33 (1993).

Daly et al., "Formation of Mixed Disulfide Adducts at Cysteine-281 of the Lactose Repressor Protein Affects Operator and Inducer Binding Parameters," *Biochemistry*, 25:5468-5474 (1986).

Davies et al., "A Semisynthetic Metalloenzyme Based on a Protein Cavity That Catalyzes the Enantiosleective Hydrolysis of Ester and Amide Substrates," *J. Am. Chem. Soc.*, 119:11643-11652 (1997).

Davis, B.G., et al., "Glycosyldisulfides: a new class of solution and solid phase glycosyl donors," Chem. Commun, 2001, pp. 189-190.

Davis, Benjamin G, et al., "The Controlled Glycosylation of a Protein with a Bivalent Glycan: Towards a New Class of Glycoconjuates, Glycodendriproteins," *Chem. Commun.*, 2001 pp. 351-352.

DeSantis et al., "Chemical Modifications at a Single Site Can Induce Significant Shifts in the pH Profiles of a Serine Protease," *J. Am Chem. Soc.*, 120:8582-8586 (1998).

DeSantis, et al., "Probing the altered specificity and catalytic properties of mutant usbtilisin chemically modified at position S156C and S166C in the S1 pocket," Bioorganic and Medicinalehcmistry, 7:7 pp. 1381-1387 (1999).

Di Bello, "Total Synthesis of Proteins by Chemical Methods: The Horse Heart Cytochrome C Example," *Gazzetta Chimica Italiana*, 126:189-197 (1996).

Dickman, M., et al., "Chemically modified mutants subtilisin *Bacillus lentus* catalyze transesterification reactions better than wild type," *Tetrahedron Asymmetry*, (Dec. 11, 1998) 9/23 4099-4102, XPO000901276.

Dime, DS., "Protein Topology and Ion Channel Research," Toronto Research Chemicals, Inc. (catalog date unknown).

Ekberg et al., "Enzymatic Coupling of Two D-Amino Acid Residues in Aqueous Media," *Tetrahedron Letters*, 30(5):583-86 (1989).

Engler et al., "Critical Functional Requirement for the Guanidinium Group of the Arginine 41 Side Chain of Human Epidermal Growth Factor as Revealed by Mutagenic Inactivation and Chemical Reactivation," The Journal of Biological Chemistry, 1992.

Frillingos et al., "Cysteine-Scanning Mutagenesis of Helix II and Flanking Hydrophilic Domains in the Lactose Permease of *Escherichia coli*," *Biochemistry*, 36:269-273 (1997).

Gloss et al., "Examining the Structural and Chemical Flexibility of the Active Site Base, Lys-258, of *Escherichia coli* Aspartate Aminotransferase by Replacement with Unnatural Amino Acids" Biochemistry, 34:12323-12322 (1995).

Graycar et al., "Altering the Proteolytic Activity of Subtilisin through Protein Engineering," *Annals New York Academy of Science*, 672:71-79 (1992).

Gron et al., "A Highly Active and Oxidation-Resistant Subtilisin-Like Enzyme Produced by a Combination of Site-Directed Mutagenesis and Chemical Modification," *Eur. J. Biochem.*, 194:897-901(1990).

Gron et al., "Extensive Comparison of the Substrate Preferences of Two Subtilisins As Determined with Peptide Substrates Which Are Based on the Principle of Intramolecular Quenching." Biochemistry, 31(26):6011-18 (1992).

Hempel et al., "Selective Chemical Modification of Human Liver Aldehyde Dehydrogenases $E_1$ and $E_2$ by Iodoacetamide," *The Journal of Biological Chemistry*, 256:10889-10896 (1981).

Hilvert et al., "A Highly Active Thermophilic Semisynthietic Flavoenzyme," *J. Am. Chem. Soc.*, 110:682-689 (1988).

Hilvert et al., "New Semisynthetic Flavoenzyme Based on a Tetrameric Portein Template, Glyceraldehyde-3-Phosphate Dehydrogenase," *J. Am. Chem. Soc.*, 107:5805-5806 (1985).

House et al., "¹H NMR Spectroscopic Studies of Selenosubtilisin," *Biochemistry*, 32:3468-3473 (1993).

Huang et al., "Improving the Activity of Immobilized Subtilisin by Site-Specific Attachment to Surfaces," *Anal. Chem.*, 69:4601-4607 (1997).

Jonsson et al., "Temperature Effects on Protease Catalyzed Acyl Transfer Reactions in Organic Media," *Journal of Molecular Catalysis B: Enzymatic*, 2:43-51 (1996).

Kaiser, "Catalytic Activity of Enzymes Altered at Their Active Sites," *Agnew. Chem. Int. Ed. Engl.*, 27-913-922 (1988).

Kanaya et al., "Role of Cysteine Residues in Ribonuclease H from *Escherichia coli*," *Biochem. J.*, 271:59-66 (1990).

Kato et al., "First Stereoselective Synthesis of D-Amino Acid N-Alkyl Amide Catalyzed by D-Aminopeptidase," *Tetrahedron*, 45(18) 5743-54 (1989).

Kawase et al., "Effect of Chemical Modification of Tyrosine Residues on Activities of Bacterial Lipase," *Journal of Fermentation and Bioengineering*, 72:317-319 (1991).

Kawashiro et al., "Effect of Ester Moiety of Substrates on Enantioselectivity of Protease Catalysis in Organic Media," *Biotechnology Letters*, 18(12):1381-86 (1996).

Kenyon et al., "Novel Sulfhydryl Reagents," *Methods Enzymol.*, 47:407-430 (1977).

Kirley, "Reduction and Fluorescent Labeling of Cyst(e)ine-Containing Proteins for Subsequent Structural Analyses," *Analystical Biochemistry*, 180:231-236 (1989).

Kluger et al., "Amino Group Reactions of the Sulfhydryl Reagent Methyl Methanesulfonothioate. Inactivation of D-3-hydroxybutyrate Dehydrogenase and Reaction with Amines in Water." *Can. J. Biochem.*, 58:629-622 (1980).

Kokubo et al., "Flavohemoglobin: A Semisynthetic Hydroxylase Acting in the Absence of Reductase," *J. Am. Chem. Soc.*, 109:606-607 (1987).

Konigsberg, "Reduction of Disulfide Bonds in Proteins with Dithiothreitol," *Methods in Enzymology*, 25:185-188 (1972).

Kuang et al., "Enantioselective Reductive Amination of α-Amino Acids by a Pyridoxamine Cofactor in a Protein Cavity," *J. Am. Chem. Soc.*, 118:10702-10706.

Lewis et al., "Determination of Interactive Thiol Ionizations in Bovine Serum Albumin, Glutathione, and Other Thiols by Potentiometric Difference Titration," *Biochemistry*, 19:6129-6137 (1980).

Liu et al., "Site-Directed Fluorescence Labeling of P-Glycoprotein on Cysteine Residues in the Nucleotide Binding Domains," *Biochemistry*, 35:11865-11873 (1996).

Margolin et al., "Incorporation of D-Amino Acids into Peptides via-Enzymatic Condensation in Organic Solvents," *J. Am. Chem. Soc.*, 109:7885-87 (1987).

Margolin et al., "Peptide Synthesis Catalyzed by Lipases in Anhydrous Organic Solvents," *J. Am. Chem. Soc.*, 109:3802-04 (1987).

Miller et al., "Peroxide Modification of Monoalkylated Glutathione Reductase," *The Journal of Biological Chemistry*, 266:19342-19360 (1991).

Morea et al., "Exploitation of Subtilisin BPN as Catalyst for the Synthesis of Peptides Containing Noncoded Amino Acids, Peptide Mimetics and Peptides Conjugates," *J. Am. Chem. Soc.*, 119:3942-47 (1997).

Morihara et al., "α-Chymotrypsin as the Catalyst for Peptide Synthesis," *Biochem. J.*, 163:531-42 (1977).

Nakatsuka et al., "Peptide Segment Coupling Catalyzed by the Semisynthetic Enzyme Thiolsubtilisin," *J. Am. Chem. Soc.*, 109:3808-10 (1987).

Nakayama et al., "Chemical Modification of Cysteinyl, Lysyl and Histidyl Residues of Mouse Liver 17β-Hydroxysteroid Dehydrogenase," *Biochimica et Biophysica Acta*, 1120:144-150 (1992).

Neet, K.E. and Koshland, D.E., "The Conversion of Serine at the Active Site of Subtilisin to Cysteine: A 'Chemical Mutation,'" *Proc. Nat. Acad. Sci. USA*, 56(5):1606-1611 (1966).

Nishimura et al., "Reversible Modification of the Sulfhydryl Groups of *Escherichia coli* Succinic Thiokinase with Methanethiolating Reagents, 5,5'-Dithio-bis(2-Nitrobenzoic Acid), p-Hydroxymercuribenzoate, and Ethylmercurithiosalicylate," Archives of, 1975.

O'Connor et al., "Probing an Acyl Enzyme of Selenosubtilisin by Raman Spectroscopy," *J. Am. Chem. Soc.*, 118:239-240 (1996).

Pardo et al., "Cysteine 532 and Cystein 545 Are the N-Ethylmaleimide-Reactive Residues of the *Neurospora* Plasma Membrane H+-ATPase," *The Journal of Biological Chemistry*, 264:9373-9379 (1989).

Peterson et al., "Nonessential Active Site Residues Modulate Selenosubtilisin's Kinetic Mechanism," *Biochemistry*, 34:6616-6620 (1995).

Peterson et al., "Selenosubtilisins Peroxidase Activity Does Not Require an Intact Oxyanion Hole," *Tetrahedron*, 53:12311-12317 (1997).

Planas et al., "Reengineering the Catalytic Lysine of Aspartate Aminotransferase by Chemical Elaboration of a Genetically Introduced Cysteine," *Biochemistry*, 30:8268-8276 (1991).

Plettner, E., et al., "Modulation of Esterase and Amidase Activity of Subtilisin Bacillus lentus by Chemical Modification of Cysteine Mutants," *Journal of the American Chemical Society*, (Jun. 2, 1999) 121/21 4977-4981, XPO000891274.

Plettner, Erika et al., "A Combination Approach to Chemical Modification of Subtilisin *Bacillus lentus*," *Bioorganic & Medicinal Chemistry Letters* (Sep. 8, 1998) vol. 8, No. 17, pp. 2291-2296, XP0004138220.

Polgar et al., "A New Enzyme Containing a Synthetically Formed Active Site. Thiol-Subtilisin," *Journal of American Chemical Society*, 88:3153-3154 (1966).

Polgar, "Spectrophotometric Determination of Mercaptide Ion, an Activated Form of SH-Group in Thiol Enzymes," *FEBS Letters*, 38:187-190 (1974).

Presenting Our Line of MTS Compounds, Toronto Research Chemicals Inc. (catalog, date unknown).

Radziejewski et al., "Catalysis of N-Alkyl-1,4-Dihydronicotinamide Oxidation by a Flavopapain: Rapid Reaction in All Catalytic Steps," *J. Am. Chem. Soc.*, 107:3352-3354 (1985).

Raja et al., "Activation of *Sulfolobus solfataricus* Alcohol Dehydrogenase by Modification of Cysteine Residue 38 with Iodoacetic Acid," *Biochemistry*, 35:638-647 (1996).

Ramachandran et al., "Stabilization of Barstar by Chemical Modification of the Buried Cysteines," *Biochemistry*, 35:8776-8785 (1996).

Roberts et al., "Reactivity of Small Thliolate Anions and Cysteine-25 in Papain Toward Methyl Methanethiosulfonate," *Biochemistry*, 25:5595-5601 (1986).

Rokita et al., "Synthesis and Characterization of a New Semisynthetic Enzyme, Flavolysozyme," *J. Am. Chem. Soc.*, 108:4984-4987 (1986).

Sears et al., "Engineering Enzymes for Bioorganic Synthesis. Peptide Bond Formation," *Biotechnolo. Prog.*, 12:423-33 (1996).

Sears et al., "Engineering Subtilisin for Peptide Coupling: Studies on the Effects of Counterions and Site-Specific Modifications on the Stability and Specificity of the Enzyme" *J. Am. Chem. Soc.*, 116:6521-30 (1994).

Siddiqui et al, "Arthrobacter D-Xylose Isomerase: Chemical Modification of Carboxy Groups and Protein Engineering of pH Optimum," *Biochem. J.*, 295:685-691 (1993).

Smith et al., "An Engineered Change in Substrate Specificity of Ribulosebisphosphate Carboxylase/Oxygenase," *The Journal of Biological Chemistry*, 265:1243-1245 (1990).

Smith et al., "Chemical Modification of Active Site Residues in γ-Glutamyl Transpeptidase," *The Journal of Biological Chemistry*, 270:12476-12480 (1995).

Smith et al., "Nonessentiality of the Active Sulfhydryl Group of Rabbit Muscle Creatine Kinase," *The Journal of Biological Chemistry*, 249:3317-3318 (1974).

Smith et al., "Restoration of Activity to Catalytically Deficient Mutants of Ribulosebisphosphate Carboxylase/Oxygenase by Aminoethylation," *The Journal of Biological Chemistry.*, 263:4921-4925 (1988).

Smith et al., "Simple Alkanethiol Groups for Temporary Blocking of Sulfhydryl Groups of Enzymes," *Biochemistry*, 14:766-771 (1975).

Smith et al., "Subtle Alteration of the Active Site of Ribulose Bisphosphate Carboxylase/Oxygenase by Concerted Site-Directed Mutagenesis and Chemical Modification. " *Biochemical and Biophysical Research Communications*, 1988.

So et al., "Lipase-Catalyzed Synthesis of Peptides Containing D-Amino Acid," *Enzyme Microb. Technol.*, 23:211-15 (1998).

Soper et al., "Effects of Substrates on the Selectie Modification of the Cysteinyl Residues of D-Aminio Acid Transaminase," *The Journal of Biological Chemistry*, 254:10901-10905 (1979).

Spura, A., et al., "Probing the Agonist Domain of the Nicotinic Acetylcholine Receptor by Cysteine Scanning Mutagenesis Reveals Residues in Proximity to the alpha-Bungarotoxin Binding Site," *Biochemistry* 38:16, pp. 4912-4921 (Apr. 20, 1999).

Stauffer et al., "Electrostatic Potential of the Acetylcholine Binding sites in the Nicotinic Receptor Probed by Reactions of Binding-Site Cysteines with Charged Methanethiosulfonates" *Biochemistry.* 33:6840-6849 (1994).

Stepanov, "Proteinases as Catalysts in Peptide Synthesis," *Pure & Appl. Chem.*, 68(6):1335-39 (1996).

Stewart et al., "Catalytic Oxidation of Dithiols by a Semisynthetic Enzyme," *J. Am. Chem. Soc.*, 108:3480-3483 (1986).

Suckling et al., "Carbon-Carbon Bond Formation Mediated by Papain Chemically Modified by Thiazolium Salts," *Bioorganic & Medicinal Chemistry Letters*, 3:531-534 (1993).

Svensson et al., "Mapping the Folding Intermediate of Human Carbonic Anhydrase II. Probing Substructure by Chemical Reactivity and Spin and Fluorescence Labelling of Engineered Cysteine Residues." *Biochemistry*, 34:8606-8620 (1995).

Valenzuela et al., "Kinetic Properties of Succinylated and Ethylenediamine-Amidated δ-Chymotrypsins," *Biochim. Biophys. Acta*, 250:538-548 (1971).

Wang et al., "Enzymes in Organic Synthesis: use of Subtilisin and a Highly Stable Mutant Derived from Ultiple Site-Specific Mutations," *J. Am. Chem. Soc.*, 112:945-53 (1990).

Watanabe, et al., "A Unique Enzyme from *Saccharothrix* sp. Catalyzing D-Amino Acid Transfer," *Biochimica et Biophysica Acta*, 1337:40-46 (1997).

West et al., Enzyme-catalysed Synthesis of Peptides Containing D-Amino Acids, *J. Chem. Soc. Chem. Commun.*, pp. 417-418 (1986).

West et al., "Enzyme-Catalyzed Irreversible Formation of Peptides Containing D-Amino Acids," *J. Org. Chem.*, 51:2728-35 (1986).

West et al., "Enzymes as Synthetic Catalysts: Mechanistic and Active-Site Considerations of Natural and Modified Chymotrypsin," *J. Am. Chem. Soc.*, 112:5313-5320 (1990).

West et al., "Modification of Proteases to Esterases for Peptide Synthesis: Methylchymotrypsin," *J. Am. Chem. Soc.*, 110:3709-10 (1988).

White et al., "Sequential Site-Directed Mutagenesis and Chemical Modification to Convert the Active Site Arginine 292 of Aspartate Aminotransferase to Homoarginine," *Journal of the American Chemical Society*, 114:292-293 (1992).

Worku et al., "Identification of Histidyl and Cysteinyl Residues Essential for Catalysis of 5'-Nucleotidase," *FEBS Letter*, 167:235-240 (1984).

Wu et al., "Conversion of a Protease into an Acyl Transferase: Selenolsubtilisin," *J. Am. Chem. Soc.*, 111:4514-4515 (1989).

Wynn et al., "Chemical Modification of Protein Thiols: Formation of Mixed Disulfides," *Methods in Enzymology*, 251:351-356 (1995).

Wynn et al., "Comparison of Straight Chain and Cyclic Unnatural Almino Acids Embedded in the Core of Staphylococcal Nuclease," *Protein Science*, 6:1621-1626 (1997).

Wynn et al., "Mobile Unnatural Amino Acid Side Chains in the Core of Staphylococcal Nuclease," *Protein Science*, 5:1026-1031 (1996).

Wynn et al., "Unnatural Amino Acid Packing Mutants of *Escherichia Coli* Thioredoxin Produced by Combined Mutagenesis/Chemical Modification Techniques," *Protein Science* 2:395-403 (1993).

Xu et al., "Amino Acids Lining the Channel of the γ-Am inobutyric Acid Type A Receptor Identified by Cysteine Substitution," *The Journal of Biological Chemistry*, 268:21505-21508 (1993).

Zhang et al., Protease-catalyzed Small Peptide Synthesis in Organic Media, *Enzyme Microb. Technol.*, 19:538-44 (1996).

Davis et al., J. Org. Chem. 63(26) pp. 9614-9615 (1998).

Nilsson et al., Glycoconjugate J 4, pp. 219-223 (1987).

Ofran et al., Drug Discov. Today 10, pp. 1475-1482 (2005).

Wang et al., JBC 250, pp. 1490-1502 (1975).

Bayer, E.A, et al., "Affinity Cleavage and Targeted Catalysis of Proteins Using the Avidin-Biotin System." *Biochemistry* 29: 11274-11279 (1990).

* cited by examiner

Type A
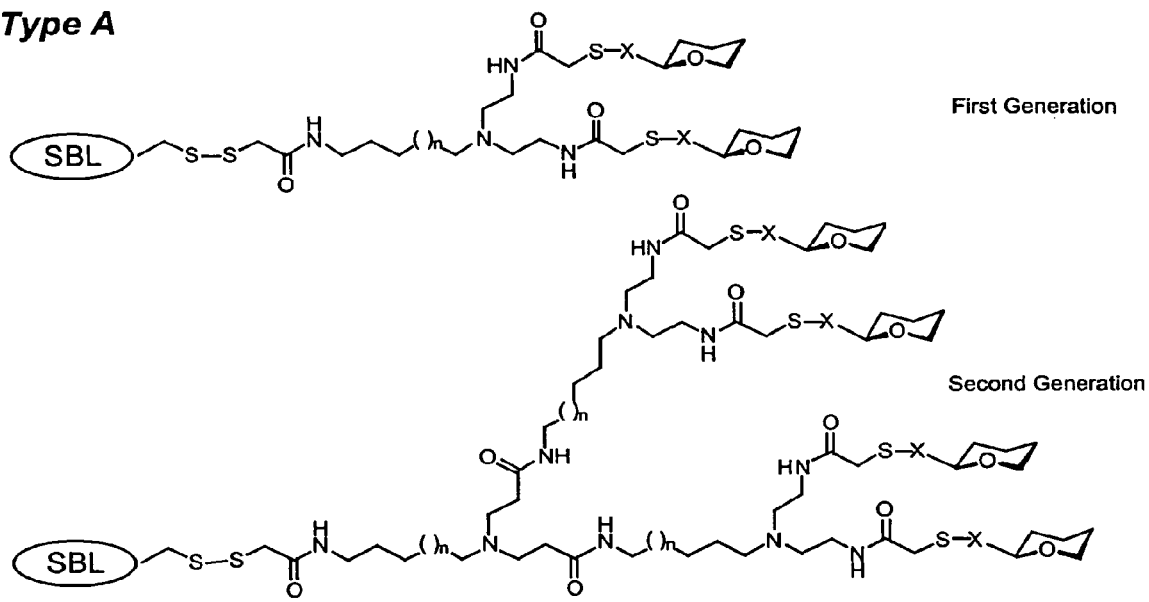
First Generation
Second Generation
Type B
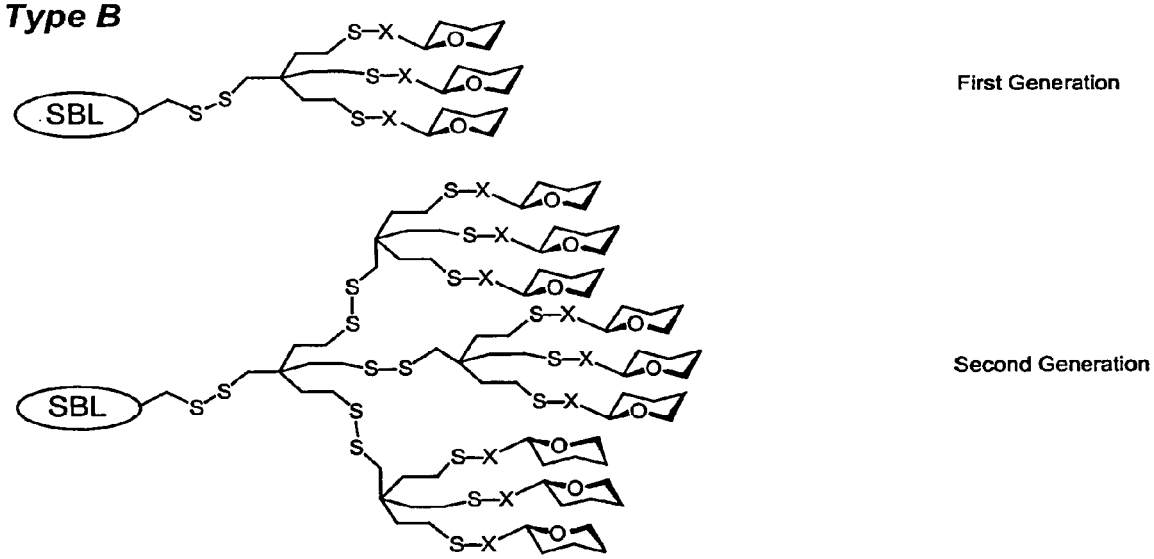
First Generation
Second Generation
where X = S or S(CH$_2$)$_m$O
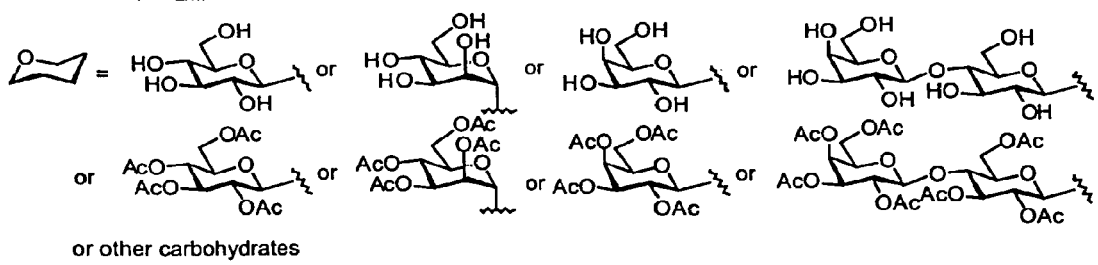
or other carbohydrates
*Fig. 1*

Scheme 11 where for b-f: X = H, g-k: X = Ac

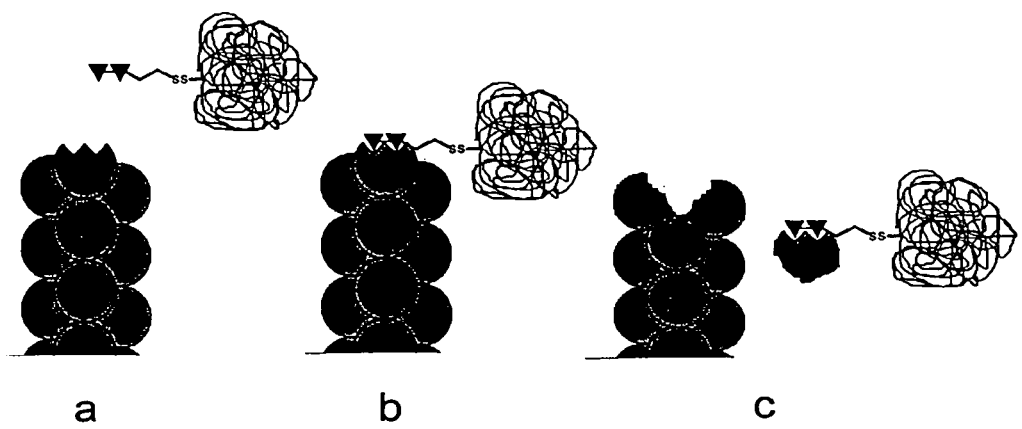
*Fig. 14A*   *Fig. 14B*   *Fig. 14C*

Scheme 7:

US 8,431,121 B2

SPECIFICALLY TARGETED CATALYTIC ANTAGONISTS AND USES THEREOF

CROSS-REFERENCE TO RELATED APPLICATIONS

This application is a continuation of U.S. application Ser. No. 10/791,628, filed on Mar. 1, 2004, which is a continuation of U.S. application Ser. No. 09/556,466, filed on Apr. 21, 2000 (now abandoned), which claims priority to U.S. Provisional Application No. 60/131,362, filed on Apr. 28, 1999, all of which applications are hereby incorporated by reference in their entirety.

STATEMENT AS TO RIGHTS TO INVENTIONS MADE UNDER FEDERALLY SPONSORED RESEARCH AND DEVELOPMENT

Not Applicable

FIELD OF THE INVENTION

This invention relates to the field of chimeric molecules. In particular this invention provides novel chimeric molecules that act as catalytic antagonists of targets (e.g. receptors, enzymes, lectins, etc.).

BACKGROUND OF THE INVENTION

In a chimeric molecule, two or more molecules that exist separately in their native state are joined together to form a single molecule having the desired functionality of all of its constituent molecules. Frequently, one of the constituent molecules of a chimeric molecule is a "targeting molecule". The targeting molecule is a molecule such as an antibody that specifically binds to its corresponding target and, by virtue of the targeting molecule, the chimeric molecule will specifically bind (target) cells and tissues bearing the target (e.g. the epitope) to which the targeting moiety is directed.

Another constituent of the chimeric molecule may be an "effector molecule". The effector molecule refers to a molecule that is to be specifically transported to the target to which the chimeric molecule is specifically directed.

Chimeric molecules comprising a targeting moiety attached to an effector moiety have been used in a wide variety of contexts. Thus, for example, chimeric molecules comprising a targeting moiety joined to a cytotoxic "effector molecule" have frequently been used to target and kill tumor cells (see, e.g., Pastan et al., *Ann. Rev. Biochem.*, 61: 331-354 (1992). Other chimeric molecules comprising a targeting moiety attached to angiogenesis inhibitors have been used to inhibit tumor growth and/or proliferation. Conversely, angiogenesis inducers) have been proposed for the treatment of atherosclerosis. Other uses of chimeric molecules have involved the delivery of intrabodies, intracellularly expressed antibodies that then bind to an intracellular protein, the specific delivery of vectors (e.g. for gene therapy), or the creation of tissue-specific liposomes.

Typically, the target recognized by the targeting moiety is not the desired site of action of the effector molecule. Thus, for example, in the case of chimeric cytotoxins used to treat cancers (e.g. IL4-PE, B1FvPE38, etc., see, e.g., Benhar & Pastan (1995) *Clin. Canc. Res.*, 1: 1023-1029, Thrush et al. (1996) *Ann. Rev. Immunol.*, 14: 49-71, etc.) the targeting moiety specifically binds to a target on the surface of the cell. The chimeric molecule is then internalized into the cell and the effector molecule (e.g., ricin, abrin, Diptheria toxin, *Pseudomonas* exotoxin) is transported to the cytosol of the cell where it exerts its characteristic activity (e.g. ADP ribosylation in the case of *Pseudomonas* exotoxin).

Similarly, targeted liposomes are typically internalized through a receptor-mediated process or through the action of the lipid. Targeted intrabodies and gene therapy vectors are also internalized for expression within the cell. In addition, a common goal in the design of targeted chimeric molecules has been the increase of binding specificity and avidity. It is generally believed that, by increasing avidity and specificity the concentration of the chimeric molecule to achieve a given result will decrease. Thus, release of the chimeric molecule from its target is generally viewed as undesirable.

Because the chimeric molecule is typically internalized (in the case of targeted cells) and the activity of the effector molecule is directed to a molecule other than the specifically recognized target, chimeric molecules typically act in a "stoichiometric" manner. That is, each chimeric molecule is essentially consumed upon interaction with its "substrate" and activity of the chimeric molecule is unavailable for subsequent reactions. As a consequence chimeric molecules must be maintained at relatively high level for efficacy and a recurring problem of chimeric moieties, particularly in in vivo applications is the inability to maintain elevated serum levels of the chimeric molecule over therapeutically significant periods of time and the increased (e.g. non-specific) toxicity caused by the high dosages that must be utilized.

Attempts at solving these problems have focused on reducing the immunogenicity of the chimera (e.g. by using humanized antibodies, antibody fragments, small fusion proteins, etc.) or "masking" the chimeric molecule (e.g. "stealth" liposomes). In particular, the impetus to reduced immunogenicity, improved tumor penetration, and the like, has led to the increasing use of fusion proteins instead of chemically coupled moieties in chimeric molecules (see, e.g., Pastan, (1992) *Ann. Rev. Biochem.*, 61: 331-354; Thrush (1996) *Ann. Rev. Immunol.*, 14: 49-71; Brinkmann and Pastan (1994) *Biochim. Biophys. Acta*, 1198: 27-45, etc.), but have not addressed the actual stoichiometry or kinetics of the chimera.

SUMMARY OF THE INVENTION

This invention provides a novel approach to the design of chimeric molecules. In one embodiment, the molecules of this invention specifically bind to a target molecule and degrade that bound molecule. In preferred embodiments, this results in a loss of activity (e.g. biological activity) of the target molecule and also results in the release of the chimeric molecule so that it is free to find and degrade another target. In this manner the chimeric molecule is "regenerated" and essentially catalytic. Because a single chimeric molecule can attack and degrade an essentially limitless number of targets, the so called "catalytic antagonists" of this invention are highly effective at relatively low dosages.

Thus, in one embodiment, this invention provides a catalytic antagonist of a target molecule (e.g. an enzyme, a receptor, etc.). The antagonist comprises a targeting moiety that specifically binds to the target molecule and the targeting moiety is attached to an enzyme that degrades the target molecule to reduce binding of the target molecule to its cognate ligand. In particularly preferred embodiments, the degradation of the target molecule also reduces binding of the antagonist to the target molecule. Thus, in these embodiments, the antagonist is released from the target thereby allowing the antagonist to bind and degrade another target molecule.

In particularly preferred embodiments the targeting moiety is joined to the enzyme through the sulfur group on a cysteine and the cysteine is a naturally occurring cysteine in the enzyme or a cysteine introduced into the enzyme (e.g. substituted for a native amino acid other than cysteine in the enzyme). In certain preferred embodiments, the cysteine is a cysteine that is substituted for a native amino acid other than cysteine in or near a subsite comprising a substrate binding site of the enzyme. In some embodiments, the cysteine is a cysteine that is substituted for an amino acid forming a substrate binding site.

Preferred enzymes include, but are not limited to a protease, an esterase, an amidase, a peptidase, a lactamase, a cellulase, an oxidase, an oxidoreductase, a reductase, a transferase, a hydrolase, an isomerase, a ligase, a lipase, a phospholipase, a phosphatase, a kinase, a sulfatase, a lysozyme, a glycosidase, a nuclease, an aldolase, a ketolase, a lyase, a cyclase, a reverse transcriptase, a hyaluronidase, an amylase, a cerebrosidase, and a chitinase. In a particularly preferred embodiment, the enzyme is a serine hydrolase. In an even more preferred embodiment, the enzyme is a subtilisin-type serine hydrolase (e.g. a *Bacillus lentus* subtilisin) and said cysteine is substituted for an amino acid in or near a subsite selected from the group consisting of an S1 subsite, an S1' subsite, and an S2 subsite.

In a particularly preferred embodiment the enzyme is a *Bacillus lentus* subtilisin. In preferred embodiments, the cysteine is substituted for an amino acid in a subtilisin, where the amino acid corresponds to a reference residue in a *Bacillus lentus* subtilisin, where the reference residue is at or near a residue selected from the group consisting of residue 156, residue 166, residue 217, residue 222, residue 62, residue 96, residue 104, residue 107, residue 189, and residue 209.

In another embodiment the enzyme is a chymotrypsin-type serine protease and the cysteine is substituted for the amino acid corresponding to a reference residue in a mature trypsin (Protein Data Bank entry 1TPP), wherein said reference residue is at or near a residue selected from the group consisting of Tyr94, Leu99, Gln175, Asp189, Ser190, Gln192, Phe41, Lys60, Tyr151, Ser214, and Lys224.

In still another embodiment the enzyme is an alpha/beta type serine hydrolase and the cysteine is substituted for the amino acid corresponding to a reference residue in a *Candida antartica* lipase (Protein Data Bank entry 1TCA), where the reference residue is at or near a residue selected from the group consisting of Trp104, Leu140, Leu144, Val154, Glu188, Ala 225, Leu278 and Ile285.

In yet another embodiment the enzyme is an aspartyl protease. More preferably the enzyme is a pepsin-type protease and the cysteine is substituted for the amino acid corresponding to a reference residue in the mature human pepsin (Protein Data Bank entry 1PSN), where the reference residue is at or near a residue selected from the group consisting of Tyr9, Met12, Glu13, Gly76, Thr77, Phe111, Phe117, Ile128, Ser130, Tyr189, Ile213, Glu239, Met245, Gln287, Met289, Leu291, and Glu294.

In still yet another embodiment the enzyme is a cysteine protease. More preferably the enzyme is a papain and the cysteine is substituted for the amino acid corresponding to a reference residue in a mature papain (Protein Data Bank entry 1BQI), where the reference residue is at or near a residue selected from the group consisting of Asn18, Ser21, Asn64, Tyr67, Trp69, Gln112, Gln 142, Asp158, Trp177, and Phe207.

In certain embodiments the enzyme is a metalloprotease and the cysteine is substituted for the amino acid corresponding to a reference residue in the mature human matrix metalloprotease (Protein Data Bank entry 830C), where the reference residue is at or near a residue selected from the group consisting of Leu111, Phe175, Tyr176, Ser182, Leu184, Phe189, Tyr214, Asp231, Lys234, and Ile243.

In certain embodiments the catalytic antagonist targeting moiety is directed against a target where the target is a molecule present on the surface of a Cell (e.g., a molecule forming a receptor, a ligand, a component of a cell wall, a component of a cell membrane, etc.). In certain embodiments the targeting moiety includes, but is not limited to an antigen, a carbohydrate, a nucleic acid, a lipid, a coordination complex, a sugar, a vitamin, a dendrimer, and a crown ether. In a particularly preferred embodiment the targeting moiety is a cognate ligand for a receptor or an enzyme. In another particularly preferred embodiment the targeting moiety is an inhibitor for a receptor or an enzyme.

In certain preferred embodiments, the enzyme is a protease (e.g. a papain, a subtilisin, a pepsin, a trypsin, a metalloprotease, etc.) and the targeting moiety is a ligand selected from the group consisting of a carbohydrate, a vitamin or vitamin analog, an enzyme inhibitor, a peptide, a pharmaceutical that is a small organic molecule, and biotin. In another embodiment the enzyme is a protease and said targeting moiety is a receptor.

In certain preferred embodiments, the enzyme is a protease (e.g. a papain, a subtilisin, a pepsin, a trypsin, a metalloprotease, etc.) and the targeting moiety is an enzyme inhibitor that is a pyrazole, a biotin, a ligand that binds a lectin (e.g. concanavalin A), a carbohydrate (e.g. thioethyl D-mannopyranoside). In one particularly preferred embodiment the targeting moiety specifically binds to a soil and the enzyme degrades a component of the soil.

In another embodiment this invention provides a method of degrading a target molecule. The method involves contacting the target molecule with a catalytic antagonist comprising a targeting moiety that specifically binds to the target molecule the targeting moiety being attached to an enzyme that degrades the target molecule. In a preferred embodiment the degradation of the target molecule releases the antagonist thereby allowing the antagonist to bind and degrade another target molecule. In preferred embodiments, the targeting moiety is joined to the enzyme through the sulfur group on a cysteine. Preferred antagonist molecules include, but are not limited to the catalytic antagonist molecules described above.

In still another embodiment, this invention provides an enzyme having altered substrate specificity (i.e. a "redirected enzyme). The enzyme preferably comprises a targeting moiety attached to a subsite comprising the substrate binding site of said enzyme. In preferred embodiments, the targeting moiety is coupled to said enzyme through to a sulfur of a cysteine in said subsite of said enzyme. The cysteine may be a native cysteine or a cysteine is substituted for a native amino acid that is not cysteine in the subsite of the enzyme. Preferred enzymes include, but are not limited to a protease, an esterase, an amidase, a peptidase, a lactamase, a cellulase, an oxidase, an oxidoreductase, a reductase, a transferase, a hydrolase, an isomerase, a ligase, a lipase, a phospholipase, a phosphatase, a kinase, a sulfatase, a lysozyme, a glycosidase, a glycosyltransferase, a nuclease, an aldolase, a ketolase, a lyase, a cyclase, a reverse transcriptase, a hyaluronidase, an amylase, a cerebrosidase and a chitinase.

In particularly preferred embodiments, the enzyme is a serine hydrolase (e.g., a subtilisin). In a subtilisin, the cysteine is preferably substituted for amino acids at or near a subsite selected from the group consisting of an S1 subsite, an S1' subsite, and an S2 subsite. Particularly preferred sites for substitution of the cysteine in various enzymes include, but are not limited to those identified above. Similarly, particularly preferred targets and targeting moieties include those identified above. In certain embodiments the targeting moiety is an inhibitor for a receptor or an enzyme, in other embodiments the targeting moiety is selected from the group consisting of a growth factor, a cytokine, and a receptor ligand. In certain embodiments, the enzyme is a protease and the targeting moiety is a ligand selected from the group consisting of a carbohydrate, a vitamin or vitamin analog, an enzyme inhibitor, a peptide, a pharmaceutical that is a small organic molecule, and biotin. In one particularly preferred embodiment the enzyme is a protease (e.g. a subtilisin, a papain, a pepsin, etc.) and the targeting moiety is a receptor, enzyme inhibitor that is a pyrazole, a biotin, a ligand that binds a lectin (e.g. concanavalin A), or a carbohydrate (e.g. thioethyl D-mannopyranoside). In one embodiment the targeting moiety specifically binds to a soil and said enzyme degrades a component of the soil.

In still yet another embodiment this invention provides methods of directing the activity of an enzyme to a specific target. The methods comprise providing an enzyme having altered substrate specificity said enzyme comprising a targeting moiety attached to a subsite within the substrate binding region of said enzyme; and contacting the target with the enzyme, whereby the enzyme specifically binds to the target thereby localizing the activity of the enzyme at the target. Preferred enzymes include, but are not limited to, the "redirected" enzymes described above.

This invention also provides methods of enhancing the activity of a drug that acts as an inhibitor of a receptor or an enzyme. The methods involve coupling a hydrolase to said drug such that when said drug binds said receptor or enzyme, the hydrolase degrades the receptor or enzyme. In preferred embodiments, the method increases the dosage therapeutic window of said drug. In one particularly preferred embodiments the hydrolase is a serine hydrolase (e.g. a subtilisin). In certain preferred embodiments, the hydrolase is a metalloprotease, a cysteine protease, an aspartyl protease, and the like.

This invention also provides a method of inhibiting an enzyme or a receptor. The method comprises contacting the enzyme or receptor with a chimeric molecule comprising a ligand that binds the enzyme or receptor attached to an enzyme that degrades the cognate ligand of the enzyme or receptor. The enzyme thus becomes linked to the enzyme or receptor where it is free to degrade the cognate ligand thereby preventing the cognate ligand from activating the receptor or acting as a substrate for the enzyme. In a preferred embodiment the chimeric molecule comprises a hydrolase (e.g. a protease) attached to an inhibitor of the enzyme or receptor. Preferred hydrolases include, but are not limited to a serine protease, a cysteine protease, an aspartyl protease, a pepsin-type protease, and a metalloprotease.

In certain embodiments, this invention does not include catalytic antibodies, e.g. as described by Hifumi et al. (1999) *J. Bioscience and Bioengineering*, 88: 323.

DEFINITIONS

The term "catalytic antagonist", as used herein refers to an enzyme that can inhibit the activity of a molecule that has a particular biological activity and/or simply degrade a molecule that has no particular biological activity. The inhibition can be a blocking or destroying of the function of the "target" molecule. In preferred embodiments, the inhibition or blockage is by partial or complete degradation of the target molecule. The "catalytic antagonist" is catalytic by virtue of the fact that the antagonist is not itself consumed or significantly altered (i.e., permanently changed) by its interaction with the target molecule. Thus, in preferred embodiments, the degradation of the target molecule ultimately results in the release of the catalytic antagonist so that it is free to attack another target molecule. The reaction is preferably sub-stoichiometric (ratio of catalytic antagonist to target is less than 1) and a single catalytic antagonist is free to degrade any number of target molecules.

A "target molecule" refers to a molecule that is specifically bound by the catalytic antagonist or specifically directed enzymes described herein. Where a catalytic antagonist is employed the target molecule is partially or completely degraded by that antagonist.

A "targeting moiety" refers to a moiety in the chimeric molecule that that specifically binds to the target molecule. Prior to coupling the targeting moiety to the enzyme, the targeting moiety is a targeting molecule. In preferred embodiments, the targeting moiety is one of a pair of cognate binding partners.

The term "specifically binds", when referring to the interaction of a targeting moiety and its cognate binding partner refers to a binding reaction which is determinative of the presence of the targeting moiety or the cognate molecule in the presence of a heterogeneous population of molecules (e.g., proteins and other biologics). Thus, for example, in the case of a receptor/ligand binding pair the ligand would specifically and/or preferentially select its receptor from a complex mixture of molecules, or vice versa. The binding may be by one or more of a variety of mechanisms including, but not limited to ionic interactions, covalent interactions, hydrophobic interactions, van der Waals interactions, etc.

The terms "binding partner", or a member of a "binding pair", or "cognate ligand" refers to molecules that specifically bind other molecules to form a binding complex such as antibody/antigen, lectin/carbohydrate, nucleic acid/nucleic acid, receptor/receptor ligand (e.g. IL-4 receptor and IL-4), avidin/biotin, etc.

The term ligand is used to refer to a molecule that specifically binds to another molecule. Commonly a ligand is a soluble molecule, e.g. a hormone or cytokine, that binds to a receptor. The decision as to which member of a binding pair is the ligand and which the "receptor" is often a little arbitrary when the broader sense of receptor is used (e.g., where there is no implication of transduction of signal). In these cases, typically the smaller of the two members of the binding pair is called the ligand. Thus, in a lectin-sugar interaction, the sugar would be the ligand (even if it is attached to a much larger molecule, recognition is of the saccharide).

The terms "polypeptide", "oligopeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Proteins also include glycoproteins (e.g. histidine-rich glycoprotein (HRG), Lewis Y antigen (Le$^Y$), and the like.).

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphosphoroamidite linkages (see Eckstein, Oligonucleotides and Analogues: A Practical Approach, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature*, 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Letsinger et al. (1988) *J. Am. Chem. Soc.* 110:4470; Letsinger et al. (1994) *Nucleoside & Nucleotide* 13:1597; Chapters 2 and 3, ACS Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; Tetrahedron Lett. 37:743 (1996)) and non-ribose backbones, including those described in U.S. Pat. Nos. 5,235,033 and 5,034,506, and Chapters 6 and 7, ACS Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "residue" as used herein refers to natural, synthetic, or modified amino acids.

The term enzyme includes proteins that are capable of catalyzing chemical changes in other substances without being permanently changed themselves. The enzymes can be wild-type enzymes or variant enzymes. Enzymes within the scope of the present invention include, but are not limited to, proteases, esterases, amidases, peptidases, lactamases, cellulases, oxidases, oxidoreductases, reductases, transferases, hydrolases, isomerases, ligases, lipases, phospholipases, phosphatases, kinases, sulfatases, lysozymes, glycosidases, glycosyltransferases, nucleases, aldolases, ketolases, lyases, cyclases, reverse transcriptases, hyaluronidases, amylases, cerebrosidases, chitinases, and the like.

A "mutant enzyme" is an enzyme that has been changed by replacing an amino acid residue with a cysteine (or other) residue.

A "chemically modified" enzyme is an enzyme that has been derivatized to bear a substituent not normally found at that location in the enzyme. The derivatization typically is of a post translational modification, occasionally performed in vivo, but more typically performed ex vivo.

A "chemically modified mutant enzyme" or "CMM" is an enzyme in which an amino acid residue has been replaced with another amino acid residue (preferably a cysteine) and the replacement residue is chemically derivatized to bear a substituent not normally found on that residue.

The term "thiol side chain group", "thiol containing group", and "thiol side chain" are terms that can be used interchangeably and include groups that are used to replace the thiol hydrogen of a cysteine. Commonly the thiol side chain group includes a sulfur atom through which the thiol side chain group that is attached to the thiol sulfur of the cysteine. The "substituent" typically refers to the group remains attached to the cysteine through a disulfide linkage formed by reacting the cysteine with a methanesulfonate reagent as described herein. While the term substituent preferably refers just to the group that remains attached (excluding its thiol group), the substituent can also refer to the entire thiol side chain group. The difference will be clear from the context.

The "binding site of an enzyme" consists of a series of subsites across the substrate binding surface of the enzyme (Berger & Schechter (1970) *Phil. Trans. Roy Soc. Lond. B* 257: 249-264). The substrate residues that correspond to the subsites are labeled P and the subsites are labeled S. By convention, the subsites are labeled $S_1$, $S_2$, $S_3$, $S_4$, $S_1'$, and $S_2'$. A discussion of subsites can be found in Siezen et al. (1991) *Protein Engineering*, 4: 719-737, and Fersht (1985) *Enzyme Structure and Mechanism*, 2nd ed. Freeman, N.Y., 29-30. The preferred subsites include $S_1$, $S_1'$, and $S_2$.

The phrase "amino acid ##" or "amino acid ## in the XX subsite" is intended to include the amino acid at the referenced position (e.g. amino acid 156 of *B. lentus* subtilisin which is in the $S_1$ subsite) and the amino acids at the corresponding (homologous) position in related enzymes.

A residue (amino acid) of an enzyme is equivalent to a residue of a referenced enzyme (e.g. *B. amyloliquefaciens* subtilisin) if it is either homologous (i.e., corresponding in position in either primary or tertiary structure) or analogous to a specific residue or portion of that residue in *B. amyloliquefaciens* subtilisin (i.e., having the same or similar functional capacity to combine, react, or interact chemically).

In order to establish homology to primary structure, the amino acid sequence of the subject enzyme (e.g. a serine hydrolase, cysteine protease, aspartyl protease, metalloprotease, etc.) is directly compared to a reference enzyme (e.g. *B. amyloliquefaciens* subtilisin in the case of a subtilisin type serine protease) primary sequence and particularly to a set of residues known to be invariant in all enzymes of that family (e.g. subtilisins) for which sequence is known. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of the reference enzyme (e.g. *B. amyloliquefaciens* subtilisin) are defined. Alignment of conserved residues preferably should conserve 100% of such residues. However; alignment of greater than 75% or as little as 50% of conserved residues is also adequate to define equivalent residues. Conservation of the catalytic triad, (e.g., Asp32/His64/Ser221) should be maintained for serine hydrolases.

The conserved residues may be used to define the corresponding equivalent amino acid residues in other related enzymes. For example, the two (reference and "target") sequences are aligned in order to produce the maximum homology of conserved residues. There may be a number of insertions and deletions in the "target" sequence as compared to the reference sequence. Thus, for example, a number of deletions are seen in the thermitase sequence as compared to *B. amyloliquefaciens* subtilisin (see, e.g. U.S. Pat. No. 5,972,682). Thus, the equivalent amino acid of Tyr217 in *B. amyloliquefaciens* subtilisin in thermitase is the particular lysine shown beneath Tyr217 in FIG. 5B-2 of the U.S. Pat. No. 5,972,682.

The particular "equivalent" resides may be substituted by a different amino acid to produce a mutant carbonyl hydrolase since they are equivalent in primary structure.

Equivalent residues homologous at the level of tertiary structure for a particular enzyme whose tertiary structure has been determined by x-ray crystallography, are defined as those for which the atomic coordinates of 2 or more of the main chain atoms of a particular amino acid residue of the reference sequence (e.g. *B. amyloliquefaciens* subtilisin) and the sequence in question (target sequence) (N on N, CA on CA, C on C, and O on O) are within 0.13 nm and preferably 0.1 nm after alignment. Alignment is achieved after the best model has been oriented and positioned to give the maximum overlap of atomic coordinates of non-hydrogen protein atoms of the enzyme in question to the reference sequence. The best model is the crystallographic model giving the lowest R factor for experimental diffraction data at the highest resolution available.

$$R = \frac{\sum_h |Fo(h)| - |Fc(h)|}{\sum_h |Fo(h)|}$$

Equivalent residues which are functionally analogous to a specific residue of a reference sequence (e.g. *B. amyloliquefaciens* subtilisin) are defined as those amino acids sequence in question (e.g. related subtilisin) which may adopt a conformation such that they will alter, modify or contribute to protein structure, substrate binding or catalysis in a manner defined and attributed to a specific residue of the reference sequence as described herein. Further, they are those residues of the sequence in question (for which a tertiary structure has been obtained by x-ray crystallography), which occupy an analogous position to the extent that although the main chain atoms of the given residue may not satisfy the criteria of equivalence on the basis of occupying a homologous position, the atomic coordinates of at least two of the side chain atoms of the residue lie with 0.13 nm of the corresponding side chain atoms of the reference sequence residue(s). The three dimensional structures would be aligned as outlined above. For an illustration of this procedure see U.S. Pat. No. 5,972,682.

A "reference residue" refers to a residue that is specified in a particular enzyme and which serves as a "reference point" for identifying, e.g., as described above, equivalent residues in other members of the family of which the reference enzyme is a member. Thus, the phrase "the amino acid corresponding to a reference residue in the mature human protein X" refers to residues equivalent (or homologous) to the reference residue of protein X in other members of the same protein family. In addition, where the subject protein is protein X, the phrase refers to the reference residue itself.

A "serine hydrolase" is a hydrolytic enzyme utilizing an active serine side chain to serve as a nucleophile in a hydrolytic reaction. This term includes native and synthetic serine hydrolases as well as enzymes engineered to perform the reverse reaction, e.g., for synthetic purposes. The family of serine peptidases is characterized by Bartlett and Rawlings (1994) *Meth. Enzymol.*, 244: 19-61, Academic Press, S.D.

The "alpha/beta serine hydrolases" are a family of serine hydrolyases based on structural homology to enzymes including wheat germ serine carbokypeptidase's II (see, e.g., Liam et al. (1992) *Biochemistry* 31: 9796-9812; 011 is et al. (1992) *Protein Engineering,* 5: 197-211).

The term "aspartyl proteases", also known as aspartic proteases, are proteases that are directly dependent on aspartic acid residues for catalytic activity. The family of aspartyl proteases is characterized in a number of publications known to those of skill in the art (see, e.g., Rawlings and Barrett, (1995) *Meth. Enzymology,* 248: 105-120, Academic Press, S.D.).

The term "cysteine proteases" is used herein consistently with conventional usage of those of skill in the art. The family of cysteine proteases is characterized in a number of publications known to those of skill in the art (see, e.g., Rawlings and Barrett, (1994) *Meth. Enzymology,* 224: 461-486, Academic Press, S.D.).

The term "metalloproteases" is used herein consistently with the conventional usage of those of skill in the art. The family of metalloproteases is characterized in a number of publications known to those of skill in the art (see, e.g., Rawlings and Barrett, (1995) *Meth. Enzymology,* 248: 183-228, Academic Press, S.D.)

The "subtilisin type serine proteases" refer to a family of serine hydrolyases based on structural homology to enzymes derived from *Bacillus subtilus,* including subtilisin BPN' (Bott et al. (1988) *J. Biol. Chem.* 263: 7895-7906; Siezen and Louise (1997) *Protein Science* 6: 501-523; Bartlett and Rawlings (1994) *Meth. Enzymol.,* 244: 19-61, Academic Press, S.D.). Subtilisins are bacterial or fungal proteases which generally act to cleave peptide bonds of proteins or peptides. As used herein, "subtilisin" means a naturally-occurring subtilisin or a recombinant subtilisin. A series of naturally-occurring subtilisins is known to be produced and often secreted by various microbial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases have a catalytic triad comprising aspartate, histidine and serine. In the subtilisin related proteases the relative order of these amino acids, reading from the amino to carboxy terminus, is aspartate-histidine-serine. In the chymotrypsin related proteases, the relative order, however, is histidine-aspartate-serine. Thus, subtilisin herein refers to a serine protease having the catalytic triad of subtilisin related proteases.

The "chymotrypsin serine protease family" refers to a family of serine hydrolyases based on structural homology to enzymes including gamma chymotrypsin (Birktoft and Blow (1972) *J. Molecular Biology* 68: 187-240).

A "dendritic polymer" is a polymer exhibiting regular dendritic branching, formed by the sequential or generational addition of branched layers to or from a core. The term dendritic polymer encompasses "dendrimers", which are characterized by a core, at least one interior branched layer, and a surface branched layer (see, e.g., Petar et al. Pages 641-645 In *Chem. in Britain,* (August 1994). A "dendron" is a species of dendrimer having branches emanating from a focal paint which is or can be joined to a core, either directly or through a linking moiety to form a dendrimer. Many dendrimers comprise two or more dendrons joined to a common core. However, the term dendrimer is used broadly to encompass a single dendron.

Dendritic polymers include, but are not limited to, symmetrical and unsymmetrical branching dendrimers, cascade molecules, arborols, dense star polymers, and the like. The PAMAM dense star dendrimers (disclosed in U.S. Pat. No. 5,714,166) are symmetric, in that the branch arms are of equal length. The branching occurs at the nitrogen atom of a terminal amine group on a preceding generation branch. The lysine-based dendrimers are unsymmetric, in that the branch arms are of a different length. One branch occurs at the epsilon nitrogen of the lysine molecule, while another branch occurs at the alpha nitrogen, adjacent to the reactive carboxy group which attaches the branch to a previous generation branch.

Even though not formed by regular sequential addition of branched layers, hyperbranched polymers, e.g., hyperbranched polyols, may be equivalent to a dendritic polymer where the branching pattern exhibits a degree of regularity approaching that of a dendrimer.

As used herein, an "antibody" refers to a protein or glycoprotein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well characterized fragments produced by digestion with various peptidases. Thus, for example, pepsin digests an antibody below (i.e. toward the Fc domain) the disulfide linkages in the hinge region to produce F(ab)' 2, a dimer of Fab which itself is a light chain joined to $V_H$-$C_H$1 by a disulfide bond. The F(ab)' 2 may be reduced under mild conditions to break the disulfide linkage in the hinge region thereby converting the $(Fab')_2$ dimer into an Fab' monomer. The Fab' monomer is essentially a Fab with part of the hinge region (see, Paul (1993) *Fundamental Immunology*, Raven Press, N.Y. for a more detailed description of other antibody fragments). While various antibody fragments are defined in terms of the digestion of an intact antibody, one of skill will appreciate that such fragments may be synthesized de novo either chemically, by utilizing recombinant DNA methodology, or by "phage display" methods (see, e.g., Vaughan et al. (1996) *Nature Biotechnology*, 14(3): 309-314, and PCT/US96/10287). Preferred antibodies include single chain antibodies, e.g., single chain Fv (scFv) antibodies in which a variable heavy and a variable light chain are joined together (directly or through a peptide linker) to form a continuous polypeptide.

The term "carbohydrate" includes mono-, oligo- and polysaccharides as well as substances derived from monosaccharides by reduction of the carbonyl group (alditols), by oxidation of one or more terminal groups to carboxylic acids, or by replacement of one or more hydroxy group(s) by an hydrogen atom, an amino group, a thiol group or similar heteroatomic groups. It also includes derivatives of these compounds. The term "sugar" is frequently applied to monosaccharides and lower oligosaccharides. Parent monosaccharides are polyhydroxy aldehydes H—$[CHOH]_n$—CHO or polyhydroxy ketones H—$[CHOH]_n$—CO—$[CHOH]_m$—H with three or more carbon atoms. The generic term "monosaccharide" (as opposed to oligosaccharide or polysaccharide) denotes a single unit, without glycosidic connections to other such units. It also includes aldoses, dialdoses, aldoketoses, ketoses and diketoses, as well as deoxy sugars and amino sugars, and their derivatives, provided that the parent compound has a (potential) carbonyl group (see, e.g., McNaught (1996) *Pure Appl. Chem.* 68: 1919-2008)]. The smallest are monosaccharides like glucose, ribose and threose. Carbohydrates also include, but are not limited to, oligosaccharides and polysaccharides (e.g. starch, cellulose, glycogen) and carbohydrate analogues (e.g., those in which OH have been replaced by H, F, $NH_2$ or $NHC(O)CH_3$).

The term "soil" or "stain" refers to the accumulation of foreign material on a substrate of interest (e.g. a textile). The "soil" or "stain" may have no biological activity, but may serve to discolor, and/or degrade the underlying substrate. The "soil" need not be visible to the naked eye. Deposition of foreign materials that, while not visible to the naked eye, but that create odors or support bacterial growth are also considered "soils" in the context of this application. Typical stains or soils include, but are not limited to grass stains, blood stains, milk stains, egg, egg white, and the like.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

The term "near" or "adjacent to", when used to indicate a location with respect to a particular amino acid residue (e.g. "adjacent to residue 149") refers to a residue covalently attached to the "reference residue", either preceding or following that residue, or in van der Waals contact with the reference residue.

BRIEF DESCRIPTION OF THE DRAWINGS

FIG. 1 illustrates a variety of chimeric molecules of this invention utilizing dendrimers as targeting moieties.

FIG. 14A, FIG. 14B, and FIG. 14C illustrate selective lectin degradation by sugar-modified GG36-WT.

DETAILED DESCRIPTION

Figure 2:
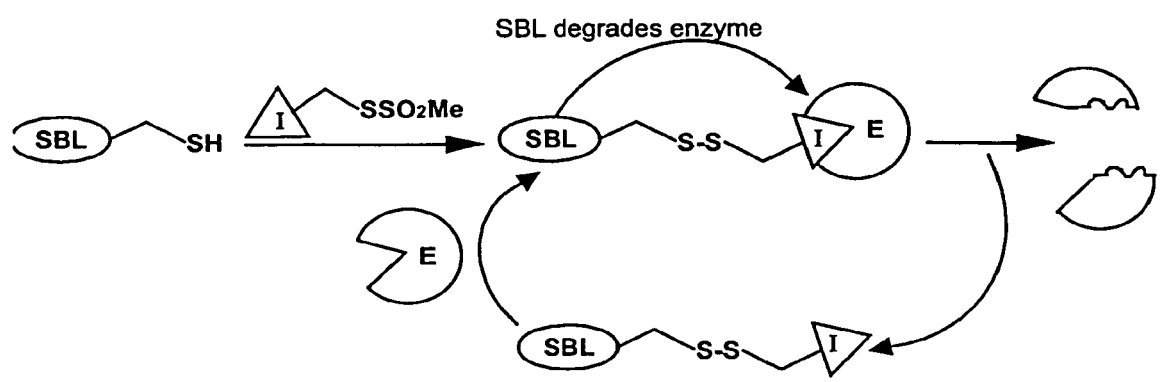
FIG. 2 illustrates SBL targeting an enzyme with an inhibitor.

I. Catalytic Antagonists.

This invention provides novel chimeric molecules that exploit a fundamentally different mode of activity to avoid problems of dosage, activity and persistence problems often associated with the activity of chimeric molecules. In one embodiment, the chimeric molecules are catalytic antagonists of a target molecule. The catalytic antagonists of this invention preferably comprise a targeting moiety attached to an enzyme that degrades the molecule specifically bound by the targeting moiety. The catalytic antagonists of this invention thus bind to a target recognized by the targeting moiety (e.g. a receptor) the enzyme component of the chimera then degrades all or part of the target. This preferably resulting in a reduction or loss of activity of the target and release of the chimeric molecule. The chimeric molecule is then free to attack and degrade another target molecule.

Thus, unlike typical, chimeric molecules in which the chimeric molecule is effective only once (e.g. due to expenditure of the effector activity, and/or internalization and/or lysis of the chimera) a chimeric molecule of this invention is free to attack and degrade essentially a limitless number of targets. In preferred embodiments, the antagonists of this invention are thus catalytic in nature being effectively regenerated (rendered available again) after degrading each substrate molecule (target). The activity of the catalytic antagonists of this invention is thus essentially sub-stoichiometric.

As a consequence, the catalytic antagonists of this invention are effective in far lower concentrations than chimeric molecules or traditional inhibitors. Consequently formulations (e.g. detergents) comprising the catalytic inhibitors of this invention can utilize significantly lower concentrations of inhibitor and can be fabricated at lower cost. In in vivo applications, the catalytic inhibitors of this invention because they offer greater activity at lower concentration, are expected to show longer effective serum half-life and lower toxicities than "traditional" chimeric molecules.

The catalytic antagonists of this invention are useful in a wide variety of contexts where it is desired to degrade a target molecule and/or inhibit the activity of that target molecule. Thus, for example, in ex vivo applications, the catalytic antagonists can be used to specifically target and degrade a particular molecule. Thus, for example, in cleaning operations, the chimeric molecules of this invention can be utilized to specifically target and degrade a component of a soil (e.g. a protein component, a lipid component, etc.). In chemical synthetic processes, or biochemical synthetic processes (e.g. in analytic or industrial preparations, in bioreactors, etc.) to specifically degrade particular preselected molecules. Thus, for example, where it is desired to eliminate a particular enzymatic activity in a bioreactor (e.g. a glycosylation) the catalytic antagonist of this invention comprises, as a targeting moiety, a substrate for the enzyme mediating the activity (e.g. a glycosyltransferase). The enzyme (receptor) in the reactor binds the targeting moiety and the enzymatic component of the chimera (e.g. a hydrolase) degrades the enzyme reducing or eliminating its activity and also freeing itself from the enzyme binding site whereby it is free to attack another target enzyme.

The chimeric molecules of this invention having, e.g. targeting moieties directed against lectins present on bacterial surfaces attached to, e.g. lipases, or hydrolases, are effective antimicrobial agents and can be used in a wide variety of disinfectants.

In biological systems (e.g. in vitro or in vivo) the chimeric molecules of this invention can be used to bind and antagonize/inhibit a wide variety of receptors and/or enzymes, and/or intermediary signaling molecules. A wide variety of drugs act by inhibiting the activity of cellular receptors. Thus, for example, antiestrogens (e.g. tamoxifen) bind to and block estrogen receptors, beta blockers (e.g. digoxin) are used in the management of hypertension and post myocardial infarction, histamine H2 receptor antagonists (cimetidine, ranitidine) are used in the treatment of esophageal reflux disease, selective serotonin (5-HT) reuptake inhibitors (e.g. Prozac, Zoloft, Paxil, etc.) are used in the treatment of depression, and so forth. Chimeric catalytic antagonists of this invention comprising, e.g. a cognate ligand bound by the target receptor or a non-cognate ligand (e.g., a mimetic or drug bound by the receptor), as targeting moiety attached to an enzyme that can degrade the receptor act as effective receptor antagonists.

Unlike a simple competitive inhibitor that "temporarily" blocks the target receptor(s), the catalytic antagonists of this invention effectively degrade the receptor. Thus, once bound and degraded, the receptor is unlikely to function again, absent some repair mechanism. Thus at equal concentrations, the catalytic antagonists of this invention will produce a far greater degree of activity and/or duration of activity than "traditional" competitive inhibitors. It will also be appreciated that, in this context, an enzyme (e.g. an intracellular enzyme) can also be regarded as a receptor for its cognate substrate. Thus, catalytic antagonists of this invention can be used to degrade target enzymes as well. In this instance, it is preferably to use, as the targeting moiety, a molecule that is not degraded or altered by the target enzyme. Known competitive inhibitors of enzymes make good targeting moieties in this context.

In still another embodiment this invention include chemical antagonists (e.g. of receptors and/or enzymes) comprising a targeting moiety that binds to the receptor or enzyme attached to an enzyme that degrades the cognate ligand that binds to that enzyme and/or receptor. The inhibitor of the enzyme or receptor binds and anchors the enzyme comprising the chimeric molecule to the target enzyme or receptor. When the cognate ligand of the receptor or enzyme approaches, the enzyme degrades is and thereby blocks its activity on the receptor. Again, the process is "catalytic" with no permanent change to the chimeric molecule.

In preferred embodiments, the catalytic antagonists of this invention are chemically coupled chimeric molecules. The targeting moiety preferably coupled, directly or through a linker, to either terminus of the enzyme (the amino or carboxyl terminus or through an R group of the terminal amino acid), or more preferably, is coupled, directly or through a linker, to a non-terminal amino acid in the enzyme. In certain particularly preferred embodiments, the catalytic antagonists of this invention comprise a chemically modified mutant (CMM) enzyme. A chemically modified mutant enzyme is an enzyme in which a native amino acid residue is replaced with a different amino acid residue (e.g. cysteine, affording a reactive site suitable for coupling the targeting moiety. Thus, preferred chimeric molecules of this invention are chemically coupled molecules rather than fusion proteins.

The use of chemically coupled targeting moieties in this invention affords a number of advantages. The targeting moiety is not limited to a peptide or protein, but rather can be any of a number of ligands including, but not limited to, known drugs, vitamins, carbohydrates, lectins, and the like. Because the targeting moieties are typically smaller than proteins, they are less immunogenic and show greater tissue penetration. In addition, because the targeting moieties are often various small organic molecules, they retain their conformation and specificity in a physiological context and are typically less subject to degradation in vivo. The chimeric molecules of this invention offer a number of other advantages. Because they are chemically conjugated using a "standard" chemistry, they are easier to make and/or to vary. In addition, the molecules are smaller than typical "therapeutic" fusion proteins (e.g. immunotoxins) and are expected to have increased serum half-life. In addition, because, in certain embodiments, the molecules actually destroy/degrade existing receptors and/or enzymes, a single dosage is expected to have a longer-lasting effect since the subject organisms must actually replace the receptor and/or enzyme to restore that functionality.

II. Retargeting Enzymatic Activity.

In many applications, the catalytic antagonists of this invention can be regarded as enzymes that have been "redirected" so that they either act on a non-native substrate (for the enzymatic component) or, more typically, so that the enzymatic activity is localized at the site of the target molecule. Thus, in some embodiments, this invention provides an enzyme having altered substrate specificity where the enzyme is a component of a chimeric molecule comprising a targeting moiety attached to a subsite comprising the substrate binding site of the enzyme.

Traditionally targeted chimeric molecules are designed to position the targeting moiety/domain some distance away from active sites of interest in the effector moiety. It was generally believed that a targeting moiety located too close to an active site of the effector moiety would interfere with proper functioning of the effector (e.g. via steric hindrance).

It was a surprising discovery of this invention that targeting moieties comprising the chimeric molecules of this invention can be coupled to amino acid residues comprising a substrate binding site of the enzyme. Moreover, attachment of the targeting moiety to an amino acid residue in the substrate binding site of the enzyme results in the substrate binding site being closely juxtaposed to the target bound by the targeting moiety.

Using chemically conjugated mutants according to the methods of this invention, provides a versatile method of directing a single enzyme to any target simply by changing the chemical moiety. This is a substantial advantage over traditional methods where extensive modification (e.g. by mutagenesis techniques) was required to make a particular target-specific enzyme.

The activity of the enzyme is thus "redirected" in one or both of two ways: First the activity of the enzyme can be "spatially localized" by binding of the targeting moiety to a particular preselected target. Thus, the enzyme may be specifically directed to a particular cell type, a particular enzyme, a particular receptor, etc. Second, by virtue of alterations in the enzyme produced by the presence of the targeting molecule and/or by virtue of the fact that the targeting molecule brings the substrate binding site in close proximity to the target, the enzyme can show significant activity against a target that is not its usual substrate.

The redirected enzymes are useful in a wide variety of contexts. For example, the targeting moiety can be selected to redirect/localize the enzyme to a particular target for selective degradation. For example, in the case of a detergent, the targeting moiety can be selected to specifically bind to a particular class of "soil" (e.g. egg) and thereby direct and appropriate degradative enzyme (e.g. a protease) to that substrate.

In pharmaceutical applications, in some embodiments, the retargeted enzyme can comprise a targeting moiety that directs the enzyme to a particular target cell (e.g. a tumor cell) where the retargeted enzyme (e.g. a thymidine kinase (tk)) activates a particular drug (e.g. a cytotoxin such as ganclovir). In other embodiments the enzyme may be retargeted to a cell that contains an overabundance of a particular metabolite (e.g. as in storage diseases such as Tay Sachs disease). At the new site, the redirected enzyme affords the "missing" enzymatic activity thereby treating the condition. These examples are merely illustrative, and, along with others are discussed in greater detail below.

It will be appreciated in view of the teachings provided herein that catalytic antagonists can be retargeted enzymes, but are not necessarily so. Conversely, retargeted enzymes may act as catalytic antagonists, but there are retargeted enzymes that are not necessarily catalytic antagonists.

In any case, in preferred embodiments, the retargeted enzymes and catalytic antagonists are created by selecting a targeting moiety, selecting an enzyme (an effector moiety) and chemically conjugating the two to form a chimeric molecule.

Selection of targeting moieties, enzymes and conjugating such is described in detail below.

II. Selection of Targets and Targeting Moieties.

In preferred embodiments, virtually any cognate binding partner of a target (e.g. a receptor and/or an enzyme and/or a lectin) can be used as a targeting moiety in the molecules of this invention. In addition, molecules that are not cognate binding partners, but that are specifically bound by the target molecules (e.g. receptors or an enzymes) can also be used as targeting moieties in the chimeric molecules of this invention.

The selection of the targeting moiety depends on the application for which the chimeric molecule (e.g. catalytic antagonist) is to be utilized. Targeting moieties can be grouped and/or identified according to a wide variety of classification schemes. Thus, for example they can be grouped according to type of molecule, e.g. a peptide, an oligopeptide, a peptidomimetic, an antibody, a hapten, an epitope, a carbohydrate, a monosaccharide, an oligosaccharide, a polysaccharide, a glycomimetic, a nucleic acid, a gene, a lipid, a coordination complex, a metal, a sugar, an enzyme, a zymogen, a coenzyme, a cofactor, a coenzyme analog, a cofactor analog, a vitamin, a vitamin analog, a crown ether, a crown ether analog, mono and polycyclic ligands, heterocyclic ligands, chiral ligands, enantiomerically enriched ligands, and any multivalent or dendrimeric variation of the above or, alternatively, they can be grouped according to the nature of the target.

Preferred targets include, but are not limited to receptors, enzymes, and lectins. In some instances it is simple to refer to the targeting moiety that binds to one of these targets. Thus, for example serotonin or a serotonin analogue may be a targeting moiety. Similarly targeting moieties can be referred to/identified by the target to which they bind. Thus a serotonin analogue as targeting moiety is encompassed by a drug or compound that specifically binds to a serotonin receptor.

By way of illustration, some preferred targets in the above categories are discussed below. The described embodiments, however, are illustrative in nature and not intended to be limiting.

A) Targeting Moieties for Receptors.

Receptors provide highly effective targets, particularly for the catalytic antagonists of this invention. Receptors typically specifically bind a cognate ligand and are involved in a wide variety of biological processes. Typically, receptors mediate signaling or the influx or efflux of molecules from a cell. Particularly as transducers of signals, receptors are involved in a wide variety of processes including, but not limited to regulation of growth and morphology/differentiation, gene expression and production of particular molecules, cell proliferation, elements of the immune response, various biological cascades (e.g. the inflammatory response, the clotting response, etc.) and the like.

As a consequence, receptors have long been recognized as good targets for drugs and a wide variety of drugs are agonists and/or antagonists of particular receptor activity (see, e.g., Table 1). Typically these drugs are relatively small organic molecule and, as such, are good candidates as targeting moieties for the chimeric molecules of this invention.

TABLE 1

Typical pharmacological agents and their mode of activity. Such pharmaceuticals make useful targeting moieties to specifically direct a catalytic antagonist of this invention to a target receptor.

| Activity | Drug |
|---|---|
| 5-HT1 Receptor Agonist | Amerge |
| 5-HT2 Receptor Antagonist | Nexopamil (LU 49938) |
| Ca2+ Channel blocker | |
| ACE Inhibitor | Mavik |
| ACE Inhibitor | Prinivil |
| ACE Inhibitor/Diuretic | Accuretic |
| Adjunct in Affective Disorders Management | Alti-Tryptophan |
| Alpha 1A Adrenoceptor Blocker | Flomax |
| Alpha Adrenergic Receptor Agonist (relatively selective) | Alphagan |
| Analgesic | Nu-Mefenamic |
| Analgesic-Antipyretic | Advil |
| Analgesic-Antipyretic | Asaphen E.C. |
| Analgesic-Antipyretic | Motrin (Children's) |
| Analgesic-Antipyretic-Decongestant | Tylenol Decongestant |
| Analgesic-Antitussive | Codeine 15 mg & 30 mg |
| Analgesic-Decongestant-Antihistamine | Sinutab Nightime Extra Strength |
| Androgen | Testosterone Enanthate Injection |
| Androgen | Testosterone Propionate Injection |
| Anesthetic-Sedative | Propofol Injection |
| Angiotensin II AT1 Receptor Blocker | Avapro |
| Angiotensin II AT1 Receptor Blocker | Diovan |
| Angiotensin-converting Enzyme Inhibitor | Captril |
| Antiandrogen | Novo- Cyproterone |
| Antiandrogen-estrogen Combination Hormone | Diane - 35 |
| Antianginal Agent | Nitrolingual Pumpspray |
| Antianginal Agent | pms-Nifedipine |
| Antianginal Agent | Trinipatch 0.2, 0.4 & 0.6 |
| Antiarrhythmic | Nu-Sotalol |
| Antiarrhythmic | Rho-Sotalol |
| Antiarrhythmic | Sotzmol |
| Anticholinergic | Nu-Oxybutyn |
| Anticholinergic-Antispasmodic agent | Gen-Oxybutynin |
| Anticoagulant | Viprinex |
| Anticoagulant-Low Molecular Weight Heparin | Fraxiparine |
| Anticonvulsant | Deproic |
| Anticonvulsant | Novo-Clobazam |
| Anticonvulsant | Nu-Clonazepam |
| Anticonvulsant | Rho-Clonazepam |
| Anticonvulsant | Taro-Carbamazepine CR |
| Antidepressant | Apo-Moclobemide |
| Antidepressant | Effexor XR |
| Antidepressant | Gen-Nortriptyline |
| Antidepressant | Gen-Trazodone |
| Antidepressant | Novo-Nortriptyline |
| Antidepressant | Nu-Desipramine |
| Antidepressant | Nu-Nortriptyline |
| Antidepressant | Wellbutrin SR |
| Antidepressant-Antiobsessional-Antibulimic | Nu-Fluoxetine |
| Antiepileptic Agent | Cerebyx |
| Antihistamine | Benadryl Junior Strength Chewable Tablets |
| Antihistamine-Decongestant | Dimetapp Quick Dissolve |
| Antihistamine-Decongestant | Tavist-D |
| Antihyperglycemic | Nu-Metformin |
| Antihyperglycemic | Rho-Metformin |
| Antihyperlipidemic | Nu-Fenofibrate |
| Antihypertensive | Novo-Terazosin |
| Antihypertensive | Nu-Nifedipine-PA |
| Antihypertensive | Tarka |
| Antihypertensive-Antianginal | Gen-Diltiazem SR |
| Antihypertensive-BPH Treatment | Apo-Terazosin |
| Antihypertensive-BPH Treatment | Nu-Terazosin |
| Antiparkinson | Mirapex |
| Antiparkinson | Nu-Levocarb |
| Antiparkinson | Nu-Selegiline |
| Antiparkinson | Requip |
| Antiparkinson | Tasmar |
| Antipsychotic | Apo-Loxapine |
| Antipsychotic | Nu-Loxapine |
| Antipsychotic | Seroquel |
| Antiretroviral | Zerit |
| Antirheumatic | Ridaura |
| Antispasmodic | Ditropan |
| Antithrombotic | Lovenox |
| Antitussive | Benylin DM 12 Hour |
| Antitussive | Broncho-grippol-DM |
| Anxiolytic | Buspirex |
| Anxiolytic | Bustab |
| Anxiolytic | Gen-Buspirone |
| Anxiolytic | Novo-Poxide |
| Anxiolytic | Nu-Buspirone |
| Anxiolytic-Sedative | Nu-Bromazepam |
| Beta2-adrenergic Stimulant | Airomir |
| Beta2-adrenergic Stimulant | Nu-Salbutamol Solution |
| Beta-adrenergic Blocker | Nu-Acebutolol |
| Beta-adrenergic Blocker | pms-Atenolol |
| Beta-adrenergic Blocker | pms-Metoprolol-L |
| Beta-adrenergic Blocker | Rho-Atenolol |
| Bronchodilator | Gen-Salbutamol Respirator Solution |
| Bronchodilator | Nu-Ipratropium |
| Bronchodilator | Oxeze Turbuhaler |
| Bronchodilator | Quibron-T |
| Calcium Channel Blocker | Chronovera |
| Carbonic Anhydrase Inhibitor | Neptazane |
| Chimeric Monoclonal Antiplatelet Antibody | Reopro |
| Corticosteroid | Flovent Diskus |
| Corticosteroid | Novo-Flunisolide |
| Corticosteroid | Triamcinolone Diacetate Injectable Suspension |
| Diuretic | Demadex |
| Diuretic | Nu-Indapamide |
| Estrogen | Climara |
| Gastrointestinal anti-inflammatory | Salofalk |
| Glucocorticoid | Methylpred nisolone Sodium Succinate for Injection USP |
| Hematinic | Ferodan |
| Hematopoietic | Acti-B12 |
| Hematopoietic | Heracline |
| Histamine H1 Receptor Antagonist | Claritin |
| Histamine H2 Receptor Antagonist | Maalox H2 Acid Controller |

TABLE 1-continued

Typical pharmacological agents and their mode of activity. Such pharmaceuticals make useful targeting moieties to specifically direct a catalytic antagonist of this invention to a target receptor.

| Activity | Drug |
|---|---|
| Histamine H2 Receptor Antagonist | Ulcidine |
| Histamine H2 Receptor Antagonist | Zantac 75 |
| Human Gonadotropin | Pregnyl |
| Human Gonadotropin | Puregon |
| Hypnotic | Gen-Temazepam |
| Hypnotic | Nu-Temazepam |
| Hypnotic | Nu-Zopiclone |
| Hypnotic | pms-Temazepam |
| Hypnotic-Anticonvulsant | Rho-Nitrazepam |
| Hypoglycemic | Euglucon |
| Hypoglycemic | Novo-Gliclazide |
| Hypoglycemic | pms-Glyburide |
| Leukotriene Receptor Antagonist | Accolate |
| Leukotriene Receptor Antagonist | Singulair |
| Lipid Metabolism Regulator | Baycol |
| Lipid Metabolism Regulator | Lescol |
| Muscle Relaxant | Flexitec |
| Muscle Relaxant | Gen-Cycloprine |
| Muscle Relaxant | Liotec |
| Muscle Relaxant | Nu-Cyclobenzaprine |
| Muscle Relaxant-Analgesic | Acetazone Forte |
| Muscle Relaxant-Analgesic | Acetazone Forte C8 |
| Muscle Relaxant-Analgesic | Methoxacet |
| Muscle Relaxant-Analgesic | Methoxacet C1/8 |
| Muscle Relaxant-Analgesic | Methoxisal |
| Muscle Relaxant-Analgesic | Methoxisal-C |
| Neuroleptic | pms-Methotrimeprazine |
| Neuroleptic-Antiemetic | Droperidol Injection |
| Neuromuscular Blocking Agent | Atracurium Besylate Injection |
| Neuromuscular Blocking Agent | Atracurium Besylate Injection |
| Nonsteroidal Anti-inflammatory Drug | Apo-Etodolac |
| Nonsteroidal Anti-inflammatory Drug | Diclotec |
| Nonsteroidal Anti-inflammatory Drug | Fexicam |
| Nonsteroidal Anti-inflammatory Drug | Novo-Ketorolac |
| Nonsteroidal Anti-inflammatory Drug | Nu-Diclo-SR |
| Nonsteroidal Anti-inflammatory Drug | Nu-Ketoprofen-SR |
| Nonsteroidal Anti-inflammatory Drug | Nu-Tiaprofenic |
| Nonsteroidal Anti-inflammatory Drug | pms-Diclofenac |
| Nonsteroidal Anti-inflammatory Drug | Rhodiaprox |
| Opioid Analgesic | Pethidine Injection BP |
| Oral Contraceptive | Alesse 21 and 28 |
| Pediculicide | Para |
| Platelet Aggregation Inhibitor | Apo-Ticlopidine |
| Platelet Aggregation Inhibitor | Nu-Ticlopidine |
| Platelet Aggregation Inhibitor | Plavix |
| Progestogen | Nu-Megestrol |
| Proton Pump Inhibitor | Losec |
| Retinoid | Rejuva-A |
| Selective Estrogen Receptor Modulator | Evista |
| Somatostatin Analogue | Sandostatin |
| Type II Alpha-reducatase Inhibitor | Propecia |
| Upper Gastrointestinal Motility Modifier | Apo-Domperidone |
| Upper Gastrointestinal Motility Modifier | Novo-Domperidone |
| Upper Gastrointestinal Motility Modifier | Nu-Domperidone |
| Upper Gastrointestinal Motility Modifier | pms-Domperidone |
| Vasoactive Agent | Nu-Pentoxifylline-SR |
| Vitamin & Mineral Supplement | Calcium D 500 |
| Vitamin & Mineral Supplement | Caltrate Plus |
| Vitamin & Mineral Supplement | Hemarexin |
| Vitamin Supplement | Hormodausse |
| Vitamin Supplement | Sopalamine/3B |
| Vitamin Supplement | Sopalamine/3B Plus C |

The targeting moiety, however, need not be a known pharmaceutical. There are a number of receptors for which inhibitors or agonists are known where the inhibitors or agonists are not approved pharmaceuticals.

There is, as yet, no uniform classification for receptors. However, as indicated above, a great many receptors are signal transduction receptors and within this group signal-transduction receptors fall into three general classes:

The first class includes receptors that penetrate the plasma membrane and have intrinsic enzymatic activity. Such receptors include, but are not limited to, those that are tyrosine kinases (e.g. PDGF, insulin, EGF and FGF receptors), tyrosine phosphatases (e.g. CD45 [cluster determinant-45] protein of T cells and macrophages), guanylate cyclases (e.g. natriuretic peptide receptors), and serine/threonine kinases (e.g. are cAMP-dependent protein kinase (PKA), protein kinase C (PKC), MAP kinases, activin and TGF-β receptors). Additionally, several families of receptors lack intrinsic enzyme activity, yet are coupled to intracellular tyrosine kinases by direct protein-protein interactions.

The proteins encoding receptor tyrosine kinases (RTKs) typically contain four major domains: an extracellular ligand binding domain, an intracellular tyrosine kinase domain, an intracellular regulatory domain, and a transmembrane domain. The amino acid sequences of the tyrosine kinase domains of RTKs are highly conserved with those of cAMP-dependent protein kinase (PKA) within the ATP binding and substrate binding regions. Some RTKs have an insertion of non-kinase domain amino acids into the kinase domain termed the kinase insert. RTK proteins are classified into families based upon structural features in their extracellular portions (as well as the presence or absence of a kinase insert) which include the cysteine rich domains, immunoglobulin-like domains, leucine-rich domains, Kringle domains, cadherin domains, fibronectin type III repeats, discoidin I-like domains, acidic domains, and EGF-like domains. Based upon the presence of these various extracellular domains the RTKs have been sub-divided into at least 14 different families. Representative RTKs include, but are not limited to I EGF receptor, NEU/HER2, HERS, insulin receptor, IGF-1 receptor, PDGF receptors, c-Kit, FGF receptors, vascular endothelial cell growth factor (VEGF) receptor, hepatocyte growth factor (HGF) and scatter factor (SC) receptors, the neurotrophin receptor family (trkA, trkB, trkC) and NGF receptor, and the like.

The second class includes receptors that are coupled, inside the cell, to GTP-binding and hydrolyzing proteins (termed G-proteins). The G-protein coupled receptors (GPCRs) are a superfamily of integral membrane proteins that are typically characterized by seven hydrophobic domains which are of sufficient length (typically 20-28 amino acid residues) to span the plasma membrane. Examples of this class include, but are not limited to the -adrenergic receptors, odorant receptors and receptors for peptide hormones (e.g. glucagon, angiotensin, vasopressin and bradykinin).

The third class includes receptors that are found intracellularly and that, upon ligand binding, migrate to the nucleus where the ligand-receptor complex directly affects gene transcription. These receptors include, but are not limited to steroid/thyroid hormone receptor superfamily (e.g. glucocorticoid, vitamin D, retinoic acid and thyroid hormone receptors). This is a class of proteins that reside in the cytoplasm and bind the lipophilic steroid/thyroid hormones. Upon binding ligand the hormone-receptor complex translocates to the nucleus and binds to specific DNA sequences termed hormone response elements (HREs). The binding of the complex to an HRE results in altered transcription rates of the associated gene.

Ligands that bind such receptors are well known to those of skill in the art. These include, but are not limited to $A_2$ receptor agonists (see, e.g., U.S. Pat. No. 6,026,317), 5HT1 receptor agonists or antagonists (see, e.g., U.S. Pat. Nos. 6,025,374 and 6,025,367), N-methyl-D-aspartate (NMDA) receptor blockers for the prevention of atherosclerosis (see, e.g., U.S. Pat. No. 6,025,369), modulators of peroxisome proliferator activated receptor-gamma (see, e.g., U.S. Pat. No. 6,022, 897), endothelin receptor antagonists (see, e.g., U.S. Pat. Nos. 6,022,886, 6,020,348), human growth hormone variants having enhanced affinity for human growth hormone receptor at site 1 (see, e.g., U.S. Pat. No. 6,022,711), antagonists of the human neuronal nicotinic acetylcholine receptor (see, e.g, U.S. Pat. No. 6,020,335), platelet GPIIb/IIIa receptor antagonists (see, e.g., U.S. Pat. No. 6,022,523), adenosine receptor agonists (see, e.g., U.S. Pat. No. 6,020,321), interleukin receptor (e.g. IL-2R, IL-4R, IL-6R, IL-8R, IL-10R, IL-13R, etc.) antagonists, binding agents specific for growth factor receptors (e.g. EGF, TGF and analogues or mimetics thereof), binding agents specific for IgA receptor (see, e.g., U.S. Pat. No. 6,018,031), agonists of the strychnine insensitive glycine modulatory site of the N-methyl-D-aspartate receptor complex (see, e.g., U.S. Pat. No. 6,017,957), integrin receptor antagonists (see, e.g., U.S. Pat. No. 6,017,926), androgen receptor modulator compounds (see, e.g., U.S. Pat. No. 6,017,924), PCP receptor ligands (see, e.g., U.S. Pat. No. 6,017,910), azole peptidomimetics as thrombin receptor antagonists (see, e.g., U.S. Pat. No. 6,017,890), NPY Y2-receptor agonists (see, e.g., U.S. Pat. No. 6,017,879), receptor activators of NF-κB (see, e.g., U.S. Pat. No. 6,017,729), antagonists of the TNF receptor, somatostatin receptor-binding agents (see, e.g., U.S. Pat. No. 6,017,509), human histamine $H_2$ receptor, bradykinin binding agents (see, e.g., U.S. Pat. No. 6,015,812), glutamate receptor antagonist (see, e.g., U.S. Pat. No. 6,015,800), imidazoline receptors, transferrin receptors, benzodiazepine receptor binding agents (see, e.g., U.S. Pat. No. 6,015,544), gaba brain receptor ligands (see, e.g., U.S. Pat. No. 6,013,799), neurotensin NT1 and NT2 receptors, CXCR2 receptors, CCR5 receptors, macrophage mannose receptors, and the like.

Other receptors that provide good targets for the chimeric molecules of this invention include but are not limited to, SP-K receptor, substance K receptors, tachykinin 2 receptors, α1-adrenoceptors subtype A, α1-adrenoceptors subtype B, α2-Adrenoceptors subtype A, β1-, β2-, β3-adrenoceptors δ receptors, κ receptors, μ receptors, ACTH receptors, angiotensin receptors, adenosine receptors, bombesin receptors, gastrin-releasing peptide receptors, bradykinin receptors, C5a receptors, Calcitonin gene-related peptide receptors, calcitonin receptors, CCK-A receptors. corticotropin releasing factor receptors, dopamine receptors, EP2 receptors, EP3 receptors, ETA receptors, ETB receptors, FSH receptors, GABA receptors, galanin receptors, glucagon receptors, glucagon-like peptide-1 receptors, gonadotropin receptors, growth hormone-releasing hormone receptors, histamine H1 receptors, histamine H2 receptors, leukotriene B4 receptors, melatonin receptors, MSH receptors, muscarinic M1, M2, M3, and M4 receptors, neurotensin receptors, parathyroid hormone receptors, pituitary adenylate cyclase-activating polypeptide receptors, platelet-activating factor receptors, prostacyclin receptors, P2U purinoceptors, P2Y purinoceptors, rhodopsins, secretin receptors, somatostatin receptors, SSTR receptors, VIP receptors, vasopressin receptors, estrogen receptors, neuropeptide receptors, T-cell receptors, and the like.

B) Targeting Moieties for Enzymes and Antibodies.

In other embodiments, the targeting moieties used in the chimeric molecules of this invention are moieties specifically bound by enzymes or antibodies. A wide variety of enzymes, their substrates and competitive inhibitors thereof are known to those of skill in the art. Moreover, many of these enzymes provide good targets for drug in a wide variety of pathologies.

For example, caspases are a remarkable and intricately regulated network of enzymes that can trigger cell suicide in animals from yeast and worms to humans. Caspases are known to mediate programmed cell death in a number of diseases, including ischemic brain injury, or stroke. It is believed that the cardiac cell death that occurs during heart "attack" is caused by activation of several caspases. In addition, it has been demonstrated administration of an experimental caspase inhibitor known as YVAD-cmk blocks this biochemical cascade and also protects heart tissue, dramatically reducing the amount of myocardial deaths by over 30 percent. Catalytic antagonists of this invention comprising caspase-specific agents as targeting moieties attached to a protease (enzyme) can specifically target and degrade the caspase. It is expected this will offer protection of heart tissue during and after myocardial infarction and brain tissue during and after stroke. Agents that specifically bind to caspases (e.g. YVAD-cmk, and various protected caspase substrates) are known to those of skill in the art.

In another example, the enzyme GARFT (Glycinamide Ribonucleotide Formyl Transferase) is an enzyme in a biochemical pathway through which tumor cells synthesize purines, essential components of DNA. Blocking the action of GARFT inhibits purine synthesis and subsequent tumor DNA molecule construction. With the exception of liver cells, all normal human tissues can obtain purines via an alternative pathway (purine salvage pathway). Inhibitors of GARFT will show selectivity for tumor cells and less significant bone marrow toxicity than other chemotherapeutic agents. A catalytic antagonist of this invention comprising a GARFT targeting moiety attached to a protease capable of degrading GARFT is expected to show similar tumor selectivity. One suitable targeting moiety is AG2037 (produced by Agouron) which is in preclinical studies. AG2037 has been engineered using structure-based design to exhibit potent and selective inhibition of GARFT but to avoid binding to mFBP, a membrane protein believed to be important in the side-effects of earlier GARFT inhibitors. AG2037 is well tolerated in a variety of mouse cancer models and demonstrates broad-spectrum antitumor efficacy, at least equal to that of paclitaxel when studied in the same tumors grown in mice.

In still another example, the intracellular enzyme, dihydroorotate dehydrogenase (DHODH) provides a good target. DHODH is the fourth sequential enzyme involved in the de novo biosynthesis of uridylate (UMP). Since activated T cells require rapid de novo pyrimidine biosynthesis, this enzyme is known to be critical for the activation of the immune response, making it a good target for intervention in transplantation and autoimmune disease. One compound that targets this enzyme, Leflunomide (Hoechst), has been approved by the U.S. Food and Drug Administration (FDA) for the treatment of active rheumatoid arthritis in adults leflunomide, or related DHODH-specific agents can be used as a targeting moiety attached to an enzyme that degrades the DHODH enzyme and provides a similar therapeutic result. Another known inhibitor, Brequinar sodium, has shown efficacy in many animal models of immunosuppression, but was not successful in clinical trials for transplantation, apparently due to a narrow therapeutic window. When used as a targeting moiety in a catalytic antagonist of this invention, it is expected that the therapeutic window will be improved because the molecule will be effective in lower dosages. In general, it is believed that conversion of drugs that act as competitive inhibitors into catalytic antagonists in accordance with this invention will show an improved therapeutic window due to their higher efficacy at lower concentration.

In still yet another example, the catalytic antagonists of this invention are useful in the treatment of hereditary emphysema. The inherited form of emphysema is called alpha-1 proteinase inhibitor deficiency or "alpha-one" for short. People with this disease have a deficiency in a major protein, alpha-1 proteinase inhibitor. Alpha-1 proteinase inhibitor is a major protein in the blood and is produced primarily in the liver cells but also by some white blood cells. It protects the lung by blocking the effects of powerful enzymes called elastases. Elastase is normally carried in white blood cells and protects the delicate tissue of the lung by killing bacteria and neutralizing tiny particles inhaled into the lung. Once the protective work of this enzyme is finished, further action is blocked by the alpha-1 proteinase inhibitor. Without alpha-1 proteinase inhibitor, elastase can destroy the air sacs of the lung.

Thus, catalytic antagonists of this invention comprising an alpha-1 proteinase binding moiety attached (e.g. the drug called Prolastin) to, e.g. a protease, will degrade alpha-1 proteinase affording similar or better therapeutic benefit.

Antibodies also provide useful targets for the catalytic antagonists of this invention. Thus, for example, a catalytic antagonist that targets and antagonizes (e.g. degrades) α-Gal epitope specific antibodies is expected to significantly reduce an immune response (e.g. to a xenotransplant). In one embodiment, then, the α-Gal epitope can be used as a targeting moiety in a chimera of this invention. It may be attached to a protease (e.g. a subtilisin, a pepsin, etc.) and when it is bound by the antibody it will degrade that antibody thereby inhibiting the antibody-mediated immune response.

Similarly particularly where the xenotransplant is from a different species, the catalytic antagonist can use as a targeting moiety the MHC (or component thereof) of the xenotransplant. If the enzymatic component is a hydrolase (e.g. a protease), the catalytic inhibitor will specifically digest the receptor on effector cells of the immune system (e.g. cytotoxic T lymphocytes (CTLs) only on those cells specifically directed against the xenotransplant. The catalytic antagonists will thus confer specific tolerance to the xenograft without generally compromising the host immune system.

Other antibodies that are good targets for the catalytic inhibitors of this invention are antibodies produced in autoimmune responses and/or other allergic responses. In these instances, the targeting moiety is a molecule bearing an epitope recognized by the antibodies mediating the autoimmune or allergic response. Degradation of the antibody by, e.g. a hydrolase attached to the targeting moiety will reduce the pathologic symptoms associated with the autoimmune response. Specific allergens and substrates recognized by antibodies in various autoimmune responses are well known to those of skill in the art and can readily incorporated into the chimeric molecules of this invention.

While many of the illustrations provided above are directed to in vivo applications, the invention is not so limited. It is well recognized that it is desirable to inhibit enzymes and/or antibodies in a wide variety of ex vivo applications. These include, but are not limited to various cell cultures, bioreactors or fermentation systems, or various ex vivo synthetic processes (e.g. laboratory processes and/or commercial processes), antimicrobials/disinfectants, and the like.

C) Targeting Moieties for Lectins and Sugars.

In still other embodiments, targeting moieties are selected that bind to particular lectins. Lectins are proteins obtained from many plant, animal, and bacterial sources that have binding sites for specific mono or oligosaccharides. Lectins such as concanavalin A and wheat germ agglutinin are widely used as analytical and preparative agents in the study of glycoproteins.

Lectins are also present on the surfaces of eukaryotic and bacterial cells. In eukaryotic cells, lectins are often involved in cell-cell interactions. In bacterial cells, lectins often mediate adhesion of the bacterium to its target/host and, in many cases, such adhesion is required for the bacterium to infect the host cell.

In addition, bacterial adhesion and contamination of non-biological surfaces are serious problems in the medical, dental and food science fields. The most detrimental effects are encountered in medicine, where the failure of implanted or transdermal medical devices primarily results from surface-associated bacterial infections. Bacterial interaction/adhesion to a surface is often mediated by lectins (often referred to as adhesins). Bacteria adhering onto a surface frequently secrete an exopolysaccharide matrix in order to cement themselves to the surface. This slimy layer of bacteria embedded in a polysaccharide matrix is known as a biofilm. At the present time, there is no cure for biofilm infections in vivo because the bacteria are resistant to any anti-microbial or antibiotic treatment.

Biofilm formation is also problematic in a wide variety of commercial synthetic systems. Often fermentation vessels and other bioreactors are contaminated by biofilms. Biofilms also growing in and contaminate apparatus used for many chemical processes particularly those involving "digestible" organic reagents. Thus, biofilms often contaminate filters, conduits, separators and other devices.

In certain embodiments, the catalytic antagonists of this invention can be used to inhibit/degrade various lectins. Thus, for example, a catalytic antagonist comprising a sugar or oligosaccharide attached to a hydrolase will specifically target and degrade a lectin that binds the target molecule. Such a catalytic antagonist is illustrated in the examples.

Degradation of lectins/adhesins on a bacterial surface will interfere with the bacteria's ability to bind to a surface and thereby prevent the bacterium from entering a host cell or from forming a biofilm.

In a related embodiment, it is known that many bacteria and bacterial toxins bind to ganglioside, an acid glycosphingolipid and invade host cells. The best known of these is the cholera toxin, an enterotoxin produced by *Vibrio cholerae*, which is known to bind ganglioside GM1. Other ganglioside-binding bacterial toxins include Tetanus toxin (GD1b), botulinum toxins (GT1b and GQ1b) and delta toxin produced by *Clostridium perfringens* (GM2). Shiga toxin produced by *Shigella dysenteriae* and Vero toxin produced by enterohaemorrhagic *E. coli* bind to neutral glycosphingolipids having an alpha-1,4 galabiose moiety in the sugar chain, such as galabioside (Ga2Cer) and ceramide trihexoside (Gb3 Cer).

Many pathogenic bacteria also bind to glycosphingolipids of host cell surface for colonization and infection. Thus, uropathogenic *E. coli* which cause urinary tract infections can bind to glycosphingolipids having an alpha-1,4 galabiose moiety at the non-reducing end of the sugar chain (Gb3Cer, etc). Uropathogenic *E. coli* can also bind to globoside (Gb4Cer) and Forssman glycolipid, both of which have an alpha-1,4 galabiose moiety internally in a sugar chain. *E. coli* binds to glycosphingolipids by pili that exist on the bacterial cell surface and are similar to fibers or hairs. On the top of pili, there is an adhesin characterized as a lectin. Several types of adhesin, with respect to their sugar specificity, have been identified. They are the type I adhesin of *E. coli* that are mannose specific, type P adhesin, also of *E. coli*, specific for alpha-1,4 galabiose moiety, and type S adhesin of *E. coli*, specific for sialylgalactose moiety. It was reported that the amino acid sequence of P-adhesin is similar as that of Shiga toxin because both recognize alpha-1,4 galabiose moiety of glycosphingolipid. *Propionibacterium*, which causes skin disease, recognizes the lactosyl moiety of glycosphingolipids as a binding epitope. These bacteria can bind strongly to lactosylceramide and also bind to isoreceptors such as asialo GM1 (GA1) and asialo GM2 (GA2). Because almost all glycosphingolipids contain a common lactosyl moiety, *Propionibacterium* may be assumed to bind almost all glycosphingolipids. However, the bacteria cannot bind to any, glycosphingolipids composed of a dihydroxy base and nonhydroxy fatty acid in ceramide, even though these contain a lactosyl moiety. This fact indicates that the binding epitope of the bacteria also depends on the ceramide structure in addition to the lactosyl moiety in sugar chain. *Neisseria gonorrhoeae*, which cause gonorrhoea, also bind glycosphingolipids having a lactosyl moiety.

In view of the foregoing, catalytic antagonists having targeting moieties that specifically bind various glycosphingolipids and/or various adhesins (e.g. mannose specific type I adhesin of *E. coli*, alpha-1,4 galabiose specific type P adhesin of *E. coli*, and sialylgalactose type S adhesin of *E. coli*) attached to enzymes that degrade the glycosphingolipids (e.g. glycosidases, cerebrosidases, etc.) will act to prevent bacterial infections and are expected to provide effective therapeutics to block acute effects of bacterial-produced toxins (e.g. cholera toxin).

Lectins, particularly membrane glycoproteins, are also implicated in various inflammatory processes (e.g. inflammatory processes associated with rheumatoid arthritis, arthritis, septic shock, myocardial infarction, etc.). For example Lec-CAMs or selectins are expressed on the surfaces of endothelium, leukocytes and platelets and influence leukocyte-endothelial adhesion at sites of inflammation. GMP-140 (P-selectin) stored in Weibel-Palade bodies of endothelial cells and a platelet granules, when stimulated by TNF-α/IL-1 is transported within minutes to the cell surface and participates in interactions between endothelium, platelets, neutrophils. ELAM-1 (E-selectin) is synthesized de novo by stimulated endothelium e.g. by TNF-α/IL-1, and enhances later recruitment of leukocytes. LAM-1 (L-selectin) regulates lymphocyte binding to high endothelial lymph node venules, the surface of neutrophils and lymphocytes to localize these cells to injury.

In addition, the integrins, a family of adhesion molecules composed of heterodimers of α and β subunits; act in regulation of cell-matrix and cell-cell adhesion. These molecules are transmembrane in structure, thus linking or "integrating" exterior/surface stimuli to the internal cell cytoskeleton. β2 integrins: also known as CD11/CD18 molecules confer adhesion specificity, mediate activation of phagocytic cells by chemotactic stimuli.

The surface expression of integrins e.g. MO-1, leukocyte function antigen-1 (LFA-1) and gp150,95; assist in localization of phagocytes to injury sites; deficiency states result in enhanced susceptibility to bacterial infection.

The intercellular adhesion molecule-1 (ICAM-1): assists in localization of leukocytes to tissue injury; expressed on surface of cytokine stimulated endothelium and leukocytes; binds to LFA-1 and MO-1 present on cell membranes of neutrophils and macrophages. The vascular cell adhesion molecule-1 (VCAM-1): binds VLA-4 leukocyte receptor on lymphocytes, monocytes, eosinophils, basophils.

All of these molecules also offer suitable targets for the catalytic antagonists of this invention. The forgoing illustrations of lectin-directed catalytic antagonists of this invention are intended to be illustrative and not limiting. Numerous other lectin targets will be known to those of skill in the art.

It will be appreciated that the target and targeting moieties described herein (and others) can be reversed. Thus, instead of a sugar, the targeting moiety can be a lectin that will specifically direct the catalytic antagonist (or redirected enzyme) to a sugar or sugar-bearing target. Thus, the molecules can be directed to the sugars present on and characteristic of particular bacteria. In one embodiment, the sugar-targeted catalytic antagonist will make an effective-microbicide.

As indicated above, such molecules can be targeted by using simple sugars, or oligosaccharides and the like as targeting moieties in the chimeric molecules of this invention. In addition, dendrimers can also be used as targeting moieties. Thus, multiple functionalization of the enzyme (e.g. either a catalytic antagonist or a redirected enzyme) can be achieved using dendrimeric targeting moieties whereby multiple branched linking structures can be employed to create a polyfunctionalized enzyme (chimeric molecule).

For instance, multiple glycosylation, including multiple mannose-containing chimeras and varied sugar moieties can be created. This could confer the benefit of increased affinity for, and increased binding affinity between, lectins and the targeted enzyme (e.g. a hydrolase). This would also permit multiple concurrent targeting of sites, for instance by incorporating multiple biotin molecules into a targeting moiety that would elicit multiple concurrent biotin-avidin interactions. The dendrimer targeting moieties (before coupling to the enzyme) would preferably include methanethiosulfonates with simple branching such as:

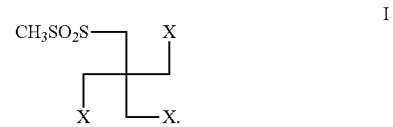

I derived from pentaerythritol, to very complex branched dendrimer reagents as illustrated in FIG. 1. Highly branched molecules or dendrimers were first synthesized by Vogtle in 1978 (Buhleier et al (1978) *Synthesis,* 178). The attachment of identical building blocks that contain branching sites to a central core may be achieved with a high degree of homogeneity and control Each branch contains a functional group which, after chemical alteration, may be connected to yet another branching building block. In this manner, layer after layer of branching rapidly generates highly functionalized molecules (Bosman et al (1999) *Chem. Rev.,* 99: 1665-1688).

D) Targeting Other "Miscellaneous Ligands.

Using the teaching provided herein, a wide variety of other moieties for targeting by the chimeric molecules of this invention will be apparent to those of skill in the art. For example, the redirected enzymes describe herein can be used in a variety of drug delivery strategies. The targeting moiety can be directed to specifically bind to a particular cell type or tissue (e.g. a tumor cell). The enzymatic component can be selected for an activity that converts a (e.g. non-toxic prodrug) to an active form (e.g. a cytotoxin). The retargeted enzyme of this invention thus localizes the activity of the prodrug/drug to the cells bound by the chimeric molecule. Numerous cell-specific markers are known to those of skill in the art. These include, but are not limited to the LewisY antigen (tumor cells), the G250 antigen (renal cell carcinoma cells), the IL-13 receptor (tumor cells) and the like. One example of a suitable enzyme for use in this application is a thymidine kinase (e.g., Herpes simplex thymidine kinase (HSVTK) or *Varicella zoster* thymidine kinase (VZVTK)). thymidine kinase assists in metabolizing antiviral nucleoside analogues to their active form are therefore useful in activating nucleoside analogue precursors (e.g., AZT or ddC) into their active form. In addition, tk-containing cells are killed when contacted with ganclovir.

Thus, in one embodiment, the redirected enzyme of this invention can be a thymidine kinase targeted, for example to a cell expressing a CCR5 and/or a CCR3 receptor (and hence likely to be susceptible to HIV infection). The tk re-directed to these cells can activate AZT or ddC precursors into their active form.

In another embodiment, the tk enzyme can be directed to a tumor cell (e.g. via a tumor specific antigen). Treatment with ganclovir then results in death of the tumor cell.

Other examples of prodrugs that can be converted to their active form using the redirected enzymes of this invention include, but are not limited to prodrugs of 5-FU or inhibitors of dihydropyrimidine dehydrogenase (DPD) (GW 776C85).

Still another example is the prodrug phosphenyloin, a relatively soluble prodrug that is converted by phosphatase to relatively insoluble phenyloin an active anticonvulsant. Similarly, depivefrin is converted by esterase to epinephrine, an adrenergic, useful in the treatment of glaucoma.

The re-directed enzymes of this invention can also act as "self-protected" polypeptides particularly when utilized as in vivo therapeutics. In such an embodiment, the organic molecule (e.g. the targeting moiety) component of the chimeric molecule can sterically shield and protect the effector (enzyme) component of the chimeric molecule. The idea of this is that bulky groups attached near to key positions on the chimeric molecule would hinder the attack of another reagent on, e.g. cleavage sites in the remainder of the chimera and therefore prolong its lifetime. For example, sugars on proteins increase their stability to proteinases, i.e., the proteinase can't get in to cleave its preferred amide bond because a sugar is blocking it (see, e.g., Rudd et al. (1994) *Biochemistry*, 33: 17-22). In certain embodiments, the organic molecule can perform "double duty" providing both a targeting functionality as well as a protective function.

In still another embodiment, the re-directed enzymes of this invention can be utilized in enzyme replacement therapy, particular in the treatment of storage diseases. Storage diseases are caused by the increased accumulation of metabolic products (e.g., lipids, proteins, and complex carbohydrates) due to either the inactivity of an enzyme that degrades the products or the hyperactivity of an enzyme that creates the products. Storage disease include but are not limited to glycogen storage disease I, GM1 gangliosidoses, MPS IV B (Morquio B), GM2 gangliosidoses (O, B, AB, B1 variants), Niemann-Pick disease (A, B, and C), Metachromatic leukodystrophy (arylsulfatase A and SAP-1 deficient), Krabbe disease, Fabry disease, Gaucher disease, Farber disease, Wolman disease (cholesterol ester storage disease), MPS I (Hurler and Scheie syndromes), MPS II (Hunter syndrome), MPS III A, C, and D (Sanfilippo A, C, and D), PS III B (Sanfilippo B), MPS IV A (Morquio A), MPS VI (Maroteaux-Lamy syndrome), MPS VII (beta-glucuronidase deficiency), Multiple sulfatase deficiency, Mucolipidosis I (Sialidosis), Mucolipidosis II & III, alpha-Mannosidosis, beta-Mannosidosis, Fucosidosis, Sialic acid storage disease, Galactosialidosis, Aspartylglucosaminuria Cystinosis. Storage diseases can be treated by supplementing the "missing" enzymatic activity.

For example, Gaucher's disease can be treated by use of a glucocerebrosidase targeted to spleen cells. Similarly, superoxide dismutase can be targeted to the liver as an anti-oxidant, and so forth.

III. Selection of Enzymes (Effector Molecules).

Virtually any enzyme can be utilized in the chimeric molecules of this invention. Where the chimeric molecule is a catalytic antagonist, enzymes are selected that are capable of degrading the substrate specifically bound by the targeting moiety. Such enzymes include, but are not limited to proteases, cellulases, nucleases (exo- and endo-), amylases, lipases, aldolases, ketolases, glycosidases, and the like.

Where the chimeric molecule is an enzyme whose activity is directed to a new location and/or substrate, the enzyme can be, but need not necessarily be an enzyme that degrades its substrate. Thus, in addition to proteases, cellulases, nucleases (exo- and endo-), amylases, lipases, aldolases, ketolases, glycosidases, and the like, the redirected enzymes can also include enzymes such as isomerases, oxidases, oxidoreductases, ligases, transferases, and the like.

Preferred enzymes for use in the catalytic antagonists of this invention are the hydrolases. Particularly preferred enzymes for use in the catalytic antagonists of this invention are the serine hydrolases. The serine hydrolases are a class of hydrolytic enzymes characterized by a hydrolytic enzymes that posses a catalytic triad composed of a serine, histidine and a carboxylate amino acid (either aspartic or glutamic acid), and which catalyze the hydrolysis, and microscopic reverse reactions thereof, of carboxylic acid derivatives including, but not restricted to, esters, peptides and amides.

Preferred serine hydrolases comprising this invention include the trypsin-chymotrypsin proteases, the subtilisin proteases, and the alpha/beta hydrolases. In a particularly preferred embodiment the enzyme is protease, more preferably a subtilisin (e.g. a *Bacillus lentis* subtilisin). Subtilisin is a serine endoprotease (MW ~27,500) which is secreted in large amounts from a wide variety of *Bacillus* species. The protein sequence of subtilisin has been determined from at least four different species of *Bacillus* (see, e.g., Markland et al. (1971) pages 561-608 In: *The Enzymes*, ed. Boyer P. D., Acad Press, New York, Vol. III, pp.; Nedkov et al. (1983) *Hoppe-Seyler's Z. Physiol. Chem.* 364: 1537-1540). The three-dimensional crystallographic structure of subtilisin BPN' (from *B. amyloligoefaciens*) to 2.5 Å resolution has also been reported (Wright et al. (1969) Nature 221, 235-242; Drenth et al. (1972) *Eur. J. Biochem.* 26: 177-181. These studies indicate that although subtilisin is genetically unrelated to the mammalian serine proteases, it has a similar active site structure. The x-ray crystal structures of subtilisin containing covalently bound peptide inhibitors (Robertus, et al. (1972) *Biochemistry* 11: 2439-2449), product complexes (Robertus et al. (1972) *Biochemistry* 11: 4293-4303), and transition state analogs (Matthews et al (1975) *J. Biol. Chem.* 250: 7120-7126; Poulos et al. (1976) *J. Biol. Chem.* 251, 1097-1103), which have been reported have also provided information regarding the active site and putative substrate binding cleft of subtilisin. In addition, a large number of kinetic and chemical modification studies have been reported for subtilisin (Philipp et al. (1983) *Mol. Cell. Biochem.* 51:5-32; Svendsen (1976) *Carlsbera Res. Comm.* 41: 237-291; Markland, Id.) as well as at least one report wherein the side chain of methionine at residue 222 of subtilisin was converted by hydrogen peroxide to methionine-sulfoxide (Stauffer et al. (1965) *J. Biol. Chem.* 244: 5333-5338).

Other particularly preferred hydrolases for use in this invention include, but are not limited to α/β hydrolases, trypsin/chymotrypsin families of serine hydrolase enzymes, aspartyl proteases, cysteine proteases, metalloproteases, lysozymes and other glycosidases etc.

IV. Construction of Chimeric Molecules.

In preferred embodiments, the chimeric catalytic antagonists and/or redirected enzymes of this invention are made by chemically conjugating the desired enzyme (directly or through a linker) to the targeting moiety. While many strategies are known for preparing chemically conjugated chimeric molecules (see, e.g., European Patent Application No. 188,256; U.S. Pat. Nos. 4,671,958, 4,659,839, 4,414,148, 4,699,784; 4,680,338; 4,569,789; 4,589,071; 4,545,985 and 4,894,443; Borlinghaus et al. (1987) *Cancer Res.* 47: 4071-4075; Thorpe et al. (1991) *Monoclonal Antibody-Toxin Conjugates: Aiming the Magic Bullet*, Thorpe et al., (1982) *Monoclonal Antibodies in Clinical Medicine*, Academic Press, pp. 168-190; Waldmann (1991) *Science,* 252: 1657, and the like), in a preferred embodiment, the targeting moiety is derivatized/functionalized with a reactive group that can react with an available R group (e.g. $NH_2$, N, NH, OH, COOH, SH, etc.) on an amino acid residue comprising the enzyme. In particularly preferred embodiments, the targeting moiety is derivatized as a methanethiosulfonate reagent that can then react with the —SH in a cysteine to provide the targeting moiety coupled in place of the thiol hydrogen on the cysteine. The coupling can be direct or through a linker.

In certain embodiments, the cysteine to which the targeting moiety is attached is a native cysteine in the enzyme, however, in preferred embodiments the cysteine is a cysteine substituted for a different native amino acid residue in the enzyme. The enzyme so modified is, optionally, referred to as a mutant enzyme. Chimeric molecules of this invention in which the targeting molecule is chemically coupled to a mutant enzyme are, optionally, referred to as Chemically Modified Mutants (CMMs).

Typically, once the targeting moiety and the enzyme that are to be coupled are selected, e.g., as described above, the location (residue) in the enzyme for attachment of the targeting moiety is identified. Where this residue is not already a cysteine, a cysteine is substituted for the native residue. The targeting moiety, or a linker attached thereto, is derivatized as a methanethiosulfonate which can then be reacted with the cysteines —SH group as described herein. Detailed protocols for the preparation of mutant enzymes and, the coupling of a targeting moiety are provided below and in the examples.

A) Production of Mutant Enzymes for Chemical Modification.

1) Selection of Residues for Modification.

In general, virtually any residue of the enzyme can be selected for mutagenesis (e.g. substitution of a cysteine) and chemical modification to introduce a targeting moiety, as long as the modification retains the desired level of activity of the subject enzyme. Typically this is accomplished by making the substitution at a location that does not block critical substrate interactions or drastically alter folding/conformation of the subject enzyme.

Suitable sites for introduction of a targeting moiety can be determined by substituting cysteine, and optionally an attached targeting moiety, and assaying the enzymes for the desired activity. With the current advances in combinatorial chemistry and high throughput screening systems such modifications and screening can be accomplished with only routine experimentation.

In a preferred embodiment, however, residues for modification/substitution in the enzyme (e.g. serine hydrolase) are rationally selected. Preferred sites include sites not in critical conformation determining regions and sites disposed away from the subsite(s) of the enzyme. However, in other preferred embodiments, particularly where it is desired to enhance, or otherwise alter, substrate specificity and/or activity, preferred amino acid residues selected for modification include residues expected to be important discriminatory sites near, adjacent to or within the substrate binding region of the enzyme. Such residues are determined from mutagenesis experiments where the subsite residues are systematically mutagenized and the effect of such mutagenesis on binding specificity and/or enzymatic activity is determined. In addition, important residues can be identified from inspection of crystal structures of the enzyme alone or in complex with substrate, substrate analogues or inhibitors and/or from predicted protein folding or protein-protein interactions determined using protein modeling software (e.g., Quanta, Cerius, Insight (Molecular Simulations Inc.) and Frodo (academic software). Side chains situated to alter interaction at subsites defined by Berger and Schechter can be selected based on the crystallographic models of the enzymes and extrapolated to homologous enzymes if necessary if structural information on a specific enzyme is unavailable. In *B. lentus* subtilisin sites 62, 156, 166, 217 and 222 are important substrate specificity determining sites. Additional related sites include position 96, 104, 107, 189 and 209 in subtilisin and homologous positions in related enzymes. In preferred embodiments, such residues typically lie in the S1, S2, S4, S1', S2', or S3' subsites although it will be appreciated that in certain cases, alteration of residues in other subsites can also produce dramatic effects.

In one particularly preferred embodiment, where the serine hydrolase is a subtilisin-type serine hydrolase, preferred residues for mutation include, but are not limited to residues at or near residues 156 and 166 in the S1 subsite, residues 217 and 222 in the S1' subsite, residue 62 in the S2 subsite, and Leu96, Val104, Ile107, Phe189 and Tyr209 or residues at or near homologous positions other subtilisin-type serine proteases (preferably positions within subsites).

In another preferred embodiment, where the serine hydrolase is a trypsin-chymotrypsin type serine hydrolase, preferred residues for mutation include, but are not limited to, residues at or near residues Tyr94, Leu99, Gln175, Asp189, Ser190, Gln192, Leu111, Phe175, Tyr176, Ser182, Leu184, Phe189, Tyr214, Asp231, Lys234, and Ile243 of trypsin (Protein Databank Entry 1TPP) or residues at or near homologous positions of other chymotrypsin-type (trypsin-chymotrypsin-type) serine proteases (preferably positions within subsites).

In still another preferred embodiment, where the serine hydrolase is an alpha/beta serine hydrolase, preferred residues for mutation include, but are not limited to, residues at or near the following residues: Trp104, Thr138, Leu144, Val154, Ile189, Ala 225, Leu278 and Ile185, where these are residues of *Candida antartica* lipase (Protein Data Bank entry 1tca) or residues at homologous positions of other alpha/beta type serine hydrolases (preferably positions within subsites).

Preferably the amino acids replaced in the enzyme by cysteines are selected from the group consisting of asparagine, leucine, methionine, or serine. More preferably the amino acid to be replaced is located in or near a subsite of the enzyme preferably the S1, S1', or S2 subsites. More preferably, in a subtilisin the amino acids to be replaced are N62, L217, M222, S156, S166, site 104, site 107 (S4), site 96 (S2), site 189(S2'), and site 209 (S1'/S3') or their homologues where the numbered position corresponds to naturally occurring subtilisin from *Bacillus amyloliquefaciens* or to equivalent amino acid residues in other subtilisins such as *Bacillus lentus* subtilisin.

The chimeric molecules of this invention are not limited to serine hydrolases. In addition to other enzymes, in particularly preferred embodiments, this invention includes other chimeric proteases. Such proteases include, but are not limited to aspartyl proteases, cysteine proteases, metalloproteases, and the like.

Where the protease is aspartyl protease such as pepsin, preferred residues for mutation include, but are not limited to, amino acid(s) corresponding (e.g. at a homologous position) to a residue at or near the following residues Tyr9, Met12, Gln13, Gly76, Thr77, Phe111, Phe117, Ser127, Ile 128, Ser130, Tyr189, Ile213, Glu239, Met245, Gln 287, Met 289, Asn290, Leu291, and Glu294, where these "reference" residues are residues in the mature human pepsin (Protein Data Bank entry 1PSN).

Where the protease is cysteine protease, preferred residues for mutation include, but are not limited to, amino acid(s) corresponding (e.g. at a homologous position) to a residue at or near the following residues Asn18, Ser21, Asn64, Tyr67, Trp69, Gln112, Gln142, Asp158, Trp177, and Phe207, where these reference residues are residues in the mature papain (Protein Data Bank entry 1BQI).

Where the protease is metalloprotease, preferred residues for mutation include, but are not limited to, amino acid(s) corresponding (e.g. at a homologous position) to a residue at or near the following residues Leu111, Phe175, Tyr176, Sen 82, Leu184, Phe189, Tyr214, Asp231, Lys234, and Ile243, where these reference residues are residues in the mature human matrix metalloprotease (Protein Data Bank entry 830C).

2) Introduction of Cysteine.

The substitution of a cysteine for one or more native residue(s) in the enzyme (e.g. serine hydrolase) can be accomplished using routine methods well known to those of ordinary skill in the art. In one preferred embodiment, the mutants described herein are most efficiently prepared by site-directed mutagenesis of the DNA encoding the wild-type enzyme of interest (e.g. *Bacillus lentis* subtilisin). Techniques for performing site-directed mutagenesis or non-random mutagenesis are known in the art. Such methods include, but are not limited to alanine scanning mutagenesis (Cunningham and Wells (1989) *Science,* 244, 1081-1085), oligonucleotide-mediated mutagenesis (Adellman et al. (1983) DNA, 2, 183), cassette mutagenesis (Wells et al. (1985) *Gene,* 344: 315) and binding mutagenesis (Ladner et al. WO 88/06630).

In one embodiment of the present invention, the substitute amino acid residue (e.g. cysteine) is introduced into the selected position by oligonucleotide-mediated mutagenesis using the polymerase chain reaction technique. In this approach, the gene encoding the desired native enzyme (e.g. subtilisin) is carried by a suitable plasmid. More preferably, the plasmid is an expression vector, e.g., a plasmid from the pBR, pUC, pUB, pET or pHY4 series. The plasmid can be chosen by persons skilled in the art for convenience or as desired.

For site-directed mutagenesis, the fragment containing the selected mutation site is cleaved from the gene encoding the subject enzyme by restriction endonucleases and is used as the template in a modified PCR technique (see, Higuchi et al. (1988) *Nucleic Acid Res.,* 16, 7351-7367). For each target substitution, an oligonucleotide containing the desired mutation is used as a mismatch primer to initiate chain extension between 5' and 3 PCR flanking primers. The process includes two PCR reactions. In the first PCR, the mismatch primer and the 5' primer are used to generate a DNA fragment containing the desired base substitution. The fragment is separated from the primers by electrophoresis. After purification, it is then used as the new 5' primer in a second PCR with the 3' primer to generate the complete fragment containing the desired base substitution. After confirmation of the mutation by sequencing, the mutant fragment is then inserted back to the position of the original fragment.

In another approach, a cassette mutagenesis method may be used to facilitate the construction and identification of the cysteine mutants of the present invention. First, the gene encoding the serine hydrolase is obtained and sequenced in whole or in part. Then the point(s) at which it is desired to make a mutation of one or more amino acids in the expressed enzymes is identified. The sequences flanking these points are evaluated for the presence of restriction sites for replacing a short segment of the gene with an oligonucleotide which when expressed will encode the desired mutants. Such restriction sites are preferably unique sites within the serine hydrolase gene so as to facilitate the replacement of the gene segment. However, any convenient restriction site which is not overly redundant in the hydrolase gene may be used, provided the gene fragments generated by restriction digestion can be reassembled in proper sequence. If restriction sites are not present at locations within a convenient distance from the selected point (e.g., from 10 to 15 nucleotides), such sites are generated by substituting nucleotides in the gene in such a fashion that neither the reading frame nor the amino acids encoded are changed in the final construction. The task of locating suitable flanking regions and evaluating the needed changes to arrive at two convenient restriction site sequences is made routine by the redundancy of the genetic code, a restriction enzyme map of the gene and the large number of different restriction enzymes. If convenient flanking restriction site is available, the above method need be used only in connection with the flanking region which does not contain a site.

Mutation of the gene in order to change its sequence to conform to the desired sequence is accomplished e.g., M13 primer extension in accord with generally known methods. Once the gene is cloned, the restriction sites flanking the sequence to be mutated are digested with the cognate restriction enzymes and the end termini-complementary oligonucleotide cassette(s) are ligated into the gene. The mutagenesis is enormously simplified by this method because all of the oligonucleotides can be synthesized so as to have the same restriction sites, and no synthetic linkers are necessary to create the restriction sites.

A suitable DNA sequence computer search program simplifies the task of finding potential 5' and 3' convenient flanking sites. In preferred embodiments, any mutation introduced in creation of the restriction site(s) are silent to the final construction amino acid coding sequence. For a candidate restriction site 5' to the target codon a sequence preferably exists in the gene that contains at least all the nucleotides but for one in the recognition sequence 5' to the cut of the candidate enzyme. For example, the blunt cutting enzyme SmaI (CCC/GGG) would be a good 5' candidate if a nearby 5' sequence contained NCC, CNC, or CCN. Furthermore, if N needs to be altered to C this alteration preferably leaves the amino acid coding sequence intact. In cases where a permanent silent mutation is necessary to introduce a restriction site one may want to avoid the introduction of a rarely used codon. A similar situation of SmaI would apply for 3' flanking sites except the sequence NGG, GNG, or GGN must exist. The criteria for locating candidate enzymes are most relaxed for blunt cutting enzymes and most stringent for 4 base overhang enzymes. In general many candidate sites are available.

A particularly preferred of method of introducing cysteine mutants into the enzyme of interest is illustrated with respect to the subtilisin gene from *Bacillus lentus* ("SBL"). In a preferred embodiment, the gene for SBL is cloned into a bacteriophage vector (e.g. M13 mp19 vector) for mutagenesis (see, e.g. U.S. Pat. No. 5,185,258). Oligonucleotide-directed mutagenesis is performed according to the method described by Zoller et al. (1983) *Meth. Enzymol.*, 100: 468-500. The mutated sequence is then cloned, excised, and reintroduced into an expression plasmid (e.g. plasmid GG274) in the *B. subtilis* host. PEG (50%) is added as a stabilizer.

The crude protein concentrate thus obtained is purified by first passing through a Sephadex™ G-25 desalting matrix with a pH 5.2 buffer (e.g. 20 mM sodium acetate, 5 mM $CaCl_2$) to remove small molecular weight contaminants. Pooled fractions from the desalting column are then applied to a strong cation exchange column (e.g. SP Sepharose™ FF) in the sodium acetate buffer described above and the SBL is eluted with a one step gradient of 0-200 mM NaCl acetate buffer, pH 5.2. Salt-free enzyme powder is obtained following dialysis of the eluent against Millipore purified water and subsequent lyophilization.

The purity of the mutant and wild-type enzymes, which are denatured by incubation with a 0.1 M HCl at 0° C. for 30 minutes is ascertained by SDS-PAGE on homogeneous gels (e.g. using the Phast™ system from Pharmacia, Uppsala, Sweden). The concentration of SBL is determined using the Bio-Rad (Hercules, Calif.) dye reagent kit which is based on the method of Bradford (1976) *Anal. Biochem.*, 72: 248-254). Specific activity of the enzymes is determined as described below and in the examples.

One of ordinary skill in the art will appreciate that the protocol described above can be routinely modified, if necessary, for use with other enzymes. Other protocols for site-directed modification of proteins are well know to those of skill in the art and can be found, for example, in U.S. Pat. Nos. 5,932,419 and 5,789,166, 5,705,479, 5,635,475, 5,556,747, 5,354,670, 5,352,779, 5,284,760, and 5,071,743.

In addition, kits for site-directed mutagenesis are commercially available (see, e.g. Transfomer™ Site-Directed Mutagenesis Kit available from Toyobo).

3) Optimization of Coupling Site.

A number of particularly preferred sites for introduction of the cysteine and coupling the targeting moiety are indicated herein. The positions are indicated with respect to a "reference" enzyme and "homologous" sites in related enzymes in the same family can be determined, e.g. as described herein. It may, however, be desired to optimize, coupling sites for a particular enzyme, targeting moiety combination.

Because this invention utilizes chemically coupled targeting moieties this can be accomplished with relative ease and, at most, routine experimentation. Cysteines can be introduced, e.g. into positions near the reference site of interest, and then the targeting moiety can be readily conjugated as described herein. The resulting chimera can then be tested for the desired activity.

The entire protein need not be re-engineered for each variation and, because particularly preferred sites are already taught herein, only a relatively few positions need be explored to optimize any particular chimeric molecule.

4) Other Coupling Strategies.

In preferred embodiments, chemical coupling of the targeting moiety is to a cysteine, either naturally occurring in the subject enzyme or introduced (e.g. via site-directed mutagenesis. The chimeric molecules of this invention, however, need not be limited to molecules conjugated through cysteines. In certain embodiments the conjugation can be through virtually any other amino acid (e.g., a serine, a glycine, a tyrosine, etc.). The conjugation can be through the existing R group (using other coupling chemistries), or alternatively a sulfhydryl group (SH) can be introduced (linked) to the R group and the targeting moiety, derivatized as a methanethiosulfonate reagent, can be coupled, e.g. as illustrated in the examples.

5) Expression of the Mutated Enzyme.

In a preferred embodiment, the mutated enzyme is expressed from a heterologous nucleic acid in a host cell. The expressed enzyme is then isolated and, if necessary, purified. The choice of host cell and expression vectors will to a large extent depend upon the enzyme of choice and its source.

A useful expression vector contains an element that permits stable integration of the vector into the host cell genome or autonomous replication of the vector in a host cell independent of the genome of the host cell, and preferably one or more phenotypic markers that permit easy selection of transformed host cells. The expression vector may also include control sequences encoding a promoter, ribosome binding site, translation initiation signal, and, optionally, a repressor gene, a selectable marker or various activator genes. To permit the secretion of the expressed protein, nucleotides encoding a signal sequence may be inserted prior to the coding sequence of the gene. For expression under the direction of control sequences, a gene or cDNA encoding a mutated enzyme to be used according to the invention is operably linked to the control sequences in the proper reading frame.

Vectors containing the mutant genes obtained by site-directed mutagenesis are then used respectively to transform suitable host cells and expressed. Suitable host cells include bacteria such as *E. coli* or *Bacillus*, yeast such as *S. cerevisiae*, mammalian cells such as mouse fibroblast cell, or insect cells. Preferably, a bacterial expression system is used. Most preferably, the host is *Bacillus*. Protein expression is performed by processes well known in the art according to factors such as the selected host cell and the expression vector to culture the transformed host cell under conditions favorable for a high-level expression of the foreign plasmid.

Methods of cloning and expression of peptides are well known to those of skill in the art. See, for example, Sambrook, et al. (1989) *Molecular Cloning: a Laboratory Manual* (2nd Ed., Vols. 1-3, Cold Spring Harbor Laboratory), Berger and Kimmel (1987) *Methods in Enzymology*, Vol. 152: Guide to Molecular Cloning Techniques, Academic Press, Inc. San Diego, or Ausubel et al. (1987) *Current Protocols in Molecular Biology*, Greene Publishing and Wiley-Interscience, New York.

As indicated above, one particularly preferred expression system is plasmid GG274 which is then expressed in a *B. subtilis* host.

B) Coupling the Targeting Moiety to the Enzyme.

1) Selection of Substitutents for Modifying Mutated Residues.

A wide variety of targeting moieties can be coupled to the cysteine(s) introduced into the subject enzyme (e.g. serine hydrolase). As indicated above, the targeting moiety is selected depending on the desired use of the enzyme. As further indicated above, suitable targeting moieties include, but are not limited to, moieties that are bound by receptors, targeting moieties that are bound by antibodies and enzymes, targeting moieties that are bound by lectins, and various other targeting moieties. In certain particularly preferred embodiments, the targeting moieties are drugs or prodrugs that are specifically bound by a receptor and/or an enzyme.

2) Coupling Targeting Moieties to the Cysteine.

The R group on cysteines provides a convenient relatively reactive thiol group (—SH) that can be exploited for coupling a desired targeting moiety to the cysteine. In a preferred embodiment, the targeting moiety of interest is provided, derivatized as a methanethiosulfonate reagent which, when reacted with the cysteine, results in the substituent of interest covalently coupled to the cysteine by a disulfide linkage (—S—S—).

In a preferred embodiment, chemical modification with the methanethiosulfonate reagent(s) is carried out as described by Berglund et al. (1997) *J. Am. Chem. Soc.*, 119: 5265-5255 and DeSantis et al. (1998) *Biochemistry*, 37: 5968-5973. Briefly, 200 μL of a 1 M solution of the methanethiosulfonate (MTS) reagent is added to a solution (5-10 mg/mL, 3.5 mL) of the cysteine mutant in 70 mM CHES, 5 mM MES, 2 mM $CaCl_2$, pH 9.5. The MTS reagent is added in two portions over 30 minutes. Reaction mixtures are kept at 20° C. with continuous end-over-end mixing. Reactions are monitored by following the specific activity (e.g. with suc-AAPF-pNA) and by tests for residual free thiol (e.g. with Ellman's reagent). Once the reaction is complete, the reaction mixture is loaded on a Sephadex™ PD-10 G25 column with 5 mM MES and 2 mM $CaCl_2$, pH 6.5. The protein fraction is then dialyzed against 1 mM $CaCl_2$ and the dialysate is lyophilized. In a particularly preferred embodiment the fraction is dialyzed against pH 6.5 MES then flash frozen.

In certain instances, where the targeting moiety that is to be coupled to the cysteine, bears reactive groups the reactive groups may be derivatized with appropriate blocking/protecting groups to prevent undesired reactions during the coupling. Similarly, where the serine hydrolase contains one or more cysteines that are not to be derivatized, the cysteines may be replaced with other amino acids (e.g. via site directed mutagenesis) and/or the thiol group(s) on these cysteines may be derivatized with appropriate protecting groups (e.g. (e.g. benzyl, trityl, tert-butyl, MOM, acetyl, thiocarbonate, thiocarbamate, and others). The use of blocking/protecting groups is well know to those of skill in the art (see, e.g., *Protective Groups in Organic Synthesis*" Theodora W. Greene and Peter G. M. Wuts Third Edition, Wiley-Interscience, Toronto, (1999), pp 454-493.)

While in particularly preferred embodiments, a cysteine is introduced/substituted into the enzyme, in certain embodiments, other amino acids (e.g. lysine, histadine, etc.) may be introduced, and in certain embodiments, the targeting moiety may be coupled to these residues.

Derivatization of a number of targeting moieties and their coupling to mutant enzymes is illustrated in the examples provided herein.

C) Screening Chemically Chimeric Molecules for Desired Activity.

The chimeric molecules of this invention are typically screened for the activity or activities of interest. The activity of interest depends on the desired use of the chimeric molecule. Thus, for example, in the case of catalytic antagonists of this invention, the chimeric molecule may be assayed for two properties: 1) The ability to reduce or eliminate the activity of the target, e.g., where the target is biologically active, or simply to partially or fully degrade the target, e.g. where the target is not biologically active; and 2) the ability to release from the target after the target is degraded and to bind and degrade another target. Alternatively, the chimieric molecule may simply be assayed for activity (e.g. the ability to perform degradations) in a substoichiometric manner.

The details of the particular assay, will vary with the target of the chimeric molecule. Many assays for the degradation of various molecules (e.g. proteins, carbohydrates, nucleic acids, etc.) and/or the inhibition of various receptors and/or antibodies are well known to those of skill in the art. For example, in one embodiment, activity of a molecule on a cell surface receptor can be determined by providing a cell expressing the receptor and measuring the activity of the receptor in the presence or absence of the chimeric molecule. Receptor assays are commonly performed in oocytes (e.g. *Xenopus* oocytes) into which an RNA encoding the subject receptor is inserted. Receptor activity is monitored by measuring electrochemical activity (e.g. via patch clamps, etc.), uptake of receptor substrates, and the like. Such methods are well known to those of skill in the art and described in detail, for example, Racke et al. (1993) *FEBS Letters* 333 (1, 2): 132-136. Assays for ligand binding, alteration of enzyme activity, and the like are also well known to those of skill in the art. In addition, a number of suitable assays are provided in the examples.

V. Illustrative Uses of Catalytic Antagonists and/or Redirected Enzymes.

From the foregoing discussion myriad applications/uses of the chimeric molecules of this invention will be apparent to one of ordinary skill in the art. Moreover, a number of specific embodiments and applications are described in the discussion of targeting moieties. By way of further illustration, however, a number of specific, particularly preferred embodiments are discussed below.

A) Therapeutics Based on Targeted Destruction

As indicated above, the catalytic antagonists of this invention can be used as therapeutic in a wide number of pathologies including, but not limited to inhibitors of viral infection and/or replication, inhibitors of bacterial infection and/or biofilm formation, modulators of an immune response, modulators of an autoimmune response, inhibitors of an inflammatory response, and the like. More generally, as indicated above, the catalytic antagonists of this invention can be used to replace existing pharmaceuticals where the pharmaceutical acts by inhibiting and/or antagonizing a receptor.

It was explained above, that a wide variety of pharmaceuticals act as antagonists of receptors or receptor mediated activity. These pharmaceuticals typically specifically bind a particular receptor and or enzyme. The use of such pharmaceuticals as targeting moieties in catalytic antagonists of this invention where they are attached to an enzyme (e.g. a serine hydrolase) that degrades the target receptor and/or enzyme essentially renders the drug catalytic. Thus, instead of acting in a stoichiometric manner (a single drug molecule blocks/antagonizes a single receptor), when converted into catalytic antagonists, the new drug acts in a substoichiometric manner (a single molecule can antagonize an essentially unlimited number of receptors). Moreover, in contrast to the drug alone (where the receptor often regains activity when the drug is released), a receptor bound by a catalytic antagonist of this invention is degraded (thereby releasing the catalytic antagonist to act on another receptor). Because the receptor is degraded it does not recover its activity. The catalytic antagonists are thus expected to provide greater efficacy at a lower dosage and to provide longer lasting activity at a particular dosage.

Thus, in one embodiment, this invention provides methods of improving the activity of a drug. The methods involve attaching the drug to an enzyme capable of degrading the target (e.g. receptor) to which the drug binds. Preferred enzymes in this context include hydrolases and even more preferably include proteases (e.g. serine proteases, metalloproteases, cysteine proteases, aspartyl proteases, etc.).

It was explained above, however, that the targeting moieties need not be limited to drugs. A wide variety of other targeting moieties are suitable as well and provide catalytic antagonists useful in a wide variety of therapeutic contexts. Thus, for example, in one embodiment, the targeting moiety can be a molecule that specifically binds to the CCR5 and/or CXCR2 receptors, commonly found on lymphocytes (e.g. T-cells). CCR5 and CXCR2 receptors are implicated in the infection of a cell by HIV and persons defective in one or more of these receptors typically demonstrate resistance to HIV infection. Targeted destruction/inhibition of either or both of these receptors, e.g. by a catalytic antagonist comprising a CCR5 and/or CXCR2 specific targeting agent attached to a suitable hydrolase (e.g. subtilisin) will increase the target cell's resistance to HIV infection.

In another embodiment, glycosidases involved in N-linked protein glycosylation can be specifically targeted (e.g. using an Aza-sugar targeting moiety) attached to a suitable hydrolase (e.g. subtilisin, pepsin, etc.). Such a catalytic antagonist will be of use in the treatment of HIV, herpes, other viruses, and various cancers.

Catalytic antagonists comprising a sugar targeting moiety attached to a suitable hydrolase (e.g. subtilisin, pepsin, etc.) will be useful in the treatment of a wide variety of conditions, including inflammatory responses (e.g. associated with arthritis, septic shock, myocardial infarction, etc.), bacterial binding to cells and subsequent infection (e.g. *H. pylori* infection associated with ulcers). Where the targeting moiety is a Galα (1,4)Gal pathogenic *E. coli* infections can be blocked. In addition, lectin-directed catalytic antagonists can be used to inhibit biofilm formation in vivo or ex vivo.

In still another embodiment the targeting moiety can be a sialic acid sugar (or mimetics such as Rilenza (Glaxo-Wellcome) or the like). When attached to a suitable hydrolase (e.g. subtilisin) the catalytic antagonist can specifically target the sialidase activity of viruses such as influenza.

The chimeric catalytic antagonists of this invention can also be used to specifically target hyperproliferative and/or invasive cells (e.g. metastatic cells). Various enzymes (e.g. especially matrix metalloproteases) are known to be highly active in invasive cells. These enzymes can be specifically targeted using a number of targeting moieties (e.g. crown ethers). When attached to suitable hydrolase (e.g. a subtilisin) the catalytic antagonist will degrade the target enzyme (e.g. metalloprotease) and thereby interfere with or eliminate the ability of a cell to invade, e.g. a basement membrane, thereby slowing the progression of a cancer.

The catalytic antagonists of this invention can also be used to target and alter a variety of immune processes. Thus, for example, by using a target directed at a T-cell receptor, e.g. by using a MHC complex from a xenotransplant, it is possible to inhibit immune cells that mount an immune response directed against that antigen. In a related embodiment, alpha-Gal epitope disaccharide (Galα(1,3)Gal) can be used as a targeting moiety and (e.g. when attached to a subtilisin) can bind to and specifically inhibit alpha-Gal epitope specific antibodies thereby mitigating host rejection of a xenograft. Similarly, known allergens (e.g. various pollens or epitopes present on such allergens) can be used as targeting moieties to target and inhibit T-cells and/or antibodies that specifically recognize such antigens. This will mitigate allergic reactions against such allergens.

B) Drug Delivery Strategies

As indicated above, the chimeric molecules can be used in various drug delivery strategies to specifically target a therapeutic activity to a cell, organ, or tissue of interest. In certain embodiments, as described above, enzymes capable of converting prodrugs to their active form are attached to a targeting moiety (e.g. a tumor cell specific moiety) that localizes them to the site of desired activity (e.g. a tumor cell), various prodrugs are known to those of skill in the art and include, but are not limited to ganclovir activated by thymidine kinase, phosphenyloin converted to phenyloin by a phosphatase, depivefrin is converted to epinephrine by an esterase and the like.

Another example of a "drug delivery" strategy uses the targeted chimeric molecule to deliver an enzyme having an activity that supplements an absent, typically endogenous activity. Thus, for example, glucocerebrosidase may be directed, e.g. to spleen cells in the treatment of Gaucher's or Tay-Sachs disease. Similarly superoxide dismutase may be attached to liver cell specific targeting moieties so that it is targeted to liver tissue where it can provide anti-oxidant activity.

C) Other Embodiments

In other particularly preferred embodiments, the chimeric molecules of this invention can be used to target and destroy particular preselected molecules whether or not they have a biological activity. Thus, for example, components of various soils or stains (e.g. milk, blood, eggs, grass stains, oil stains, etc.) can be specifically targeted. For example, avidin/egg protein can be specifically targeted by using a biotin as a targeting moiety to specifically directed, e.g. a protease to the site. The stain is degraded/digested and thereby released from the underlying substrate. Such specifically targeted chimeras are particularly in various cleaning formulations.

VI. Pharmaceutical Formulations.

The therapeutic chimeric molecules of this invention, (e.g. the therapeutic catalytic antagonists) are useful for intravenous, parenteral, topical, oral, or local administration (e.g., by aerosol or transdermally). Particularly preferred modes of administration include intra-arterial injection, more preferably intra-peritoneal intra-hepatic artery injection or, where it is desired to deliver a composition to the brain, (e.g., for treatment of brain tumors) a carotid artery or an artery of the carotid system of arteries (e.g., occipital artery, auricular artery, temporal artery, cerebral artery, maxillary artery, etc.). The chimeric molecules are typically combined with a pharmaceutically acceptable carrier (excipient) to form a pharmacological composition. Pharmaceutically acceptable carriers can contain a physiologically acceptable compound that acts, for example, to stabilize the composition or to increase or decrease the absorption of the agent. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the anti-mitotic agents, or excipients or other stabilizers and/or buffers.

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of a pharmaceutically acceptable carrier, including a physiologically acceptable compound depends, for example, on the route of administration of the chimeric molecule and on the particular physio-chemical characteristics of the agent.

The pharmaceutical compositions can be administered in a variety of unit dosage forms depending upon the method of administration. For example, unit dosage forms suitable for oral administration include powder, tablets, pills, capsules and lozenges. It is recognized that the chimeric molecules, when administered orally, are preferably protected from digestion. This is typically accomplished either by complexing the subject molecule with a composition to render it resistant to acidic and enzymatic hydrolysis or by packaging the chimeric molecule agent in an appropriately resistant carrier such as a liposome. Means of protecting compounds from digestion are well known in the art (see, e.g., U.S. Pat. No. 5,391,377 describing lipid compositions for oral delivery of therapeutic agents).

Certain chimeric molecules of this invention may be only marginally soluble in aqueous solutions. In a preferred embodiment, these compositions are either delivered directly to the desired site (e.g. by injection, cannulization, or direct application during a surgical procedure) or they are solubilized in an acceptable excipient.

The pharmaceutical compositions of this invention are useful for topical administration e.g., in surgical wounds to treat incipient tumors, neoplastic and metastatic cells and their precursors. In another embodiment, the compositions are useful for parenteral administration, such as intravenous administration or administration into a body cavity or lumen of an organ. The compositions for administration will commonly comprise a solution of the chimeric molecule agent dissolved in a pharmaceutically acceptable carrier, preferably an aqueous carrier for water-soluble chimeric molecules. A variety of carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of chimeric molecule in these formulations can vary widely, and will be selected primarily based on fluid volumes, viscosities, body weight and the like in accordance with the particular mode of administration selected and the patient's needs. Actual methods for preparing administrable compositions will be known or apparent to those skilled in the art and are described in more detail in such publications as *Remington's Pharmaceutical Science,* 15th ed., Mack Publishing Company, Easton, Pa. (1980).

Dosages for typical chemotherapeutics are well known to those of skill in the art. Moreover, such dosages are typically advisorial in nature and may be adjusted depending on the particular therapeutic context, patient tolerance, etc. Single or multiple administrations of the compositions may be administered depending on the dosage and frequency as required and tolerated by the patient. In any event, the composition should provide a sufficient quantity of the proteins of this invention to effectively treat the patient.

In the case of therapeutic chimeric molecules dosage for a typical pharmaceutical composition for intravenous administration would be about 0.01 to per patient per day. Dosages from 0.1 up to about 1000 mg per patient per day may be used, particularly when the drug is administered to a secluded site and not into the blood stream, such as into a body cavity or into a lumen of an organ.

VII. Kits.

In certain embodiments, this invention provides kits for the creation and/or use of the chimeric molecules of this invention. In one embodiment the kits comprise one or more containers containing one or more targeting moieties derivatized as methanesulfonates for coupling to a cysteine in an enzyme. In addition or alternatively the kits may comprise one or more enzymes, more preferably mutant enzymes having an inserted cysteine ready for coupling to a methanesulfonate derivatized targeting moiety. When provided in this manner the kits enable one or ordinary skill in the art to assemble the desired chimeric molecule for a particular use. Thus, for example one typically kit may include a multiplicity of methanesulfonate derivatized targeting moieties and one or more enzymes suitable for coupling. The desired enzyme is then reacted (as described herein) with the desired targeting moiety to produce the desired chimeric molecule. Such kits may additional comprise one or more of the reagents utilized in a typical coupling reaction.

In another embodiment, this invention provides one or more chimeric molecules (e.g. catalytic antagonists and/or redirected enzymes) of this invention. The chimeric molecules can be provided as a dry (e.g. lyophilized powder) or in solution and/or as an emulsion. In certain embodiments the chimeric molecules are provided in, or along with, a pharmacological excipient and, optionally, may be provided in a unit dosage format.

The kits may optionally include any reagents and/or apparatus to facilitate the uses described herein. Such reagents include, but are not limited to buffers, organic solvents, labels, labeled antibodies, bioreactors, cells, etc.

In addition, the kits may include instructional materials containing directions (i.e., protocols) for the assembly of chimeric molecules of this invention and/or for the use thereof. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention. The following examples detail the construction and evaluation of a number of chimeric molecules of this invention. In particular, Examples 1-4 demonstrates the highly specific selectivity of a catalytic antagonist of this invention in which the targeting moiety is a known enzyme inhibitor. Examples 5 through 7 detail the construction and evaluation of chimeric molecules in which the chimeric molecules are targeted to the binding protein lectin concanavalin A. Examples 8 through 10 detail the construction and evaluation of chimeric molecules in which the chimeric molecules are targeted to the binding protein avidin. Examples 11 and 12 detail the construction and evaluation of chimeric molecules in which the chimeric molecules are targeted to a monoclonal anti-biotin antibody IgG. Example 13 details the respective stoichiometry of these examples.

Example 1

Targeting Enzymes with Inhibitors

Synthesis and Attachment of an HLADH inhibitor to SBL and Characterization of the Resulting SBL-S-pyrazole CMMs In order to direct SBL towards various enzyme targets for their degradation, we decided to attach specific inhibitors for those enzymes to SBL by our combined site directed mutagenesis chemical modification (CMM) approach FIG. 2).

Figure 3:
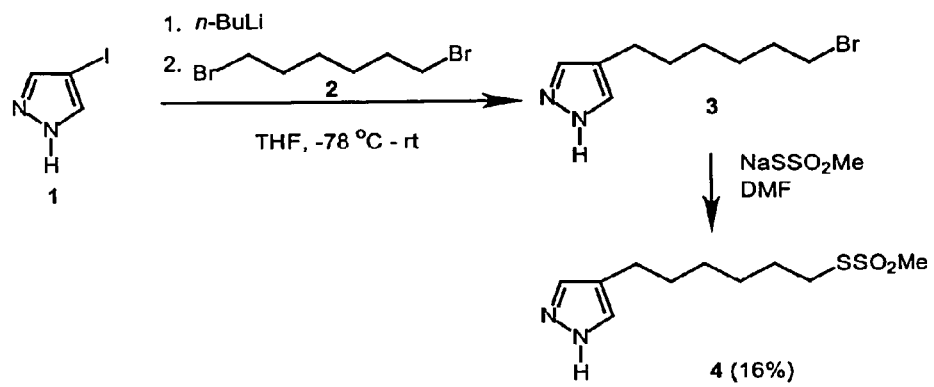
FIG. 3 illustrates scheme 11 for synthesis of MTS-pyrazole 4.

In a preferred embodiment the inhibitor(s) chosen as targeting moieties for this approach are strong inhibitor(s)/degraders of the target enzyme, but are poor inhibitors of the CMM. In this example, alcohol dehydrogenase (ADH), which is strongly inhibited by 4-pyrazole derivatives, was chosen as the target enzyme and the inhibitors chosen as targeting were pyrazoles known to inhibit ADH. The modified CMM in this case was a subtilisin (SBL).s In one embodiment, horse liver alcohol dehydrogenase (HLADH) was chosen as the target enzyme. Several 4-substituted pyrazoles are described as reasonable selective inhibitors of HLADH (Theorell and Yonetani (1963) *Biochem. Z.*, 388: 537-553; Theorell et al. (1969) *Acta Chem. Scand.*, 23: 255-260; Tolf et al. (1979) *Acta Chem. Scand. B* 33: 483-487; Tolf et al. (1982) *Acta Chem. Scand. B*, 36: 101-107). Pyrazole derivatives with long hydrophobic alkyl substituents in 4-position inhibit HLADH activity especially strongly. The binding affinity of this substituent and hence the inhibitory power of the 4-pyrazole increases as the alkyl chain length increases up to six carbon atoms. 4-hexylpyrazole is known to inhibit horse liver alcohol dehydrogenase (LADH) with $K_I$=0.5 nm. Therefore, we decided to synthesize a pyrazole-MTS reagent bearing a methanesulfonyl-hexyl side chain at the 4-position. The synthesis of the MTS-pyrazole reagent is illustrated by scheme 11 (FIG. 3).

Synthesis of the MTS-Pyrazole

Halogen-metal exchange of 4-iodopyrazole (1) with n-BuLi, and subsequent coupling with an excess of 1,6-dibromohexane (2) provided 4-(6-bromo)-hexylpyrazole (3). Attempts to purify compound 3 were only partially successful. Reaction of crude bromide 3 with sodium methanethiosulfonate furnished the MTS-pyrazole 4 in 16% overall yield. Although the overall yield was low, no attempts towards optimization were made as this would have probably required the use of protecting groups. Therefore, the MTS-pyrazole 4 can be synthesized in a straightforward two step reaction sequence as outlined in scheme 11 (FIG. 3).

Inhibition of SBL-WT by Pyrazole

To determine how much modification with a pyrazole will influence the catalytic activity of SBL we carried out $K_I$ measurements for SBL-WT using the method of Waley (Waley (1982) *Biochem. J.*, 205: 631) with our standard substrate suc-AAPFpNA and standard conditions (pH 8.6, 0.1 M Tris with 0.005% Tween 80, 1% DMSO). Unsubstituted pyrazole does not significantly inhibit SBL-WT ($K_M$=0.73±0.05 mM, $k_{cat}$=153±4 $k_{cat}/K_M$=209±15 mM s$^{-1}$, $K_I$=97.2±7.2 mM). Attempts to use the same method for the determination of the $K_I$ of SBL-WT with the MTS-pyrazole 4 failed due to the insolubility of the pyrazole compound.

Modification and Characterization of the Pyrazole-CMMs

N62C, L217C, S166C, and S156C mutants were modified with the MTS-pyrazole reagent 4 by reaction at pH 9.5 following the standard protocol. In all cases the resulting enzymes were active after modification and the data for amidase kinetics (substrate suc-AAPFpNA) and ESMS are shown in Table 2.

TABLE 2 vKinetic constants for pyrazole-CMMs

| Pyrazole- | Amidase Kinetics | | | ESMS | |
|---|---|---|---|---|---|
| CMM | $k_{cat}$ | $K_M$ | $k_{cat}/K_M$ | Calc. | Found |
| S166C | 10.4 ± 0.2 | 0.46 ± 0.03 | 22.7 ± 1.4 | 26896 | 26900 |
| S156C | 59.8 ± 1.5 | 0.65 ± 0.05 | 92.2 ± 7.2 | 26896 | 26897 |
| N62C | 97.9 ± 2.3 | 0.90 ± 0.05 | 109 ± 6.6 | 26869 | 26868 |
| L217C | 61.3 ± 1.0 | 0.87 ± 0.04 | 70.2 ± 3.1 | 26870 | ???-a |
| GG36-WT | 153 ± 4 | 0.73 ± 0.05 | 209 ± 15 | 26698 | 26694 | aCould not be obtained until now due to measurement problems.
Kinetic constants determined in duplicate by method of initial rates in 0.1M TRIS buffer, pH 8.6, 0.005% Tween 80, 1% DMSO. [S] = 0.125 mM to 3 mM, [E] = 1.5 × 10$^{-8}$ M to 9.0 × 10$^{-8}$ M.

Although it has the smallest $K_M$ value among all pyrazole-CMMs, the S166C-S-Pyrazole CMM shows the lowest $k_{cat}/K_M$; about 9 times smaller than for SBL-WT.

The $k_{cat}$ of the S156- and L217C-S-Pyrazole CMM were both very similar and about 2.5 times smaller than for the WT enzyme. Their substrate binding properties, however, were fairly different: S156C-S-Pyrazole bound better than SBL-WT whereas the $K_M$ of L217C-S-Pyrazole is larger than that of the WT enzyme.

N62C-S-Pyrazole is slightly more active than the other pyrazole CMMs and its $k_{cat}$ is just 1.5 times smaller compared to SBL-WT. However it had the largest $K_M$ among all pyrazole-CMMs and its $k_{cat}/K_M$ was about 2 times smaller compared to SBL-WT.

Experimental Details 4-(6-M ethanethiosulfonyl)hexylpyrazole (MTS-Pyrazole) (4)

n-Butyl lithium (2.5 M solution in hexanes, 12.4 mL, 30.9 mmol) was added dropwise to a solution of 4-iodopyrazole (1) (2.00 g, 10.3 mmol) in THF (40 mL) at −78° C. under N$_2$. After 0.5 h a solution of 1,6-dibromohexane (2) (5.03 g, 20.6 mmol) in THF (40 mL) was added slowly. When the addition was complete, the reaction mixture was allowed to warm up to rt and was stirred overnight. Water (50 mL) was added, the layers were separated and the aqueous layer was extracted with AcOEt (4×50 mL). The combined organic layers were washed with brine (50 mL) and dried (MgSO$_4$). Evaporation of the solvent and subsequent drying under vacuum furnished 5.03 g crude product as a brown oil. Separation by flash chromatography (silica gel, hexanes:AcOEt, gradient elution, 95:5 to 55:45) provided 0.810 g (34%) 4-(6-bromo)-hexylpyrazole (3) as a yellow oil; $^1$H NMR (CDCl$_3$, 300 MHz) δ 1.35-1.48 (m, 4H), 1.51-1.63 (m, 2H), 1.79-1.90 (m, 2H), 2.50 (t, 7.5 Hz, 2H, H-1'), 3.40 (t, J$_{5',6'}$ 7.0 Hz, 2H, H-6'), 7.42 (s, 2H, H-3, H-5), 11.5 (s, 1H, NH); $^{13}$C NMR (CDCl$_3$, 75.5 MHz) δ 23.9, 28.0, 28.4, 30.8, 32.8, 34.1 [(CH$_2$)$_6$], 120.9 (C-4), 132.6* (C-3, C-5), *signal has double intensity. Both NMR spectra contain additional signals due to impurities. Bromo-compound 3 was not further purified and characterized. Furthermore 2.41 g (48%) dibromide 2 could be reisolated.

NaSSO$_2$Me (0.319 g, 2.38 mmol) was added to a solution of crude bromide 2 (0.400 g, max. 1.73 mmol) in DMF (10 mL) and the resulting solution heated under nitrogen at 50° C. After 16 h water (10 mL) and AcOEt (10 mL) were added, the layers were separated and the aqueous layer was extracted with AcOEt (4×10 mL). The combined organic layers were washed with brine (10 mL) and dried (MgSO$_4$). Evaporation of the solvent and subsequent drying under vacuum furnished 0.350 g crude product as a yellow oil. Separation by flash chromatography (silica gel, hexanes:AcOEt, gradient elution, 8:2 to 0:1) furnished 0.215 g (16% over two steps)

4-(6-methanethiosulfonyl)-hexylpyrazole (4) as a colourless solid, mp 68-70; IR (KBr) 3170, 3165 (NH), 3065, 3024 (arC—H), 2932, 2854 (C—H), 1306, 1122 (S—$SO_2$) cm$^{-1}$; $^1$H NMR (CDCl$_3$, 300 MHz) δ 1.35-1.47 (m, 4H), 1.52-1.62 (m, 2H), 1.70-1.79 (m, 2H), 2.48 (t, $J_{1',2'}$, 7.5 Hz, 2H, H-1'), 3.14 (t, $J_{5',6'}$ 7.5 Hz, 2H, H-6'), 3.30 (s, 3H, CH$_3$SO$_2$), 7.40 (s, 2H, H-3, H-5), 11.5 (s, 1H, NH); $^{13}$C NMR (CDCl$_3$, 75.5 MHz) δ 23.6, 28.0, 28.2, 30.4, 36.1 [(CH$_2$)$_5$], 50.3 (CH$_3$SO$_2$), 120.4 (C-4), 132.3* (C-3, C-5), *signal has double intensity; HRMS m/z (EI) Found 263.0882 (M+H$^+$); C$_{10}$H$_{19}$N$_2$O$_2$S$_2$ requires 263.0888.

Standard Modification Protocol

General Procedure for Modification of SBL Mutants Stored as Flash-Frozen Solutions:

A 1.25 mL frozen aliquot of the mutant enzyme (N62C, L217C or S166C) containing approximately 25 mg of enzyme was thawed and added to 1.25 mL of Modifying Buffer (see below) in a polypropylene test-tube. To this solution was added 100 μL of a 0.2 M MTS reagent solution The mixture was sealed, vortexed and placed on an end-over-end rotator at room temperature. When the modification was complete (determined by a specific activity assay, using succinyl-AlaAlaProPhe-p-nitroanilide [$\epsilon_{410}$=8800 M$^{-1}$ cm$^{-1}$](Bonneau et al. (1991) *J. Am. Chem. Soc.* 119: 1026-1030.) as substrate in 0.1 M Tris-HCl buffer containing 0.005% Tween 80, 1% DMSO, pH 8.6 showing constant activity and titration with Ellman's reagent (Ellman et al. (1961) *Biochem. Pharmacol.* 7: 88-95.)($\epsilon_{412}$=13600 M$^{-1}$ cm$^{-1}$) showing no free thiol present in solution), a further 50 μL of the modifying reagent solution was added and the mixture placed back on the end-over-end rotator for a further 10 minutes. The reaction was poured onto a pre-packed, pre-equilibrated G-25 Sephadex® PD10 column and eluted with 3.5 mL Quench Buffer (see below). The eluant was dialysed at 4° C. against 10 mM MES, 1 mM CaCl$_2$ pH 5.8 (2_1 L, 2_45 min). The resulting dialysate was flash frozen in liquid nitrogen and stored at −18° C.

Modifying. Buffer: pH 9.5:140 mM CHES, 2 mM CaCl$_2$
  pH 7.5:140 mM HEPES, 2 mM CaCl$_2$
  pH 5.5:140 mM MES, 2 mM CaCl$_2$
Quench Buffer Reactions at pH 7.5-9.5:5 mM MES 1 mM CaCl$_2$ pH 6.5
  Reactions at pH 5.5:5 mM MES 1 mM CaCl$_2$ pH 5.5

The free thiol content of all CMMs, was determined spectrophotometrically by titration with Ellman's reagent in phosphate buffer 0.25 M, pH 8.0. In all cases no free thiol was detected. Modified enzymes were analyzed by nondenaturing gradient (8-25%) gels at pH 4.2, run towards the cathode, on the Pharmacia Phast-system and appeared as a single band. Prior to ES-MS analysis CMMs were purified by FPLC (Bio-Rad, Biologic System) on a Source 15 RPC matrix (17-0727-20 from Pharmacia) with 5% acetonitrile, 0.01% TFA as the running buffer and eluted with 80% acetonitrile, 0.01% TFA in a one step gradient.

General Procedure for Modification of SBL Mutants Stored as Lyophilized Powders:

This procedure is only used with S156C, which is stored as a lyophilized powder to prevent dimerization. Into a polypropylene test tube was weighed about 25-30 mg of lyophilized S156C. This was dissolved in the following modifying buffers (2.5 mL):
  pH 9.5:70 mM CHES, 2 mM CaCl$_2$
  pH 7.5:70 mM HEPES, 2 mM CaCl$_2$
  pH 5.5:70 mM MES, 2 mM CaCl$_2$ MTS reagent was added and the reaction then proceeded as for flash-frozen mutant solutions, using the appropriate quench buffer.

General Method for Amidase Kinetics Analysis of SBL Conjugates

Michaelis-Menten constants were measured at 25(±0.2)° C. by curve fitting (GraFit® 3.03) of the initial rate data determined at nine concentrations (0.125 mM-3.0 mM) of succinyl-AAPF-pNA substrate in 0.1 M Tris-HCl buffer containing 0.005% Tween 80, 1% DMSO, pH 8.6 ($\epsilon_{410}$=8800 M$^{-1}$ cm$^{-1}$)(Bonneau et al. (1991) *J. Am. Chem. Soc.* 119: 1026-1030).

General Method for Esterase Kinetics Analysis of SBL Conjugates

Specificity constants determined using the low substrate approximation were measured indirectly using Ellman's reagent ($\epsilon_{412}$=13600 M$^{-1}$ cm$^{-1}$) using 15 or 30 succinyl-AAPF-SBn as substrate in 0.1 M Tris.HCl, containing 0.005 vol % Tween-80, 1 vol % 37.5 mM Ellman's reagent in DMSO, pH 8.6.

Michaelis-Menten constants were measured at 25° C. by curve fitting (GraFit® 3.03) of the initial rate data determined at eight concentrations (31.25 μM-2.0 mM) of the succinyl-AAPF-SBn substrate, followed indirectly using Ellman's reagent in 0.1 M Tris.HCl, containing 0.005 vol % Tween-80, 1 vol % 37.5 mM Ellman's reagent in DMSO, pH 8.6.

Example 2

Initial HLADH Targeting Assay

Assessing the Targeting of HLADH by Suprastoichiometric pyrazole-CMMs and then the Degradation Targeting of pyrazole-CMMs to HLADH will be evident from reduction in ADH activity due to inhibition by the pyrazole moiety of the CMM.

Figure 4:
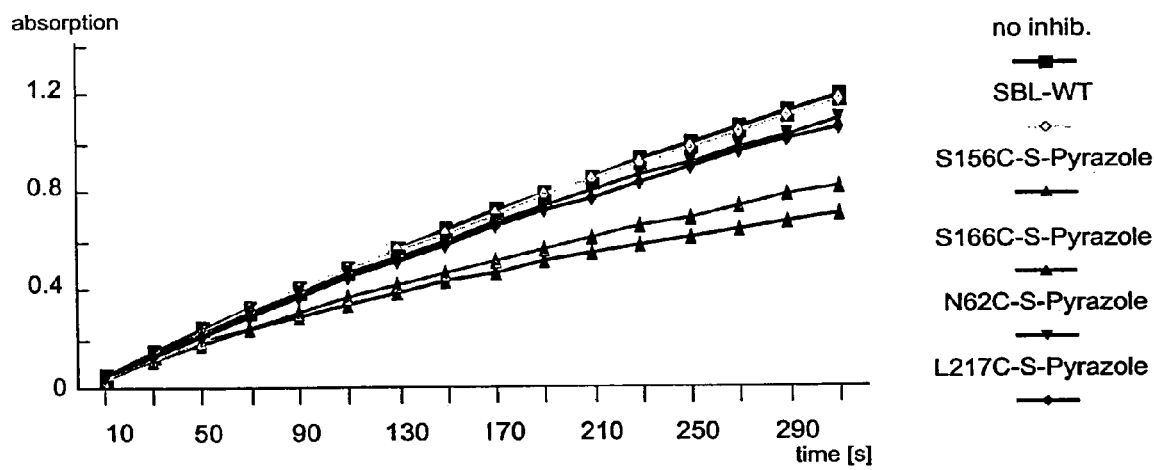
FIG. 4 illustrates results of HLADH targeting assay for SBL-pyrazole chimeric molecules.
Figure 5A:
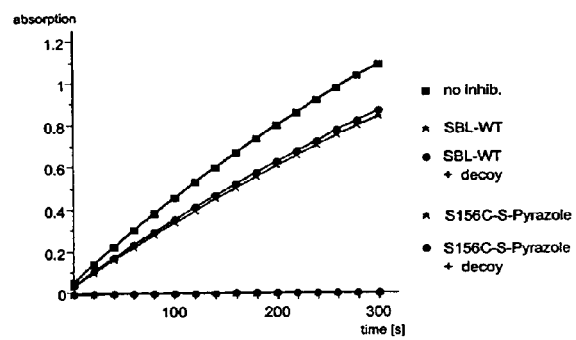
FIG. 5A, FIG. 5B, FIG. 5C, and FIG. 5D illustrate results of HLADH degradation assay for SBL-pyrazole chimeric molecules.
Figure 5B:
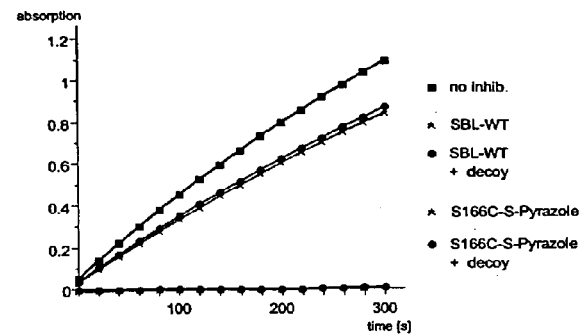
Figure 5C:
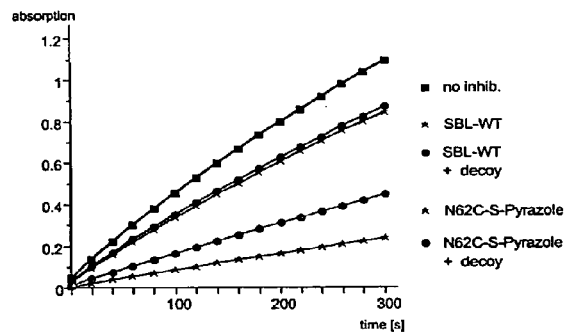
Figure 5D:
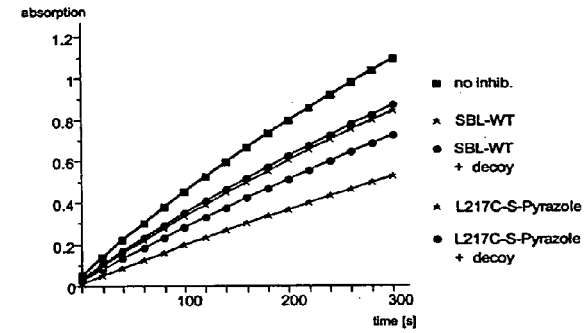

Hence, the catalytic activity of HLADH in absence and presence of the pyrazole-CMMs was investigated. Controls were carried out with SBL-WT. The amount of CMM and WT used was calculated for equal amounts of active enzyme as determined by PMSF titration. Cyclohexanol was used as HLADH substrate and NAD$^+$ as cofactor. FIG. 4 shows the results of this "Targeting Assay".

As expected, SBL-WT did not influence the activity of HLADH significantly, whereas all pyrazole-CMMs inhibit HLADH. The most efficient inhibition was caused by S156C-S-Pyrazole, the only CMM with surface exposed side chain. N62C-S-Pyrazole and L217C-S-Pyrazole demonstrated very similar inhibition power. Surprisingly, S166C-S-Pyrazole inhibited HLADH quite strongly, even though its modified side chain is buried in the S$_1$ pocket. This may be rationalized in terms of the pyrazole moiety adopting a conformation where it bends outside the binding pocket. These results clearly demonstrate the ability of our modified enzymes to target another enzyme via an inhibitor.

Targeted association of CMMs with HLADH via the pyrazole inhibitor should lead to selective hydrolysis. If hydrolysis of the HLADH takes place, the oxidoreductase activity of the HLADH should be diminished or eradicated after a certain time of incubation with our CMMs. To demonstrate this, the "Targeting Assay" as described above was carried out again after 4 h incubation. Remaining HLADH activity was determined by addition of cyclohexanol as substrate. The results are shown in FIG. 5.

Experimental for HLADH Targeting Assay
Six cuvettes were filled as shown in Table 3.

TABLE 3

Setup for HLADH targeting assay.

| Cuvette No. | Buffer[a]/ μL | Cyclohexane[b]/ μL | NAD+[c]/ μL | HLADH[d]/ μL | Inhibitor-Enzyme[e]/ μL |
|---|---|---|---|---|---|
| 1 | 2535 | 300 | 150 | 15 | — |
| 2 | 2435 | 300 | 150 | 15 | 100 of SBL-WT[f] (1.072 mg/mL, 64%) |
| 3 | 2435 | 300 | 150 | 15 | 100 of S156C-S-Pyrazole (0.686 mg/mL) |
| 4 | 2496 | 300 | 150 | 15 | 39.0 of S166C-S-Pyrazole (1.76 mg/mL) |
| 5 | 2508 | 300 | 150 | 15 | 27.2 of N62C-S-Pyrazole (2.52 mg/mL) |
| 6 | 2483 | 300 | 150 | 15 | 52.0 of L217C-S-Pyrazole (1.32 mg/mL) |

[a]Assay buffer: 0.1M Glycine-NaOH, pH 9.0.
[b]Solution (10 mg/mL) in Assay buffer.
[c]Solution (33.2 mg/mL) in Assay buffer.
[d]Solution (10 mg/mL, 52.4% activity) in TRIS-HCl buffer (0.05M TRIS, pH 7.4).
[e]The amounts are calculated for equal concentrations of active enzyme (as determined by initial rate kinetics with succ-AAPFpNA).
[f]Lyophylized enzyme dissolved in MES buffer (10 mM MES, 1 mM $CaCl_2$, pH 5.8).

Before addition of HLADH the cuvette was equilibrated in the spectrophotometer for two minutes. HLADH was added and $A_{340}$ was measured every 20 s over a period of 300 s. The measurements were carried out in duplicate. The results are shown in Table 4.

TABLE 4

Results for HLADH targeting assay.

| Time [s] | control | SBL-WT | S156CMM | S166CMM | N62CMM | L217-CMM |
|---|---|---|---|---|---|---|
| 10 | 0.058 | 0.053 | 0.050 | 0.046 | 0.055 | 0.050 |
| 30 | 0.150 | 0.145 | 0.121 | 0.122 | 0.145 | 0.138 |
| 50 | 0.239 | 0.234 | 0.185 | 0.191 | 0.230 | 0.221 |
| 70 | 0.326 | 0.320 | 0.242 | 0.254 | 0.311 | 0.300 |
| 90 | 0.409 | 0.403 | 0.294 | 0.314 | 0.389 | 0.377 |
| 110 | 0.489 | 0.483 | 0.343 | 0.370 | 0.463 | 0.450 |
| 130 | 0.567 | 0.561 | 0.388 | 0.423 | 0.535 | 0.520 |
| 150 | 0.642 | 0.636 | 0.431 | 0.474 | 0.604 | 0.588 |
| 170 | 0.716 | 0.709 | 0.472 | 0.522 | 0.671 | 0.654 |
| 190 | 0.787 | 0.780 | 0.511 | 0.569 | 0.736 | 0.717 |
| 210 | 0.856 | 0.849 | 0.547 | 0.614 | 0.799 | 0.779 |
| 230 | 0.924 | 0.916 | 0.583 | 0.658 | 0.860 | 0.839 |
| 250 | 0.990 | 0.982 | 0.617 | 0.700 | 0.919 | 0.898 |
| 270 | 1.054 | 1.046 | 0.650 | 0.741 | 0.977 | 0.955 |
| 290 | 1.117 | 1.108 | 0.681 | 0.781 | 1.034 | 1.011 |
| 310 | 1.178 | 1.169 | 0.712 | 0.821 | 1.089 | 1.065 |

Experimental for HLADH Targeting Assay
Six eppendorf vials were filled as shown in Table 5.

TABLE 5

Setup for HLADH targeting assay.

| Vial Number | Buffer[a]/ μL | NAD+[b]/ μL | HLADH[c]/ μL | Decoy[d] μL | Inhibitor-Enzyme[e]/ μL |
|---|---|---|---|---|---|
| 1 | 535 | 150 | 15 | — | — |
| 2 | 435 | 150 | 15 | 100 | — |
| 3 | 435 | 150 | 15 | — | 100 of SBL-WT[f] (1.072 mg/mL, 64%) |
| 4 | 335 | 150 | 15 | 100 | 100 of SBL-WT[f] (1.072 mg/mL, 64%) |
| 5 | 435 | 150 | 15 | — | 100 of S156C-S-Pyrazole (0.686 mg/mL) |
| 6 | 335 | 150 | 15 | 100 | 100 of S156C-S-Pyrazole (0.686 mg/mL) |
| 7 | 496 | 150 | 15 | — | 39.0 of S166C-S-Pyrazole (1.76 mg/mL) |
| 8 | 396 | 150 | 15 | 100 | 39.0 of S166C-S-Pyrazole (1.76 mg/mL) |
| 9 | 508 | 150 | 15 | — | 27.2 of N62C-S-Pyrazole (2.52 mg/mL) |
| 10 | 408 | 150 | 15 | 100 | 27.2 of N62C-S-Pyrazole (2.52 mg/mL) |
| 11 | 483 | 150 | 15 | — | 52.0 of L217C-S-Pyrazole (1.32 mg/mL) |
| 12 | 383 | 150 | 15 | 100 | 52.0 of L217C-S-Pyrazole (1.32 mg/mL) |

[a]Assay buffer: 0.1M Glycine-NaOH, pH 9.0.
[b]Solution (33.2 mg/mL) in Assay buffer.
[c]Solution (10 mg/mL) in TRIS-HCl buffer (0.05M TRIS, pH 7.4).
[d]0.5 mg/mL solution of Ribonuclease A with Scrambled Disulfide Bonds (Sigma) in Milli-Q water.
[e]The amounts are calculated for equal concentrations of active enzyme (as determined by PMSF titration).
[f]Lyophylized enzyme dissolved in MES buffer (10 mM MES, 1 mM $CaCl_2$, pH 5.8).

These solutions were incubated at 35° C. in a thermostat-controlled water bath for 4 h. 650 μL solution of each eppendorf vial was mixed with 2 mL Assay buffer in a cuvette. After two minutes of equilibration in the spectrophotometer and autozeroing, cyclohexanol (300 μL) was added and $A_{340}$ was measured every 20 s over a period of 300 s. The measurements were carried out in duplicate and are shown in Table 6.

TABLE 6

Results for HLADH targeting assay.

| time [s] | Control[a] | SBL-WT 1[b] | SBL-WT 2[c] | S156CMM 1[b] | S156CMM 2[c] | S166CMM 1[b] | S166CMM 2[c] | N62CMM 1[b] | N62CMM 2[c] | L217CMM 1[b] | L217CMM 2[c] |
|---|---|---|---|---|---|---|---|---|---|---|---|
| 10 | 0.053 | 0.032 | 0.037 | −0.011 | −0.010 | −0.010 | −0.008 | 0.009 | 0.014 | 0.013 | 0.028 |
| 30 | 0.140 | 0.097 | 0.104 | −0.010 | −0.010 | −0.010 | −0.009 | 0.024 | 0.046 | 0.051 | 0.081 |
| 50 | 0.224 | 0.159 | 0.169 | −0.010 | −0.009 | −0.009 | −0.008 | 0.040 | 0.075 | 0.088 | 0.135 |
| 70 | 0.304 | 0.219 | 0.231 | −0.010 | −0.008 | −0.008 | −0.006 | 0.056 | 0.106 | 0.126 | 0.184 |
| 90 | 0.382 | 0.280 | 0.292 | −0.009 | −0.008 | −0.006 | −0.005 | 0.072 | 0.136 | 0.162 | 0.234 |
| 110 | 0.456 | 0.338 | 0.351 | −0.008 | −0.007 | −0.005 | −0.004 | 0.088 | 0.165 | 0.198 | 0.283 |
| 130 | 0.528 | 0.392 | 0.408 | −0.009 | −0.006 | −0.004 | −0.003 | 0.103 | 0.195 | 0.233 | 0.332 |
| 150 | 0.598 | 0.448 | 0.466 | −0.007 | −0.005 | −0.002 | −0.002 | 0.119 | 0.224 | 0.268 | 0.378 |
| 170 | 0.667 | 0.501 | 0.520 | −0.006 | −0.004 | −0.001 | 0.000 | 0.134 | 0.253 | 0.301 | 0.423 |
| 190 | 0.734 | 0.554 | 0.574 | −0.005 | −0.004 | 0.001 | 0.002 | 0.149 | 0.282 | 0.336 | 0.469 |
| 210 | 0.797 | 0.607 | 0.625 | −0.005 | −0.003 | 0.002 | 0.004 | 0.164 | 0.310 | 0.368 | 0.515 |

TABLE 6-continued

Results for HLADH targeting assay.

| time [s] | Control[a] | SBL-WT 1[b] | 2[c] | S156CMM 1[b] | 2[c] | S166CMM 1[b] | 2[c] | N62CMM 1[b] | 2[c] | L217CMM 1[b] | 2[c] |
|---|---|---|---|---|---|---|---|---|---|---|---|
| 230 | 0.860 | 0.655 | 0.676 | −0.004 | −0.002 | 0.003 | 0.005 | 0.179 | 0.338 | 0.401 | 0.558 |
| 250 | 0.921 | 0.705 | 0.727 | −0.003 | −0.001 | 0.005 | 0.007 | 0.194 | 0.366 | 0.433 | 0.601 |
| 270 | 0.983 | 0.753 | 0.778 | −0.002 | −0.000 | 0.007 | 0.008 | 0.209 | 0.393 | 0.466 | 0.644 |
| 290 | 1.041 | 0.801 | 0.822 | −0.002 | 0.001 | 0.009 | 0.011 | 0.224 | 0.420 | 0.497 | 0.687 |
| 310 | 1.096 | 0.845 | 0.871 | −0.000 | 0.002 | 0.011 | 0.012 | 0.238 | 0.448 | 0.528 | 0.725 |

[a]Average of control measurements without and with decoy protein.
[b]Without decoy protein.
[c]With decoy protein.

Example 3

Targeting and Destroying HLADH in the Presence of Alkaline Phosphatase

In order to direct subtilisins (e.g. SBL) towards various enzyme targets for their degradation we decided to attach specific inhibitors for those enzymes to the subtilisin by our combined site directed mutagenesis chemical modification (CMM) approach as illustrated in FIG. 3.

Our preliminary target has been HLADH, which is inhibited by pyrazoles. The ability of pyrazole-CMMs to selectively destroy HLADH in the presence, and in the absence, of the decoy protein, scrambled RNase A, was also explored (see examples below). This example describes further experiments in the presence of an active enzyme, alkaline phosphatase (AP), as a potential decoy protein. This mimics the in vivo situation where several enzymes are present in a cell, and where we are targeting the destruction of one enzyme (HLADH) while leaving the others (e.g. AP) unaffected Digestion experiments were performed using S166C-pyrazole as a representative CMM. The concentrations of species in the digestion mixtures (when present) were:

| HLADH | 2.62 µM (1.0 eq. of active sites*) |
|---|---|
| AP | 2.74 µM (1.05 eq. of active sites*) |
| S166C-pyrazole | 3.40 µM (1.3 eq. of active sites) |

It is noted that HLADH and AP are both dimers. MWs: HLADH:39492 Da/subunit AP: Da/subunit]

HLADH activity was monitored by periodically withdrawing a portion of the digestion mixture, and assessing the ability of the aliquot to oxidize cyclohexanol to cyclohexanone. The reaction course was monitored by observing the change of NAD$^+$ to NADH at 340 nm as cyclohexanol was oxidized.

Alkaline phosphatase (AP) activity was monitored by periodically withdrawing a portion of the digestion mixture, and assessing the ability of the aliquot to hydrolyze p-nitrophenyl phosphate to inorganic phosphate and p-nitrophenolate. The reaction course was monitored by observing the appearance of p-nitrophenolate at 405 nm.

Results

Six vials were prepared containing S166C-pyrazole, AP and/or HLADH. The HLADH (Table 7) and AP (Table 8) activities of each vial (where applicable) were periodically assayed (see experimental).

TABLE 7

HLADH activity after incubation relative to initial activity.

| | HLADH activity after incubation* % HLADH activity as % of initial (0 h) value | | | | |
|---|---|---|---|---|---|
| vial | 0 h | 1 h | 2 h | 3 h | 72 h |
| AP + HLADH + no S166C-pyrazole | 100 | 117 | 108 | 109 | 114 |
| AP + HLADH + S166C-pyrazole | 100 | 22 | 19 | 16 | 2 |
| HLADH alone | 100 | 108 | 74 | 69 | 89 |
| HLADH + S166C-pyrazole | 100 | 54 | 33 | 30 | 3 |

*HLADH activity was assessed by monitoring the NAD$^+$ to NADH conversion at 340 nm as cyclohexanol was oxidized (see experimental). Incubation at 35° C.

TABLE 8

Alkaline phosphatase activity after incubation relative to initial value.

| | AP activity after incubation * AP activity as % of initial (0 h) value | | | | |
|---|---|---|---|---|---|
| vial | 0 h | 1 h | 2 h | 3 h | 72 h |
| AP + HLADH + no S166C-pyrazole | 100 | 89 | 77 | 91 | 88 |
| AP + HLADH + S166C-pyrazole | 100 | 66 | 82 | 74 | 94 |
| AP alone | 100 | 94 | 94 | # | # |
| AP + S166C-pyrazole | 100 | 85 | 88 | # | # |

* AP activity was assessed by monitoring p-nitropheloate release from p-nitrophenyl phosphate at 405 nm (see experimental). Incubation at 35° C.
AP and AP + S166C-pyrazole experiments were not performed for 3 h and 72 h time points.

The data are also represented graphically in FIG. 6, FIG. 7, FIG. 8, and FIG. 9.

Figure 6:
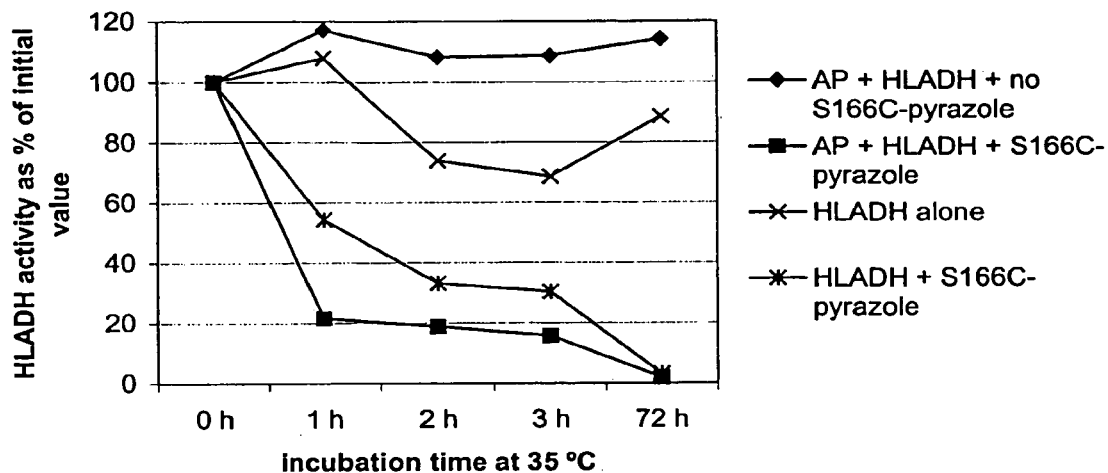
FIG. 6 shows HLADH activity for HLADH/AP mixtures with and without S166C-pyrazole.
Figure 7:
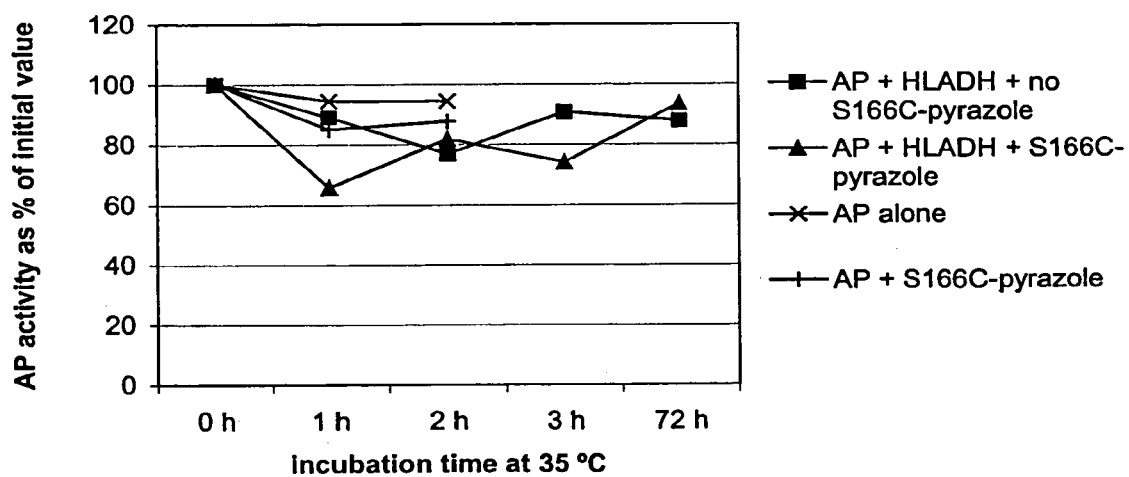
FIG. 7 shows AP activity for HLADH/AP mixtures with and without S166C-pyrazole.
Figure 8:
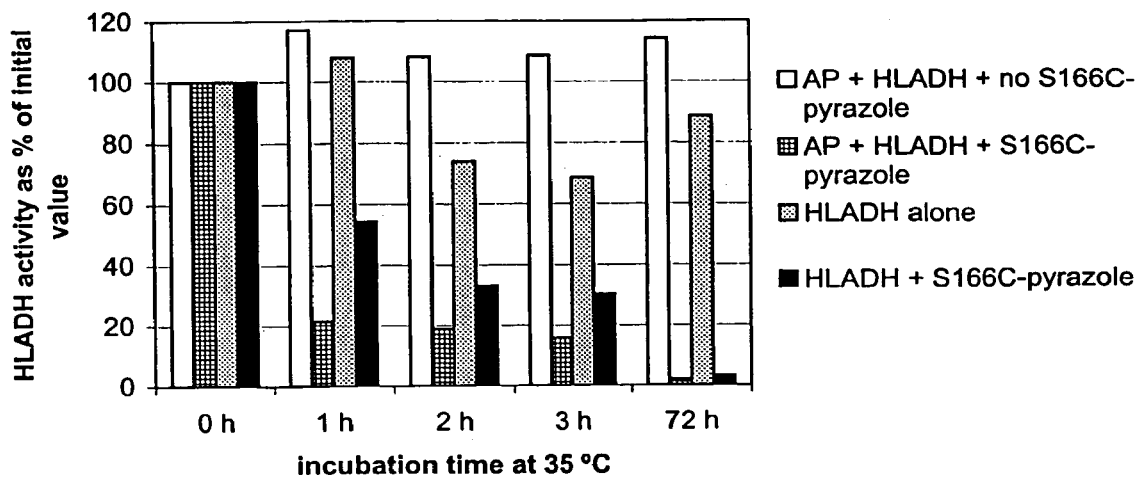
FIG. 8 shows HLADH activity for HLADH/AP mixtures with and without S166C-pyrazole.
Figure 9:
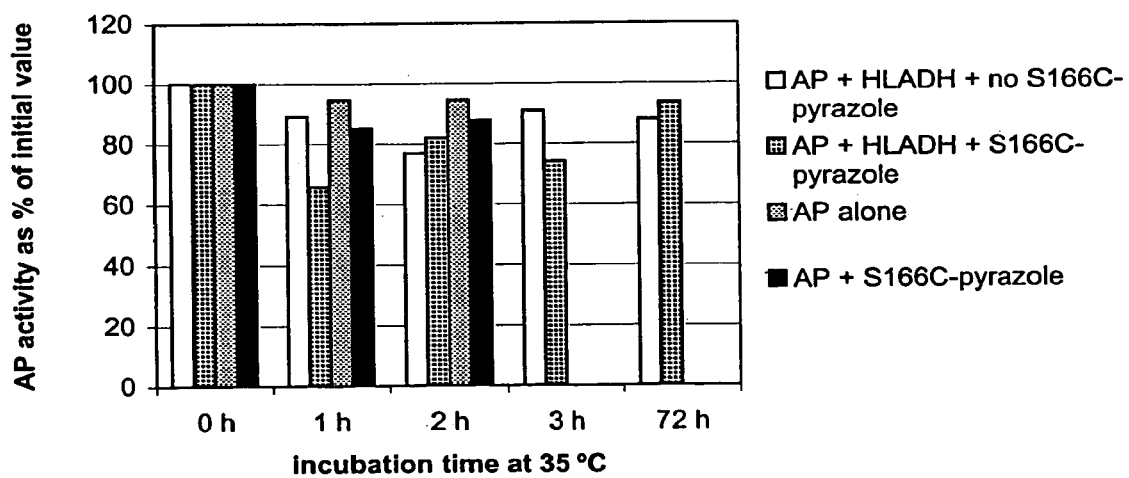
FIG. 9 shows AP activity for HLADH/AP mixtures with and without S166C-pyrazole.
Figure 10:
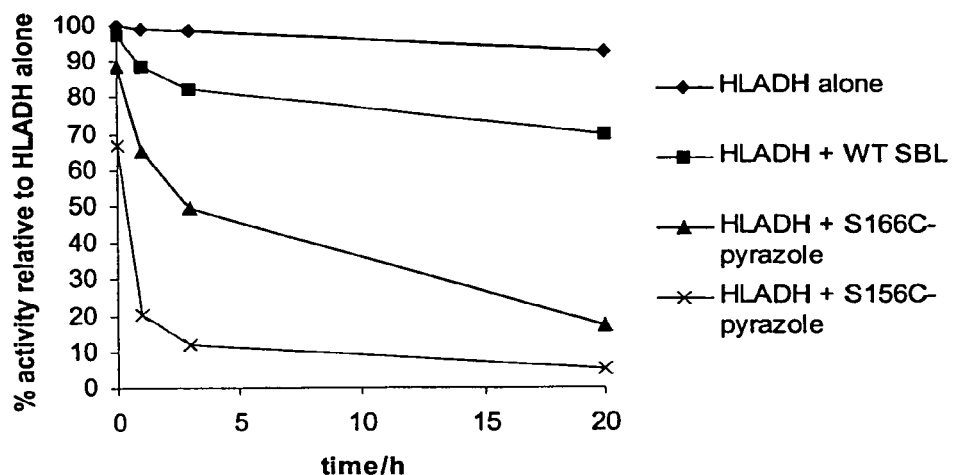
FIG. 10 shows HLADH degradation by substoichiometric pyrazole-CMMs.

The data (Table 7), FIG. 6, and FIG. 8) show that HLADH activity remains constant when assayed alone or in the presence of AP. Also, AP activity is basically unaffected in the presence of S166C-pyrazole CMM (as predicted; Table 2, FIG. 3 and FIG. 5). But the activity of HLADH in the presence of S166C-pyrazole CMM is rapidly and totally lost (Table 1, FIG. 2, and FIG. 4).

Furthermore, AP and HLADH do not interfere with each others activities or catalytic functions (Table 7, Table 8, FIG. 6, FIG. 7, FIG. 8, and FIG. 9)

Experimental Details.

Materials/ pH 9.0 0.1 M Glycine-NaOH Buffer with 1 mM Mg$^{2+}$ and 0.1 mM Zn$^{2+}$ (pH 9.0 Assay Buffer):

Glycine (0.1 mol) was dissolved in water (ca. 800 mL), and $MgCl_2$ (1 mL of a 1 M solution in MQ water) and $ZnCl_2$ (1 mL of a 0.1 M solution in MQ water) were added. The pH was adjusted to 9.0 with ca. 5 M NaOH solution, and the mixture was made up to 1 L.

pH 7.4 0.05 M TRIS-HCl Buffer (pH 7.4 TRIS):

A solution of TRIS was neutralized to pH 7.4, and was then diluted to 0.05 M.

pH 7.8 0.05 M Triethanolamine-HCl Buffer with 3 M NaCl, 0.1 mM $Mg^{2+}$ and 0.01 mM $Zn^{2+}$ (pH 7.8 Buffer):

Triethanolamine (0.05 moles, 7.5 g), NaCl (3 moles, 175.5 g), MgCl2 (0.1 mL of 1 M solution) and ZnCl2 (0.1 mL of 1M solution) were dissolved in MQ water (ca. 900 mL). The pH was adjusted to 7.4 with ca 2N HCl and the resulting solution made up to 1 L.

pH 8.6 ca. 0.1 M TRIS-HCl Buffer with 0.05% Tween, 1 mM and 0.1 mM $Zn^{2+}$ (pH 8.6 Buffer):

$MgCl_2$ (0.1 mL of a 1 M solution in MQ water) and $ZnCl_2$ (0.1 mL of a 0.1 M solution in MQ water) were added to a 100 mL volumetric flask, and the flask was made up to the mark with pH 8.6 0.1 M TRIS-HCl buffer containing 0.05% Tween.

HLADH Solution:

Horse liver alcohol dehydrogenase (Sigma A-9589, EC 1.1.1.1, 8 mg of ca. 50% w/w protein) was dissolved in pH 7.4 TRIS (0.8 mL) to give a 10 mg/mL solution.

Alkaline Phosphatase (AP) Solution:

Alkaline phosphatase (Boehringer Mannheim 713 023, EC 3.1.3.1, ca. 950 µL as received in 50% w/v glycerol:buffer) was diluted with pH 7.8 buffer (ca. 15 mL), and was concentrated at 4° C. to 10-20% of its original volume using a Centriprep concentrator. A further 15 mL of pH 7.8 buffer was added, and the sample was concentrated once more. This process was repeated a further 3 times using pH 9.0 assay buffer for dilutions. After the third concentration the concentrate (ca. 1.85 mL) was collected and was stored on ice. This procedure was necessary to remove glycerol, which is a substrate for HLADH.

$NAD^+$ Solution:

33.2 mg/mL of $NAD^+$ was dissolved in pH 9.0 assay buffer.

Cyclohexanol Solution:

10 mg/mL of cyclohexanol in pH 9.0 assay buffer.

p-Nitrophenyl Phosphate Solution (PNPP Solution):

A tablet containing 20 mg of p-nitrophenyl phosphate (Sigma N-2765) was dissolved in pH 8.6 buffer (20 mL).

Pyrazole-CMM:

S166C-pyrazole (1.76 mg/mL) in MES storage buffer (pH 5.8 10 mM MES, 2 mM $CaCl_2$).

Assaying HLADH Activity

Six eppendorf vials were filled as shown in Table 9:

The vials were incubated at 35° C. for the times indicated in the tables below. Aliquots were periodically withdrawn in order to assay the HLADH and alkaline phosphatase activities as time progressed.

A portion of solution (65 µL) was withdrawn from an incubation vial and was then injected into a micro-cuvette containing pH 9.0 assay buffer (200 µL). The cuvette was incubated at 25° C. for 2 minutes, and then cyclohexanol solution (30 µL) was added. The absorbance at 340 nm was then monitored for 300 s, and the O.D. change per second up to 0.2 absorbance units was recorded.

Assaying Alkaline Phosphatase Activity

A portion (20 µL) was withdrawn from an incubation vial and was then injected into pH 8.6 buffer (980 µL). The mixture was vortexed. 10 µL, was the removed from the mixture, and was injected into a cuvette containing 990 µL of PNPP solution incubated at 25° C. The absorbance change at 405 nm was monitored for 150 s, and the O.D. change per second up to 1 Absorbance unit was recorded.

Example 4

Targeting HLADH with Substoichiometric Pyrazole-CMMs

Stoichiometry:

Experiments were performed using 2 eq. HLADH dimer (4 eq. active sites) to 1 eq. pyrazole-CMM or WT-SBL as illustrated in Table 10.

TABLE 10

| Stoichiometry. | |
| --- | --- |
| HLADH (ca. 79 kD for the dimer) | SBL or pyrazole-CMM (ca. 27 kD) |
| 2 eq. dimer (4 eq. active sites) 1.42 µM dimer (2.84 µM active sites) | 1 eq. (SBL/CMM is a monomer) 0.71 µM (SBL/CMM is a monomer) |

Conditions:

The reactions were performed at pH 9.0, 0.1 M glycine-NaOH with 0.005% Tween 80, 35° C.

Results:

HLADH solutions were incubated in the presence of WT-SBL, S166C-pyrazole or S156C-pyrazole. A control experiment was performed in the absence of any SBL-based enzyme (HLADH alone). The HLADH activities of the four mixtures were periodically assayed (see experimental)—see Table 11.

TABLE 9

Setup for HLADH activity assay.

| vial | Contents label | Assay buffer/µL | $NAD^+$/µL | HLADH/µL | AP/µL | pyrazole-CMM/µL |
| --- | --- | --- | --- | --- | --- | --- |
| 1 | AP + HLADH no CMM | 100 | 150 | 15 | 435 | 0.0 |
| 2 | AP + HLADH + CMM | 61 | 150 | 15 | 435 | 39.0 |
| 3 | AP only | 26.5 | 0 | 0 | 43.5 | 0.0 |
| 4 | HLADH only | 535 | 150 | 15 | 0 | 0.0 |
| 5 | HLADH + CMM | 496 | 150 | 15 | 0 | 39.0 |
| 6 | AP + CMM | 22.6 | 0 | 0 | 43.5 | 39.0 |

CMM was S166C-pyrazole.

TABLE 11

HLADH activities after incubation
with or without pyrazole-CMMs.

% HLADH activity compared to the initial
"HLADH alone" value*

| time/h | HLADH alone | HLADH + WT SBL | HLADH + S166C-pyrazole | HLADH + S156C-pyrazole |
|---|---|---|---|---|
| 0 | 100 | 97 | 89 | 67 |
| 1 | 99 | 89 | 65 | 21 |
| 3 | 98 | 82 | 49 | 12 |
| 20 | 93 | 70 | 17 | 5 |

*HLADH activity was assessed by monitoring the conversion of $NAD^+$ to NADH at 340 nm as cyclohexanol was oxidized at 25° C., pH 9.0 (see experimental).

Discussion:

The initial drop in HLADH activity caused on addition of the pyrazole-CMMs reflects the ability of the CMMs to target and thus inhibit HLADH. S156C-pyrazole and, to a lesser extent, S166C-pyrazole clearly cause dramatic reductions in HLADH activity on incubation. The pyrazole-CMMs were used in less than stoichiometric amounts with respect to HLADH—4 eq. HLADH active sites: 1 eq. pyrazole-CMM—but they rapidly caused a greater than 25% diminution of HLADH activity. Indeed, in the case of S156C-pyrazole, HLADH activity is seen to drop from 67% to 5% over 20 h, representing a 13.5-fold reduction of HLADH activity over-and-above the maximum inhibitory effect of the pyrazole moiety. WT-SBL causes a mere 1.4-fold reduction of HLADH activity over the same 20 h period, despite its enhanced amidase specific activity when compared to the pyrazole-CMMs.

Summary:

Pyrazole-CMMs are seen to target and to catalytically destroy HLADH.

Experimental Materials:

pH 9.0 0.1 M Glycine-NaOH Buffer with 0.005% Tween 80 (pH 9.0 Assay Buffer:

Glycine (0.1 mol) was dissolved in water (ca. 800 mL). A solution of Tween 80 (50 mL of a 0.1% v/v in MQ water) was added, and the pH was adjusted to 9.0 with ca. 5 M NaOH solution. The mixture was made up to 1 L with MQ water.

pH 7.4 0.05 M TRIS-HCl Buffer (pH 7.4 TRIS):

TRIS (302.9 mg, 2.5 mmol) was dissolved in MQ water (ca. 40 mL). The pH was adjusted to 7.4 with ca. 1 M HCl solution, and the volume of the mixture was made up to 50 mL with MQ water.

HLADH Solution:

Horse liver alcohol dehydrogenase (Sigma A-9589, Lot 58H7004, EC 1.1.1.1, 8.45 mg of 52.4% w/w protein—according to manufacturer's Biuret titration) was dissolved in pH 7.4 TRIS (0.845 mL) to give a 5.24 mg/mL solution of active protein.

Checking HLADH Concentration:

HLADH (50 μL) solution was added to pH 7.4 TRIS (450 μL) to give a tenfold diluted solution. Bradford (Bio-Rad) protein determination was performed on this diluted sample, and yielded a protein concentration of 0.616 mg/mL. This translates to a concentration of 6.16 mg/mL in the original HLADH stock. We assume the lower value of 5.24 mg/mL to be correct in order to ensure that protein concentration is more likely to be under—rather than overestimated.

$NAD^+$ Solution:

$NAD^+$ (332 mg) was dissolved in pH 9.0 assay buffer (10 mL) to give a 33.2 mg/mL solution.

Cyclohexanol Solution:

Cyclohexanol (100 mg) was dissolved in pH 9.0 assay buffer (10 mL) to give a 10 mg/mL solution.

Subtilisin Solutions:

WT-SBL (1.88 mg of dry powder, 73% w/w active protein) was dissolved in pH 5.8, 10 mM MES, 2 mM $CaCl_2$ "storage buffer" (500 μL) to give a 2.74 mg/mL solution of active WT-SBL. S156C-pyrazole and S166C-pyrazole were previously titrated with PMSF: their concentrations were 2.5 mg/mL and 3.62 mg/ml respectively.

Experimental Details:

HLADH Hydrolysis Assay:

Four 5 mL falcon tubes were filled according to Table 12

TABLE 12

Preparation of reaction mixtures.

| Tube no. | pH 9.0 assay buffer[a] (μL) | $NAD^+$ solution[b] (μL) | HLADH solution[c] (μL) | SBL/CMM[d] |
|---|---|---|---|---|
| 1 | 2140 | 600 | 60 | not added |
| 2 | 2120 | 600 | 60 | WT-SBL 19.52 μL |
| 3 | 2125 | 600 | 60 | S166C-pyrazole 14.80 μL |
| 4 | 2119 | 600 | 60 | S156C-pyrazole 21.4 μL |

[a] 0.1M glycine-NaOH with 0.005% Tween 80.
[b] 33.2 mg/mL in pH 9.0 assay buffer.
[c] 5.24 mg/mL active HLADH.
[d] Concentrations: WT-SBL, 2.74 mg/mL; S166C-pyrazole, 3.62 mg/mL; S156C-pyrazole, 2.5 mg/mL.

The tubes were kept on ice until the HLADH activity of each tube had been assayed in order to give a "time zero" value for each tube (see below for assay protocol). The tubes were then incubated on a water bath at 35° C. Periodically, 700 μL, of reaction mixture with drawn from each falcon tube, the aliquots were placed in individual eppendorf tubes, and the eppendorf tubes were stored on ice. The content of each eppendorf tube was then assayed for HLADH activity (see below).

Assaying HLADH Activity:

A portion of reaction mixture (650 μL) was injected into a cuvette containing pH 9.0 assay buffer (2.00 mL). The cuvette was incubated at 25° C. for 2 minutes, and then cyclohexanol solution (300 μL) was added. After a 10 s delay, the absorbance at 340 nm was monitored for 300 s. The O.D. change per second up to 0.2 absorbance units was used to calculate an initial rate.

Results.

The results are summarized in Table 13.

TABLE 13

HLADH activities during HLADH hydrolysis
experiment (raw data).

(slope at 340 nm in units of O.D. units per second) × 1000*

| incubation time/h | HLADH alone (tube 1) | HLADH + WT SBL (tube 2) | HLADH + S166C-pyrazole (tube 3) | HLADH + S156C-pyrazole (tube 4) |
|---|---|---|---|---|
| 0 | 5.14 | 4.99 | 4.36 | 3.43 |
| 1 | 5.07 | 4.56 | 3.36 | 1.05 |
| 3 | 5.05 | 4.22 | 2.53 | 0.61 |
| 20 | 4.76 | 3.58 | 0.88 | 0.26 |

*The O.D. change up to 0.2 absorbance units was used to calculate these numbers.

Example 5

Targeting HLADH in the Presence of Alkaline Phosphatase Using S156C- and S166C-Pyrazole-CMMs at Substoichiometric Levels of CMMs Stoichiometry Experiments were performed using 2 eq. HLADH dimer (4 eq. active sites) to 1 eq. pyrazole-CMM or WT-SBL; alkaline phosphatase from calf intestine was used as an "active-enzyme" decoy protein in all experiments. Alkaline phosphatase from calf intestine is composed of two isozymes of molecular weights 66 and 68 kD per subunit. Both isozymes are dimers, thus we assume an approximate molecular weight of 134 kD for each dimer in our calculations. The stoichiometries used are shown in Table 14.

TABLE 14

Stoichiometries used HLADH targeting assay.

| HLADH (ca. 79 kD for the dimer) | Alkaline phosphatase (AP) (ca. 134 kD for each dimer) | WT-SBL or Pyrazole-CMM (ca. 27 kD) |
|---|---|---|
| 2 eq. dimer (4 eq. active sites) | 2 eq. dimer (4 eq. active sites) | 1 eq. (SBL/CMM is a monomer) |
| 1.42 µM dimer (2.84 µM active sites) | 1.42 µM dimer (2.84 µM active sites) | 0.71 µM (SBL/CMM is a monomer) |

Conditions.

pH 9.0, 0.1 M glycine-NaOH with 0.005% Tween 80, 1 mM $MgCl_2$ and 0.1 mM $ZnCl_2$, 35° C.

Four experiments were performed simultaneously: all four experiments were performed with HLADH and AP present in each of the four vials (i.e. they are in direct competition as substrates for hydrolysis). In addition, each vial contained one of buffer (no SBL added), WT-SBL, S156C-pyrazole or S166C-pyrazole.

Figure 11:
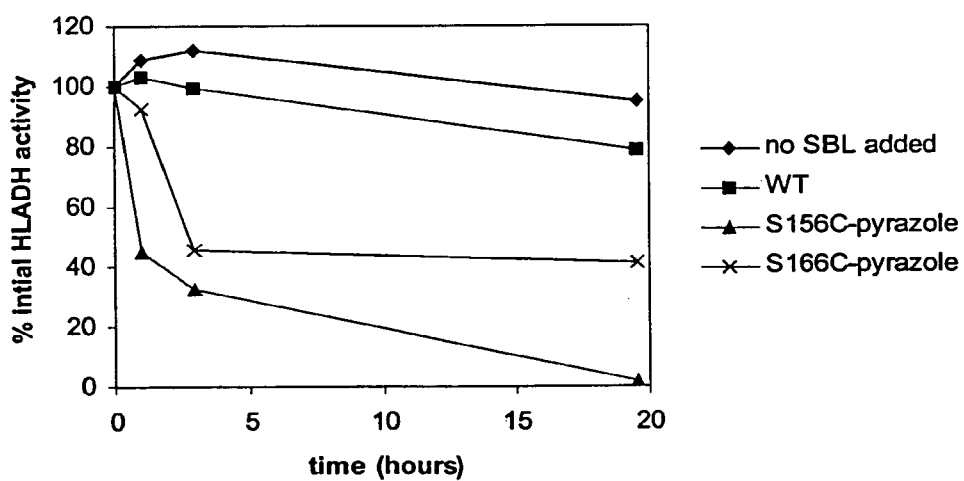
FIG. 11 shows HLADH degradation by pyrazole-CMMs in the presence of alkaline phosphatase
Figure 12:
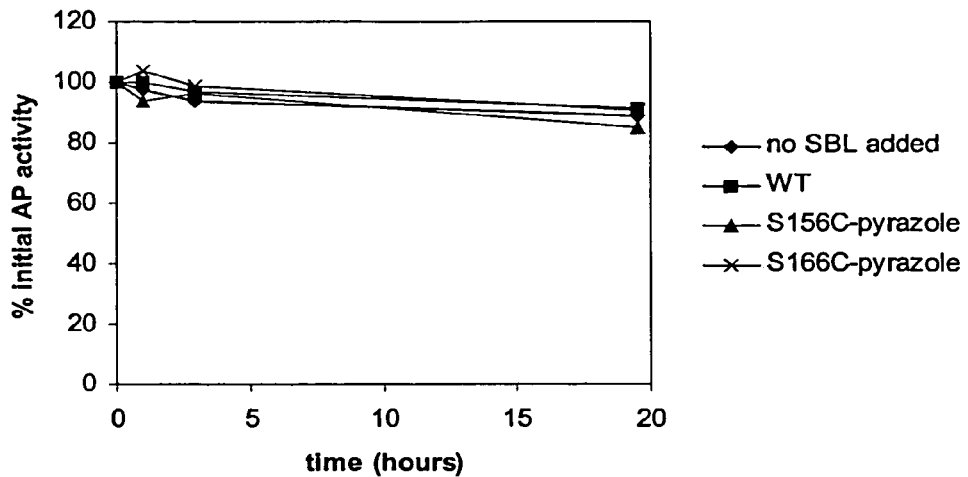
FIG. 12 illustrates alkaline phosphatase degradation by pyrazole-CMMs in the presence of HLADH.

Results:

Vials that each contained a mixture of HLADH and alkaline phosphatase were incubated in the presence of WT-SBL, S166C-pyrazole or S156C-pyrazole. A control experiment was performed in the absence of any SBL-based enzyme (no SBL). The HLADH and Alkaline phosphatase activities of the four mixtures were periodically assayed in order to determine the fidelity of the CMMs toward HLADH vs. Alkaline phosphatase (see experimental)—see Table 15, Table 16, FIG. 11 and FIG. 12. (Data are also presented relative to "no SBL added" time=0 h values in the appendix to demonstrate the inhibitory effects of the pyrazole CMMs on HLADH)

TABLE 15

HLADH activities after incubation with or without pyrazole-CMMs.

% HLADH activity* compared to the time = 0 h value for each experiment
SBL derivative (if added)

| time/h | no SBL | WT-SBL | S156C-pyrazole | S166C-pyrazole |
|---|---|---|---|---|
| | 100 | 100 | 100 | 100 |
| 1 | 109 | 103 | 45 | 93 |
| 3 | 112 | 99 | 33 | 46 |
| 19.5 | 95 | 79 | 2 | 41 |

*HLADH activity was assessed by monitoring the conversion of $NAD^+$ to NADH at 340 nm as cyclohexanol was oxidized at 25° C., pH 9.0 (see experimental).

TABLE 16

AP activities after incubation with or without pyrazole-CMMs.

% alkaline phosphatase activity* compared to the time = 0 h value for each experiment
SBL derivative (if added)

| time/h | no SBL | WT-SBL | S156C-pyrazole | S166C-pyrazole |
|---|---|---|---|---|
| 0 | 100 | 100 | 100 | 100 |
| 1 | 98 | 100 | 93 | 104 |
| 3 | 94 | 97 | 96 | 99 |
| 19.5 | 88 | 91 | 85 | 90 | alkaline phosphatase activity was assessed by monitoring p-nitropheloate release from p-nitrophenyl phosphate at 405 nm (see experimental).

Discussion.

Alkaline phosphatase is clearly not very susceptible to hydrolysis by WT-SBL or Pyrazole-CMMs. HLADH activity is not significantly diminished on incubation in the absence of SBL or in the presence of WT-SBL. However, in the presence of S156C-pyrazole or S166C-pyrazole HLADH activity is seen to diminish rapidly.

Summary.

Pyrazole-CMMs are seen to target and to catalytically destroy HLADH in the presence of alkaline phosphatase. Alkaline phosphatase is unaffected by the hydrolytic action of WT-SBL and Pyrazole-CMMs.

Experimental

Materials pH 9.0 0.1 M Glycine-NaOH Buffer with 0.005% Tween 80, 1 mM $Mg^{2+}$ and 0.1 mM $Zn^{2+}$ (pH 9.0 Assay Buffer with Tween, $Mg^{2+}$ and $Zn^{2+}$):

Glycine (0.1 mol) was dissolved in water (ca. 800 mL). Magnesium chloride solution (1 mL of a 1 M solution) and zinc chloride solution (1 mL of a 0.1 M solution) were added to the glycine solution. A solution of Tween 80 (50 mL of a 0.1% v/v in MQ water) was added to the mixture, and the pH was adjusted to 9.0 with ca. 5 M NaOH solution. The mixture was made up to 1L with MQ water.

pH 9.0 0.1 M Glycine-NaOH Buffer with 1 mM Mg2+ and 0.1 mM Zn2+ (pH 9.0 Dialysis Buffer).

Glycine (0.1 mol) was dissolved in water (ca. 800 mL). Magnesium chloride solution (1 mL of a 1 M solution) and zinc chloride solution (1 mL of a 0.1 M solution) were added to the glycine solution, and the of the mixture pH was adjusted to 9.0 with ca. 5 M NaOH solution. The mixture was made up to 1 L with MQ water.

pH 7.4 0.05 M TRIS-HCl Buffer (pH 7.4 TRIS)

TRIS (302.9 mg, 2.5 mmol) was dissolved in MQ water (ca. 40 mL). The pH was adjusted to 7.4 with ca. 1 M HCl solution, and the volume of the mixture was made up to 50 mL with MQ water.

pH 7.4 0.05 M TRIS-HCl Buffer with 1 mM Mg2+ and 0.1 mM Zn2+ (pH 7.4 Dialysis Buffer)

TRIS (6.057 g, 0.05 mol) was dissolved in MQ water (ca. 800 mL). Magnesium chloride solution (1 mL of a 1 M solution) and zinc chloride solution (1 mL of a 0.1 M solution) were added to the TRIS solution, and the of the mixture pH was adjusted to 7.4 with ca. 1 M HCl solution. The mixture was made up to 1 L with MQ water.

pH 8.6 ca. 0.1 M TRIS-HCl Buffer with 0.05% Tween, 1 mM Mg2+ and 0.1 mM Zn2+ (pH 8.6 Buffer)

$MgCl_2$ (0.1 mL of a 1 M solution in MQ water) and $ZnCl_2$ (0.1 mL of a 0.1 M solution in MQ water) were added to a 100 mL volumetric flask, and the flask was made up to the mark with pH 8.6 0.1 M TRIS-HCl buffer containing 0.05% Tween (standard amidase kinetics buffer).

HLADH Solution

Horse liver alcohol dehydrogenase (Sigma A-9589, Lot 58H7004, EC 1.1.1.1, 3.77 mg of 52.4% w/w protein-according to manufacturer's Biuret titration) was dissolved in pH 7.4 TRIS (0.377 mL) to give a 5.24 mg/mL solution of active protein.

NAD+ Solution $NAD^+$ (39.15 mg) was dissolved in pH 9.0 assay buffer (1.179 mL) to give a 33.2 mg/mL solution.

Cyclohexanol Solution

Cyclohexanol (100 mg) was dissolved in pH 9.0 assay buffer (10 mL) to give a 10 mg/mL solution.

Subtilisin Solutions.

WT-SBL (1.88 mg of dry powder, 73% w/w active protein) was dissolved in pH 5.8, 10 mM MES, 2 mM $CaCl_2$ "storage buffer" (500 μL) to give a 2.74 mg/mL solution of active WT-SBL. This solution was diluted four-fold with pH 5.8, 10 mM MES, 2 mM $CaCl_2$ "storage buffer" to give a 0.685 mg/mL solution.

S156C-pyrazole and S166C-pyrazole were previously titrated with PMSF: their concentrations were 2.5 mg/mL and 3.62 mg/mL respectively. These stock solutions were diluted four-fold with pH 5.8, 10 mM MES, 2 mM $CaCl_2$ "storage buffer" to give 0.63 mg/mL and 0.91 mg/mL solutions of S156C-pyrazole and S166C-pyrazole, respectively.

p-Nitrophenyl Phosphate Solution (PNPP Solution).

Two tablets, each containing 20 mg of p-nitrophenyl phosphate (Sigma N-2765), were dissolved in pH 8.6 buffer (40 mL). The solution was stored on ice.

Dialysis of Alkaline Phosphatase.

Two vials of Calf intestinal alkaline phosphatase (Sigma P-7923, Lots 128H1210 and 17H0204) were mixed with pH 7.4 dialysis buffer (0.5 mL). The mixture was dialysed against 2×500 mL pH 7.4 dialysis buffer (1×4 h then 1× overnight) and then 2×500 mL pH 9.0 dialysis buffer (2×2 h). The total protein concentration was then determined using the Bradford technique (Bio-Rad), and was found to be 2.36 mg/mL.

Experimental Details

Four 1.5 mL Eppendorf tubes were filled according to Table 22.

TABLE 17

Preparation of reaction mixtures.

| Tube no. | pH 9.0 assay buffer[a] (μL) | NAD+ solution[b] (μL) | HLADH solution[c] (μL) | AP solution[d] (μL) | SBL/CMM[e]- if added |
|---|---|---|---|---|---|
| 1 | 479 | 150 | 15 | 56.4 | Nothing added |
| 2 | 459 | 150 | 15 | 56.4 | WT-SBL 19.52 μL |

TABLE 17-continued

Preparation of reaction mixtures.

| Tube no. | pH 9.0 assay buffer[a] (μL) | NAD+ solution[b] (μL) | HLADH solution[c] (μL) | AP solution[d] (μL) | SBL/CMM[e]- if added |
|---|---|---|---|---|---|
| 3 | 457 | 150 | 15 | 56.4 | S156C-pyrazole 21.4 μL |
| 4 | 464 | 150 | 15 | 56.4 | S166C-pyrazole 14.80 μL |

[a]0.1M glycine-NaOH with 0.005% Tween 80, 1 mM $MgCl_2$ and 0.1 mM $ZnCl_2$.
[b]33.2 mg/mL in pH 9.0 assay buffer with Tween, $Mg^{2+}$ and $Zn^{2+}$.
[c]5.24 mg/mL active HLADH.
[d]2.36 mg/mL alkaline phosphatase (Bradford).
[e]Concentrations: WT-SBL, 0.685 mg/mL; S166C-pyrazole, 0.91 mg/mL; S156C-pyrazole, 0.63 mg/mL.

The tubes were kept on ice until aliquots had been withdrawn from each tube to establish initial HLADH and alkaline phosphatase activities. These activities were used to give "time zero" values for each tube (see below for assay protocols). The tubes were then incubated on a water bath at 35° C. Periodically, aliquots of reaction mixture were withdrawn from each eppendorf tube in order to assay HLADH and alkaline phosphatase activities.

Assaying HLADH Activity

A portion of solution (65 μL) was withdrawn from an incubation vial and was then injected into a micro-cuvette containing pH 9.0 assay buffer (200 μL). The cuvette was incubated at 25° C. for 2 minutes, and then cyclohexanol solution (30 μL) was added. The absorbance at 340 nm was then monitored for 120 s, and the O.D. change per second up to 0.2 absorbance units was recorded.

Assaying Alkaline Phosphatase Activity

A portion (10 μL) was withdrawn from an incubation vial and was then injected into pH 8.6 buffer (490 μL). The mixture was vortexed. 10 μL was the removed from the mixture, and was injected into a cuvette containing 990 μL of PNPP solution incubated at 25° C. The absorbance change at 405 nm was monitored for 120 s, and the O.D. change per second up to 1.0 Absorbance unit was recorded.

Results.

The results are illustrated in Table 18 and Table 19

TABLE 18

HLADH activities during HLADH/alkaline phosphatase competitive hydrolysis experiments (raw data).

| incubation time/h | (slope at 340 nm in units of O.D. units per second) × 1000* | | | |
|---|---|---|---|---|
| | no SBL | WT-SBL | S156C-pyrazole | S166C-pyrazole |
| 0 | 5.13 | 5.09 | 2.76 | 4.58 |
| 1 | 5.57 | 5.25 | 1.25 | 4.25 |
| 3 | 5.73 | 5.05 | 0.90 | 2.09 |
| 19.5 | 4.88 | 4.01 | 0.06 | 1.88 |

*The O.D. change up to 0.2 absorbance units was used to calculate these numbers.

TABLE 19

Alkaline phosphatase activities during HLADH/alkaline phosphatase competitive hydrolysis experiments (raw data).

| incubation time/h | (slope at 405 nm in units of O.D. units per second) × 1000* | | | |
|---|---|---|---|---|
| | no SBL | WT-SBL | S156C-pyrazole | S166C-pyrazole |
| 0 | 8.04 | 7.78 | 8.05 | 7.48 |
| 1 | 7.85 | 7.79 | 7.52 | 7.77 |
| 3 | 7.56 | 7.52 | 7.76 | 7.41 |
| 19.5 | 7.11 | 7.09 | 6.83 | 6.77 |

*The O.D. change up to 1.0 absorbance units was used to calculate these numbers.

Example 5

Synthesis of Carbohydrate Modified Serine Hydrolases

The contamination of animal feed by certain lectins substantially reduces their nutritional value (Gatel (1994) *Animal Feed Sci. Technl* 45: 317-348; Mogridge et al. (1996) *J. Animal Sci.* 74: 1897-1904; Pusztai et al. (1997) *G. Brit. J. Nutrition* 77, 933-945). In particular contamination of soy-based feeds by mannose-binding lectins prevents the effective use of crude feed without substantial purification.

Figure 13:
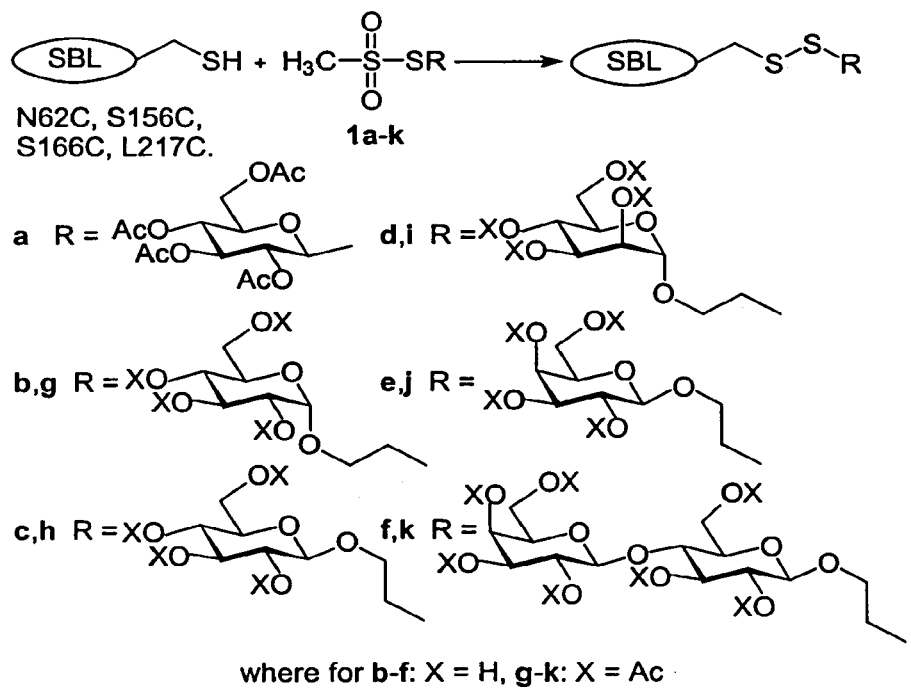
FIG. 13 shows 11 mono- and disaccharide methanethiosulfonates that were prepared.

With the aim of preparing glycosylated CMMs useful for the we have prepared 11 mono- and disaccharide methanethiosulfonates (FIG. 13) bearing different carbohydrates which allow the preparation of a large number glycosylated CMMs for use, e.g. as lectin-directed proteases. A number of chemically modified enzymes having chemically conjugated carbohydrate moieties are described in PCT Application WO 00001712 entitled "Chemically modified proteins with a carbohydrate moiety.

Example 6

Targeted Lectin Degradation Assay using Mannosylated-SBL

This example describes a highly effective lectin assay that has allowed us to start a screen of the ability of sugar-modified CMMs to degrade the lectin Concanavalin A in the manner shown schematically below (FIG. 14A, FIG. 14B, and FIG. 14C).

S156C-sugar CMMs which contain surface exposed sugar groups were chosen initially. For each assay, biotinylated lectin was incubated with glyco-CMM and compared with samples incubated with GG36-WT. To allow comparison, equal amounts of active enzyme were used. These samples were also incubated both with and without the decoy protein disulfide scrambled-RNaseA, in order to measure the selectivity of these enzymes for the lectin over the decoy.

Small protein fragments (<3000 Da), the products of proteolysis, were separated from larger proteins using a size-exclusion membrane. Fragments of lectin are labeled with biotin whereas non-lectin fragments are unlabelled. By monitoring both the levels of biotinylated fragments released, using a HABA/Avidin test, and total protein fragment concentration, using $A_{280}$, we can qualitatively judge both the amount of lectin degradation and selectivity for lectin over decoy. The results of initial screens are shown in FIG. 15A and FIG. 15B, FIG. 15C, and FIG. 15D.

Figure 15A:
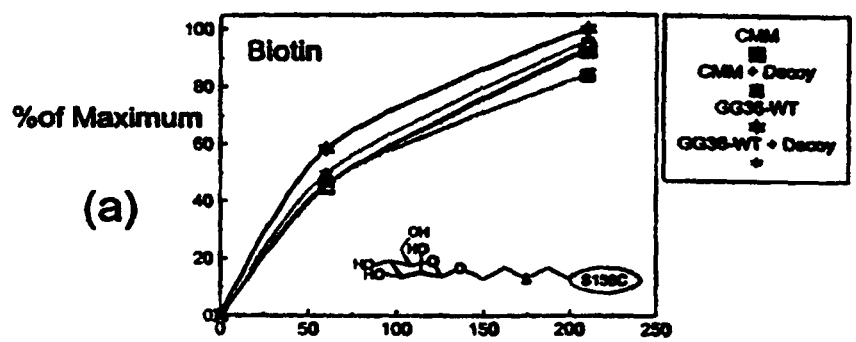
FIG. 15A, FIG. 15B, FIG. 15C, and FIG. 15D illustrate time course plots of the formation of <3000 MW protein fragments during a lectin assay.
Figure 15B:
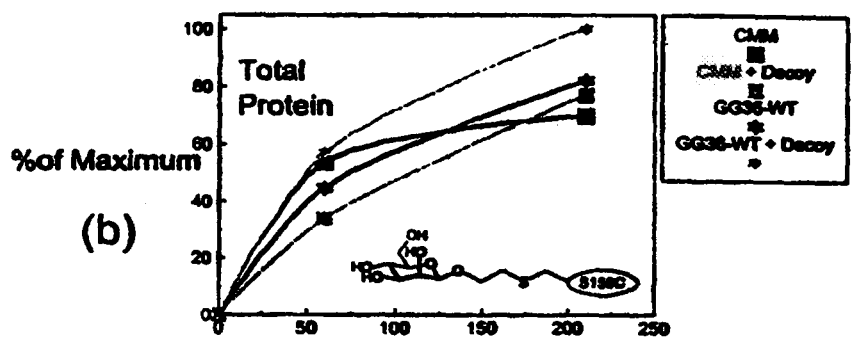
Figure 15C:
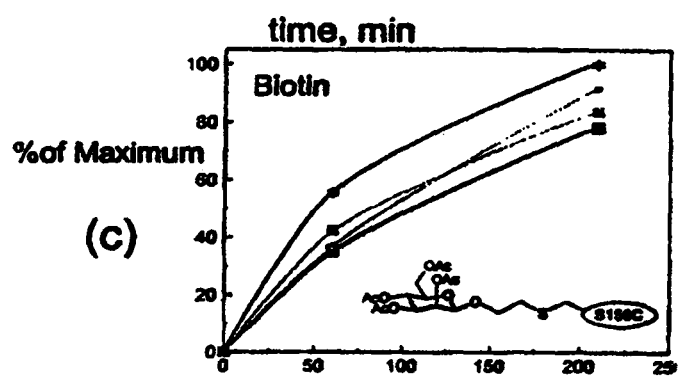
Figure 15D:
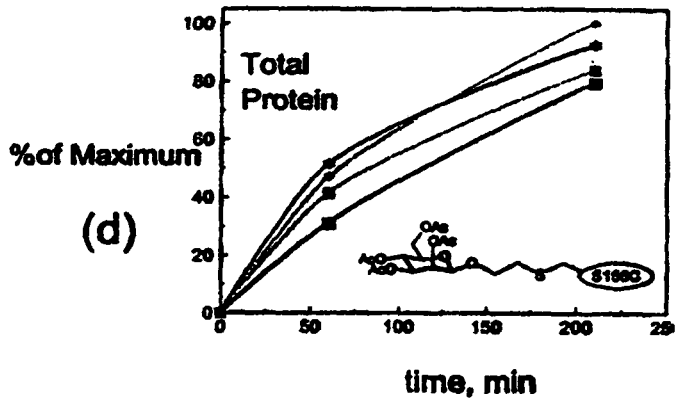

It is clear that both GG36-WT and the two CMMs S156C-S-EtMan (FIG. 15A and FIG. 15B) and S156C-S-EtMan (Ac)₄ (FIG. 15C, and FIG. 15D are able to rapidly degrade lectin concanavalin A. The higher rate of hydrolysis by GG36-WT is consistent with its higher $k_{cat}/K_M$ value towards Suc-AAPF-pNA ($k_{cat}/K_M$ for GG36 of 209 s$^{-1}$ mM$^{-1}$, as compared with 112 and 85 s$^{-1}$ mM$^{-1}$ for S156C-S-Et-Man and S156C-S-EtMan(Ac)₄, respectively).

A more detailed examination of FIG. 15A-FIG. 15D reveals that a) Released Biotin levels (indicating lectin degradation) are similar to each other. The presence of decoy reduces slightly both the level of GG36-WT and S156-S-EtMan degradation.

b) GG36-WT in the presence of decoy produces 18% more total protein after 210 min. than without. In contrast, S166C-S-EtMan in the presence of decoy produces only 7% more total protein—therefore the greater selectivity of S156C-S-EtMan reduces total protein absorption changes by 11%.

c) Again, released Biotin levels (indicating lectin degradation) are similar to each other.

d) Both GG36-WT and S156C-S-EtManAc produce more total protein after 210 min. in the presence of decoy than without (under these conditions, 7% more for WT and 5% more for S156C-S-EtManAc). These similar levels indicate little or no selectivity of S156C-S-EtManAc for Concanavalin A.

This slight but exciting creation of selectivity of S156C-S-EtMan is consistent with the introduction of an unprotected mannose group—since this is the natural ligand of concanavalin A. The lower/lack of selectivity shown by fully protected S156C-S-EtMan(Ac)₄ is consistent with the importance of the unprotected hydroxyl groups of mannose for correct recognition by lectins.

Experimental

Ten disposable eppendorf vials were filled as shown in Table 20.

TABLE 20

Lectin assay design.

| Vial Number | Lectin-Assay Buffer[a]/μL | Concanavalin A[b]/μL | Decoy Protein[c]/μL | Enzyme/ μL |
|---|---|---|---|---|
| 1 | 900 | 100 | — | — |
| 2 | 890 | 100 | 10 | — |
| 3 | 900 | 100 | — | 10 of glyco-CMM |
| 4 | 900 | 100 | — | 10 of glyco-CMM |
| 5 | 890 | 100 | 10 | 10 of glyco-CMM |
| 6 | 890 | 100 | 10 | 10 of glyco-CMM |
| 7 | 900 | 100 | — | 10 of WT[d] |
| 8 | 900 | 100 | — | 10 of WT[d] |
| 9 | 890 | 100 | 10 | 10 of WT[d] |
| 10 | 890 | 100 | 10 | 10 of WT[d] |

[a] Lectin-Assay Buffer: 20 mM Tris•HCl, 2 mM CaCl₂, pH 8.6.
[b] 5 mg/mL solution of Biotinylated Concanavalin A (Vector Laboratories) in Milli Q water.
[c] 5 mg/mL solution of Ribonuclease A with Scrambled Disulfide Bonds (Sigma) in Milli Q water.
[d] Solution of lyophilized GG36-WT diluted to the same concentration as the glyco-CMM (as determined by PMSF) in 20 mM MES, 1 mM CaCl₂, pH 5.5.

These solutions were warmed to 35° C. in a thermostat-controlled water bath. After the indicated incubation time, the contents of the appropriate vials were each placed in the top of a Centricon-SR3 Concentrator (Amicon, MWCO 3000, previously cleaned by 2 mL of Milli Q water centrifuged at 3750 rpm for 90 min.) and centrifuged at. 3750 rpm for 60 min. The resulting filtrates were then assayed as shown in Table 21 and Table 22.

TABLE 21

Assay of filtrates for S156C-S-EtMan (Enzyme Concentrations 2.58 mg/mL)

| Vial No. | HABA/ Avidin Before[a]/ Abs | HABA/ Avidin After[b]/ Abs | HABA/ Avidin Diff./ Abs | Incub. Time/ min | $A_{280}$[c] | Biotin Release/ Abs[d] | Total Protein/ Abs | % of Max Biotin/ Abs | % of Max Total Protein/ Abs |
|---|---|---|---|---|---|---|---|---|---|
| 1 | 1.006 | 0.726 | 0.28 | 60 | 0.003 | — | — | — | — |
| 2 | 1.004 | 0.719 | 0.285 | 60 | 0.003 | — | — | — | — |
| 3 | 1.012 | 0.665 | 0.347 | 60 | 0.033 | 0.062 | 0.03 | 45 | 54 |
| 4 | 1.009 | 0.597 | 0.412 | 210 | 0.042 | 0.127 | 0.039 | 93 | 70 |
| 5 | 1.01 | 0.662 | 0.348 | 60 | 0.022 | 0.063 | 0.019 | 46 | 34 |
| 6 | 1 | 0.6 | 0.4 | 210 | 0.046 | 0.115 | 0.043 | 84 | 77 |
| 7 | 1.014 | 0.649 | 0.365 | 60 | 0.028 | 0.08 | 0.025 | 58 | 45 |
| 8 | 0.998 | 0.576 | 0.422 | 210 | 0.049 | 0.137 | 0.046 | 100 | 82 |
| 9 | 1.012 | 0.659 | 0.353 | 60 | 0.035 | 0.068 | 0.032 | 50 | 57 |
| 10 | 1.007 | 0.591 | 0.416 | 210 | 0.059 | 0.131 | 0.056 | 96 | 100 |

[a]800 µL of HABA/Avidin Reagent (Sigma) prepared with 1 mL of Milli Q water.
[b]After addition of 200 µL of lectin-assay filtrate.
[c]Value for 300 µL of lectin-assay filtrate diluted with 700 µL of Milli Q as compared with Milli Q water blank (1 mL).
[d]Calculated from difference between HABA/Avidin drop in Abs. for sample and the drop in Abs. caused by dilution alone (controls).

TABLE 22

Assay of filtrates for S156C-S-EtMan(Ac)$_4$ (Enzyme Concentration 2.40 mg/mL)

| Vial No. | HABA/ Avidin Before[a]/ Abs | HABA/ Avidin After[b]/ Abs | HABA/ Avidin Diff./ Abs | Incub. Time/ min | $A_{280}$[c] | Biotin Release/ Abs[d] | Total Protein/ Abs | % of Max Biotin/ Abs | % of Max Total Protein/ Abs |
|---|---|---|---|---|---|---|---|---|---|
| 1 | 0.983 | 0.717 | 0.266 | 60 | 0.002 | — | — | — | — |
| 2 | 0.982 | 0.711 | 0.271 | 60 | 0.009 | — | — | — | — |
| 3 | 0.98 | 0.633 | 0.347 | 60 | 0.027 | 0.079 | 0.021 | 35 | 31 |
| 4 | 1.002 | 0.559 | 0.443 | 210 | 0.06 | 0.175 | 0.054 | 78 | 79 |
| 5 | 0.991 | 0.628 | 0.363 | 60 | 0.034 | 0.095 | 0.028 | 42 | 41 |
| 6 | 1.004 | 0.548 | 0.456 | 210 | 0.063 | 0.188 | 0.057 | 84 | 84 |
| 7 | 0.998 | 0.606 | 0.392 | 60 | 0.041 | 0.124 | 0.035 | 55 | 51 |
| 8 | 1.003 | 0.511 | 0.492 | 210 | 0.069 | 0.224 | 0.063 | 100 | 93 |
| 9 | 1.001 | 0.651 | 0.35 | 60 | 0.038 | 0.082 | 0.032 | 37 | 47 |
| 10 | 1.013 | 0.54 | 0.473 | 210 | 0.074 | 0.205 | 0.068 | 92 | 100 |

[a,b,c,d]as above.

Example 7

Lectin Degradation Assay using Other glycosylated-CMMs and of Mannosylated-SBL with higher Decoy Protein Concentrations In addition to S156C-S-EtMan and S156C-S-EtMan(Ac)$_4$ reported earlier the lectin assay was performed for other glycosylated CMMs. Furthermore the selectivity of S156C-S-EtMan at higher levels of decoy protein was investigated. The data showed that as for S-EtManAc the other sugars glucose, galactose and lactose showed little or no selectivity. By challenging S156C-S-EtMan with 5-fold higher levels of decoy protein the selectivity of this mannosylated CMM was decreased to approximately a difference of about 12% in total protein levels with and without decoy.

Experimental

Lectin Assay Method 1.

Ten disposable eppendorf vials were filled as shown in Table 23:

TABLE 23

| | Lectin assay method 1. | | | |
|---|---|---|---|---|
| Vial No. | Lectin-Assay Buffer[a]/µL | Concanavalin A[b]/µL | Decoy Protein[c]/µL | Enzyme/ µL |
| 1 | 900 | 100 | — | — |
| 2 | 890 | 100 | 10 | — |
| 3 | 900 | 100 | — | 10 of glyco-CMM |
| 4 | 900 | 100 | — | 10 of glyco-CMM |
| 5 | 890 | 100 | 10 | 10 of glyco-CMM |
| 6 | 890 | 100 | 10 | 10 of glyco-CMM |
| 7 | 900 | 100 | — | 10 of WT[d] |
| 8 | 900 | 100 | — | 10 of WT[d] |
| 9 | 890 | 100 | 10 | 10 of WT[d] |
| 10 | 890 | 100 | 10 | 10 of WT[d] |

[a]Lectin-Assay Buffer: 20 mM Tris•HCl, 2 mM CaCl$_2$, pH 8.6.
[b]5 mg/mL solution of Biotinylated Concanavalin A (Vector Laboratories) in Milli Q water.
[c]5 mg/mL solution of Ribonuclease A with Scrambled Disulfide Bonds (Sigma) in Milli Q water.
[d]Solution of lyophilized GG36-WT diluted to the same concentration as the glyco-CMM (as determined by PMSF) in 20 mM MES, 1 mM CaCl$_2$, pH 5.5.

These solutions were warmed to 35° C. in a thermostat-controlled water bath. After the indicated incubation time, the contents of the appropriate vials were each placed in the top of a Centricon-SR3 Concentrator (Amicon, MWCO 3000, previously cleaned by 2 mL of Milli Q water centrifuged at 3750 rpm for 90 min.) and centrifuged at 3750 rpm for 60 min. The resulting filtrates were then assayed as shown in Table 24, Table 25, and Table 26.

TABLE 24

Assay of filtrate (S156C-S-EtβGlc (Enzyme Concentration 2.29 mg/mL))

| Vial No. | HABA/ Avidin Before[a]/ Abs | HABA/ Avidin After[b]/ Abs | HABA/ Avidin Diff./ Abs | Incub. Time/ min | $A_{280}$[c] | Biotin Release/ Abs[d] | Total Protein/ Abs | % of Max Biotin/ Abs | % of Max Total Protein/ Abs |
|---|---|---|---|---|---|---|---|---|---|
| 1 | 0.989 | 0.779 | 0.21 | 60 | 0.003 | — | — | — | — |
| 2 | 1.011 | 0.789 | 0.222 | 60 | 0.009 | — | — | — | — |
| 3 | 0.992 | 0.637 | 0.355 | 60 | 0.025 | 0.14 | 0.019 | 53 | 29 |
| 4 | 1.024 | 0.545 | 0.479 | 210 | 0.068 | 0.264 | 0.062 | 100 | 95 |
| 5 | 1.011 | 0.63 | 0.381 | 60 | 0.038 | 0.166 | 0.032 | 63 | 49 |
| 6 | 0.995 | 0.566 | 0.429 | 210 | 0.068 | 0.214 | 0.062 | 81 | 95 |
| 7 | 0.999 | 0.604 | 0.395 | 60 | 0.036 | 0.18 | 0.03 | 68 | 46 |
| 8 | 1.003 | 0.554 | 0.449 | 210 | 0.062 | 0.234 | 0.056 | 89 | 86 |
| 9 | 1.037 | 0.648 | 0.389 | 60 | 0.042 | 0.174 | 0.036 | 66 | 55 |
| 10 | 0.996 | 0.568 | 0.428 | 210 | 0.071 | 0.213 | 0.065 | 81 | 100 |

[a]800 μL of HABA/Avidin Reagent (Sigma) prepared with 1 mL of Milli Q water.
[b]After addition of 200 μL of lectin-assay filtrate.
[c]Value for 300 μL of lectin-assay filtrate diluted with 700 μL of Milli Q as compared with Milli Q water blank (1 mL).
[d]Calculated from difference between HABA/Avidin drop in Abs. for sample and the drop in Abs. caused by dilution alone (controls).

TABLE 25

Assay of filtrate (S156C-S-EtGal (Enzyme Concentration 1.73 mg/mL))

| Vial No. | HABA/ Avidin Before[a]/ Abs | HABA/ Avidin After[b]/ Abs | HABA/ Avidin Diff./ Abs | Incub. Time/ min | $A_{280}$[c] | Biotin Release/ Abs[d] | Total Protein/ Abs | % of Max Biotin/ Abs | % of Max Total Protein/ Abs |
|---|---|---|---|---|---|---|---|---|---|
| 1 | 0.995 | 0.77 | 0.225 | 60 | −0.004 | — | — | — | — |
| 2 | 1.002 | 0.768 | 0.234 | 60 | −0.007 | — | — | — | — |
| 3 | 1.011 | 0.629 | 0.382 | 60 | 0.02 | 0.152 | 0.026 | 67 | 37 |
| 4 | 0.975 | 0.531 | 0.444 | 210 | 0.055 | 0.214 | 0.061 | 94 | 87 |
| 5 | 1.005 | 0.621 | 0.384 | 60 | 0.028 | 0.154 | 0.034 | 68 | 49 |
| 6 | 0.978 | 0.543 | 0.435 | 210 | 0.063 | 0.205 | 0.069 | 90 | 99 |
| 7 | 1.018 | 0.652 | 0.366 | 60 | 0.01 | 0.136 | 0.016 | 60 | 23 |
| 8 | 1.01 | 0.553 | 0.457 | 210 | 0.048 | 0.227 | 0.054 | 100 | 77 |
| 9 | 1.011 | 0.666 | 0.345 | 60 | 0.014 | 0.115 | 0.02 | 51 | 29 |
| 10 | 0.997 | 0.563 | 0.434 | 210 | 0.064 | 0.204 | 0.07 | 90 | 100 |

[a,b,c,d]as above.

TABLE 26

Assay of filtrate S156C-S-EtLac (Enzyme Concentration 2.25 mg/mL).

| Vial No. | HABA/ Avidin Before[a]/ Abs | HABA/ Avidin After[b]/ Abs | HABA/ Avidin Diff./ Abs | Incub. Time/ min | $A_{280}$[c] | Biotin Release/ Abs[d] | Total Protein/ Abs | % of Max Biotin/ Abs | % of Max Total Protein/ Abs |
|---|---|---|---|---|---|---|---|---|---|
| 1 | 1.006 | 0.77 | 0.236 | 60 | −0.006 | — | — | — | — |
| 2 | 0.994 | 0.762 | 0.232 | 60 | −0.002 | — | — | — | — |
| 3 | 0.993 | 0.684 | 0.309 | 60 | 0.008 | 0.075 | 0.012 | 35 | 15 |
| 4 | 1.023 | 0.584 | 0.439 | 210 | 0.04 | 0.205 | 0.044 | 95 | 56 |
| 5 | 0.994 | 0.676 | 0.318 | 60 | 0.013 | 0.084 | 0.017 | 39 | 22 |
| 6 | 1 | 0.578 | 0.422 | 210 | 0.068 | 0.188 | 0.072 | 87 | 91 |
| 7 | 1.014 | 0.655 | 0.359 | 60 | 0.012 | 0.125 | 0.016 | 58 | 20 |
| 8 | 1.012 | 0.562 | 0.45 | 210 | 0.047 | 0.216 | 0.051 | 100 | 65 |
| 9 | 1.001 | 0.674 | 0.327 | 60 | 0.014 | 0.093 | 0.018 | 43 | 23 |
| 10 | 1.006 | 0.57 | 0.436 | 210 | 0.075 | 0.202 | 0.079 | 94 | 100 |

[a,b,c,d]as above.

Control without Lectin.

The assay was performed as for method 1 except 100 μL aliquots of concanavalin replaced by 100 μL of Milli Q water. Results are shown in Table 27.

TABLE 27

Assay of filtrate. Control without lectin.

| Vial No. | HABA/ Avidin Before[a]/ Abs | HABA/ Avidin After[b]/ Abs | HABA/ Avidin Diff./ Abs | Incub. Time/ min | $A_{280}{}^{c}$ | Biotin Release/ Abs[d] | Total Protein/ Abs | % of Max Biotin/ Abs | % of Max Total Protein/ Abs |
|---|---|---|---|---|---|---|---|---|---|
| 1 | 1.004 | 0.768 | 0.236 | 60 | −0.005 | — | — | — | — |
| 2 | 1 | 0.77 | 0.23 | 60 | −0.008 | — | — | — | — |
| 3 | 0.998 | 0.768 | 0.23 | 60 | −0.008 | −0.003 | −0.001 | −1 | −1 |
| 4 | 1 | 0.774 | 0.226 | 210 | −0.007 | −0.007 | 0 | −3 | 0 |
| 5 | 1.023 | 0.78 | 0.243 | 60 | 0.004 | 0.01 | 0.011 | 5 | 14 |
| 6 | 1.02 | 0.783 | 0.237 | 210 | 0.007 | 0.004 | 0.014 | 2 | 18 |
| 7 | 1.018 | 0.774 | 0.244 | 60 | −0.005 | 0.011 | 0.002 | 5 | 3 |
| 8 | 1.001 | 0.774 | 0.227 | 210 | −0.002 | −0.006 | 0.005 | −3 | 6 |
| 9 | 1.006 | 0.769 | 0.237 | 60 | 0.008 | 0.004 | 0.015 | 2 | 19 |
| 10 | 1.004 | 0.771 | 0.233 | 210 | 0.012 | −2.8E−17 | 0.019 | 0 | 24 |

[a,b,c,d]as above.

Lectin Assay Method 2.

Ten disposable eppendorf vials were filled as shown in Table 28.

TABLE 28

Design of lectin assay 2.

| Vial No. | Lectin-Assay Buffer[a]/μL | Concanavalin A[b]/μL | Decoy Protein[c]/μL | Enzyme/ μL |
|---|---|---|---|---|
| 1 | 900 | 100 | — | — |
| 2 | 850 | 100 | 50 | — |
| 3 | 900 | 100 | — | 10 of glyco-CMM |
| 4 | 900 | 100 | — | 10 of glyco-CMM |
| 5 | 850 | 100 | 50 | 10 of glyco-CMM |
| 6 | 850 | 100 | 50 | 10 of glyco-CMM |
| 7 | 900 | 100 | — | 10 of WT[d] |
| 8 | 900 | 100 | — | 10 of WT[d] |
| 9 | 850 | 100 | 50 | 10 of WT[d] |
| 10 | 850 | 100 | 50 | 10 of WT[d] |

[a]Lectin-Assay Buffer: 20 mM Tris•HCl, 2 mM CaCl$_2$, pH 8.6.
[b]5 mg/mL solution of Biotinylated Concanavalin A (Vector Laboratories) in Milli Q water.
[c]5 mg/mL solution of Ribonuclease A with Scrambled Disulfide Bonds (Sigma) in Milli Q water.
[d]Solution of lyophilized GG36-WT diluted to the same concentration as the glyco-CMM (as determined by PMSF) in 20 mM MES, 1 mM CaCl$_2$, pH 5.5.

All further determinations were carried out as for Method 1 and the results are shown in Table 29.

TABLE 29

Assay of filtrate S156C-S-EtMan (Enzyme Concentrations 2.58 mg/mL)

| Vial No. | HABA/ Avidin Before[a]/ Abs | HABA/ Avidin After[b]/ Abs | HABA/ Avidin Diff./ Abs | Incub. Time/ min | $A_{280}{}^{c}$ | Biotin Release/ Abs[d] | Total Protein/ Abs | % of Max Biotin/ Abs | % of Max Total Protein/ Abs |
|---|---|---|---|---|---|---|---|---|---|
| 1 | 0.969 | 0.76 | 0.209 | 60 | −0.003 | — | — | — | — |
| 2 | 0.982 | 0.756 | 0.226 | 60 | 0.005 | — | — | — | — |
| 3 | 0.975 | 0.649 | 0.326 | 60 | 0.018 | 0.108 | 0.017 | 52 | 21 |
| 4 | 0.97 | 0.562 | 0.408 | 210 | 0.048 | 0.19 | 0.047 | 92 | 57 |
| 5 | 0.99 | 0.685 | 0.305 | 60 | 0.03 | 0.087 | 0.029 | 42 | 35 |
| 6 | 0.988 | 0.589 | 0.399 | 210 | 0.068 | 0.181 | 0.067 | 87 | 82 |
| 7 | 0.983 | 0.637 | 0.346 | 60 | 0.028 | 0.128 | 0.027 | 62 | 33 |
| 8 | 0.974 | 0.549 | 0.425 | 210 | 0.053 | 0.207 | 0.052 | 100 | 63 |
| 9 | 0.978 | 0.659 | 0.319 | 60 | 0.037 | 0.101 | 0.036 | 49 | 44 |
| 10 | 0.982 | 0.599 | 0.383 | 210 | 0.083 | 0.165 | 0.082 | 80 | 100 |

[a,b,c,d]as for Method 1.

Example 8

Synthesis of Biotin-MTS

In order to exploit the powerful binding of biotin to avidin as a model system to clearly demonstrate the targeting strategy the biotin-MTS reagent 1 was synthesized.

Figure 16:
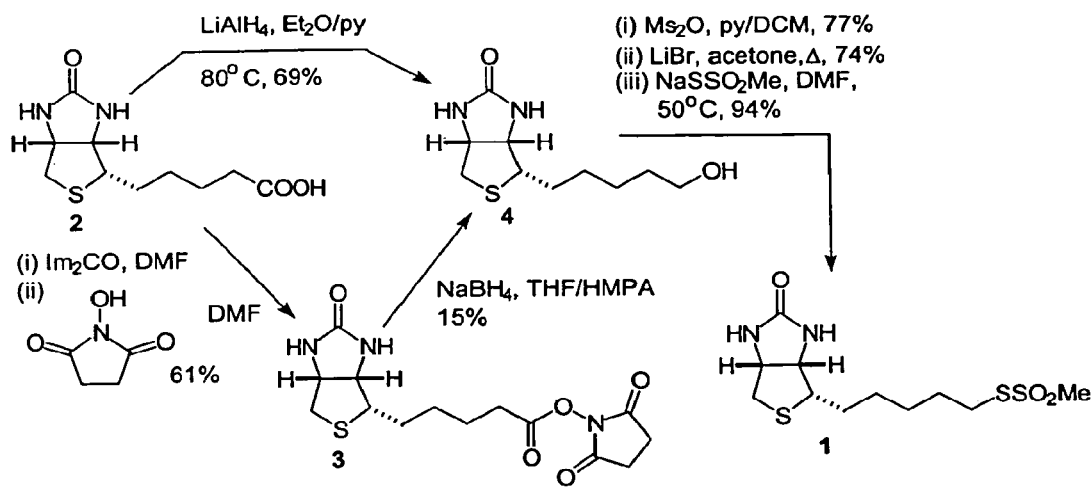
FIG. 16 illustrates synthesis scheme 7 for the synthesis of biotin-MTS reagent 1.

In the synthetic strategy chosen (FIG. 16, scheme 7) we chose the carboxylic acid group of biotin as the point at which to introduce methanethiosulfonate as previous studies have shown that functionalization of this part of the molecule preserves affinity for avidin (Green (1975) *Adv. Protein Chem.* 29: 85-133; Green (1990) *Meth. Enzymol.* 184: 51-67).

Initial attempts to reduce the N-hydroxysuccinamide ester 3 using $NaBH_4$ (Islam et al. (1994) *J. Med. Chem.*, 37: 293-304.), synthesized from (+)-biotin (2) in 61% yield according to literature methods (Chaturvedi et al. (1984) *J. Med. Chem.*, 27: 1406-1410), gave only a poor 15% yield of (+)-biotinol (4). In contrast, direct reduction of (+)-biotin (2) with $LiAlH_4$ gave 4 in a reasonable 69% yield (Flaster and Kohn (1981) *Heterocycl. Chem.* 18: 1425-1436). The use of ether as a solvent is crucial to the success of this reduction as THF gave only a very low yield of (+)-biotinol (4).

Biotinol (4) was elaborated, according to our established preparative procedure, to the target biotin-MTS via the corresponding primary mesylate and bromide. The use of MsCl led to only a moderate yield of mesylate as a result of competing formation of primary chloride. Consequently, biotinol (4) was treated with mesylic anhydride in pyridine/DCM, then LiBr in refluxing acetone and finally $NaSSO_2Me$ in DMF to give target biotin-MTS 1 in 54% yield over 3 steps (37% overall yield from (+)-biotin (2)). Attempts to scale up this synthesis gave reduced yields.

Experimental

(+)-Biotinol (4) via Hydroxysuccinamide Ester (3)

1,1'-Dicarbonylimidazole (360 mg, 2.22 mmol) was added to a stirred solution of (+)-biotin (2) (540 mg, 2.2 mmol) in DMF (10 mL) under $N_2$ and the resulting solution heated until evolution of $CO_2$ ceased (approx 30 min.). The solution was cooled to RT and stirred for a further 2 h, during which time a white solid precipitated from solution. A solution of N-hydroxysuccinimide (260 mg, 2.26 mmol) in DMF (10 mL) was added and the mixture stirred. After a further 6 h, the reaction solvent was removed and the residue recrystallized first from propan-2-ol (mp 187-187° C.) and then DMF/propan-2-ol to give 3 (457 mg, 61%) as a white solid; mp 197-201° C. (DMF/propan2-ol) [lit., Becker et al. (1971) *Proc. Natl. Acad. Sci., USA*, 68: 2604-2607, mp 196-200° C.; lit., Parameswaran (1990) *Org. Prep. Proc. Intl.* 22: 119-121, mp 210° C.]; $^1H$ NMR ($d^6$-DMSO, 200 MHz) 1.43-1.70 (m, 4H), 2.52-2.90 (m, 9H), 3.07-3.14 (m, 4H, H-4), 4.17 (dd, J=6 Hz, J=4 Hz, 1H, H-3a), 4.32 (dd, J=6 Hz, J=7 Hz, 1H, H-6a), 6.39, 6.45 (s__2, 1H__2, H-1, H-3).

$NaBH_4$ (50 mg, 1.32 mmol) was added to a suspension of 3 (170 mg, 0.5 mmol) stirred in THF/HMPA (40:1, 41 mL) under nitrogen. After 4.5 h the volume of reaction solvent was reduced and the resulting residue quenched with water. The residue was dried further under vacuum and purified by flash chromatography ($MeOH:CHCl_3$, 1:19) to give 4 (17 mg, 15%) as a white solid.

5-([3aS-(3aα,4β,6aα)]-Hexahydro-2-oxo-1H-thieno[3,4-d]imidazol-4-yl)pentyl methanethiosulfonate [(+)-Biotin MTS] (1)

(+)-Biotin (2) (196 mg, 0.8 mmol) was dissolved in pyridine (5 mL) by careful warming at 80° C. under nitrogen. The resulting solution was added dropwise to a suspension of $LiAlH_4$ (196 mg, 5.15 mmol) in freshly distilled dry ether (25 mL) under nitrogen. After 30 min. the resulting mixture was heated to reflux. After a further 40 min., tlc ($MeOH:CHCl_3$, 1:9) showed the formation of a major product ($R_f$ 0.35) from starting material ($R_f$ 0.45). The reaction was cooled and remaining $LiAlH_4$ quenched by the dropwise addition of water. After effervescence had ceased more water (100 mL) was added and the solvent removed. The residue was dried overnight under vacuum and then purified by flash chromatography ($MeOH:CHCl_3$, 1:19) to give (+)-biotinol[3aS-(3aα, 4β, 6aα)]-Tetrahydro-4-(5-hydroxypentyl)-1H-thieno[3,4-d]imidazol-2(3H)-one (4) (128 mg, 69%) [53906-36-8] as a white solid; mp 168-172 [lit., U.S. Pat. No. 2,489,237, mp 174.5-175.5 (MeOH)]; $[\alpha]^{28}_D=+91.2$ (c 0.43, MeOH) [lit., $[\alpha]^{25}_D=+84.7$ (c 1, MeOH)]; $^1H$ NMR ($CD_3OD$, 400 MHz) δ 1.42-1.48 (m, 4H), 1.52-1.63 (m, 3H), 1.72-1.75 (m, 1H), 2.71 (d, $J_{6,6'}$ 12.6 Hz, 1H, H-6), 2.93 (dd, $J_{6',6}$a 4.9 Hz, $J_{6,6'}$ 12.8 Hz, 1H, H-6'), 3.22 (qu, J=4.8 Hz, 1H, H-4), 3.56 (t, J=6.5 Hz, 2H, $CH_2OH$), 4.31 (dd, $J_{3a,4}$ 4.4 Hz, $J_{3a,6a}$ 7.8 Hz, 1H, H-3a), 4.51 (dd, $J_{6',6}$a 4.9 Hz, $J_{3a,6a}$ 7.9 Hz, 1H, H-6a).

$Ms_2O$ (78 mg, 0.45 mmol) was added to a solution of 4 (80 mg, 0.35 mmol) in pyridine/DCM (1:1, 4 mL) under nitrogen. After 14 h the solvent was removed. The residue was dissolved in $CHCl_3$ (30 mL), washed (water (10 mL), brine (10 mL)), dried ($MgSO_4$), filtered and the solvent removed. The residue was purified by flash chromatography ($MeOH:CHCl_3$, 1:50) to give the mesylate [3aS-(3aα,4β,6aα)]-Tetrahydro-4-[5-(methanesulfonyl)pentyl]-1H-thieno[3,4-d]imidazol-2(3H)-one (83 mg, 77%) as a yellow oil; a scale up provides the mesylate as a pale yellow solid; mp 134-136; IR (film) 3432 (NH), 1702 (amide I), 1636 (amide II) $cm^{-1}$; $^1H$ NMR ($CDCl_3$, 400 MHz) δ 1.45-1.47 (m, 4H), 1.67-1.79 (m, 4H), 2.75 (d, $J_{6,6'}$ 12.8 Hz, 1H, H-6), 2.92 (br d, J=9.4 Hz, 1H, H-6'), 3.02 (s, 3H, $CH_3SO_2$—), 3.15-3.19 (m, 1H, H-4), 4.24 (t, J=6.4 Hz, 2H, $CH_2OMs$), 4.32 (dd, $J_{3a,4}$ 4.8 Hz, $J_{3a,6a}$ 7.3 Hz, 1H, H-3a), 4.51 (m, 1H, H-6a); $^{13}C$ NMR ($CDCl_3$, 50 MHz) δ 25.4, 28.3, 28.5, 28.8, 37.4, 40.5, 55.5 (($CH_2$)$_4$, C-4, C-6, $CH_3SO_2$—), 60.3, 62.1 (C-3a, C-6a), 70.1 ($CH_2OMs$), 163.6 (C-2).

LiBr (80 mg, 0.92 mmol) was added to a solution of mesylate (40 mg, 0.13 mmol) in acetone (2 mL) under nitrogen and the resulting solution heated under reflux. After 14 h, tlc ($MeOH:CHCl_3$, 1:9) showed the conversion of starting material ($R_f$ 03) to product ($R_f$ 0.45). The solvent was removed and the residue partitioned between ether (30 mL) and water (10 mL). The aqueous fraction was further extracted with $CHCl_3$ (30 mL__2) in which the bromide is more soluble. The organic fractions were combined, dried ($MgSO_4$), filtered and the solvent removed to give the crude bromide [3aS-(3aα,4β, 6aα)]-Tetrahydro-4-(5-bromopentyl)-1H-thieno[3,4-d]imidazol-2(3H)-one (28 mg, 74%) as a yellow oil, which was used directly in the next step. A scale up provides the product as a pale yellow solid; mp 157-159.

$NaSSO_2Me$ (15 mg, 0.11 mmol) was added to a solution of crude bromide (24 mg, 0.08 mmol) in DMF (2 mL) and the resulting solution heated under nitrogen at 50° C. After 19 h, tlc ($MeOH:CHCl_3$, 1:9) showed the formation of a major product ($R_f$ 0.35) from starting material ($R_f$ 0.45). The solvent was removed and the residue purified by repeated flash chromatography ($MeOH:CHCl_3$ 1:19 then 3:97) to give 1 (25 mg, 94%, 37% from (+)-biotin (2)) as an amorphous solid; a scale up provides 1 as a pale yellow solid; $[\alpha]_D^{26}$+42.1 (c, 0.62 in $CHCl_3$); IR (film) 3215 (NH), 1699 (C=O), 1310, 1129 (S—$SO_2$) $cm^{-1}$; $^1H$ NMR ($CDCl_3$, 400 MHz) δ 1.45-1.47 (m, 4H), 1.62-1.70 (m, 2H), 1.72-1.80 (m, 2H), 2.75 (d, $J_{6,6'}$ 13.0 Hz, 1H, H-6), 2.93 (br d, J=9.3 Hz, 1H, H-6'), 3.13-3.19 (m, 3H, H-4, —CH$_2$S—), 3.34 (s, 3H, CH$_3$SO$_2$—), 4.33 (dd, J$_{3a,4}$ 4.2 Hz, J$_{3a,6a}$ 7.1 Hz, 1H, H-3a), 4.53 (dd, J$_{6',6}$a 4.9 Hz, J$_{3a,6a}$ 6.8 Hz, 1H, H-6a); $^{13}$C NMR (CDCl$_3$, 100 MHz) δ 28.4, 28.5, 28.6, 29.4, 36.4, 40.6, 55.6 ((CH$_2$)$_4$, C-4, C-6, —CH$_2$S—), 50.9 (CH$_3$SO$_2$—), 60.6, 62.4 (C-3a, C-6a), 163.5 (C-2); HRMS m/z (FAB+). Found 325.0755 (M+H$^4$); C$_{11}$H$_{20}$N$_2$O$_3$S$_3$ requires 325.0714.

Example 9

Preparation and Characterization of Biotin-CMMs

Preparation of the Biotin-CMMs

Biotin-MTS reagent 1 was used to prepare the biotinylated CMMs of N62C, L217C, S166C, and S156C mutants, by reaction at pH 9.5 following the standard protocol. In all cases the resulting enzymes are active after modification.

Amidase Kinetics of the Biotin-CMMs

The data for amidase kinetics and ESMS are shown in Table 30.

TABLE 30

Kinetic Constants for Biotin-CMMs.

| (+)-Biotin- CMM | Amidase Kinetics | | | ESMS | |
|---|---|---|---|---|---|
| | k$_{cat}$ | K$_M$ | k$_{cat}$/K$_M$ | Calc. | Found |
| S166C | 56.3 | 1.4 | 1.00 | 0.05 | 56.1 | 3.3 | 26958 | 26967 |
| S156C | 75.4 | 2.2 | 0.83 | 0.06 | 91.1 | 7.2 | 26958 | 26968 |
| N62C | 122 | 1.8 | 1.06 | 0.04 | 115 | 4.4 | 26931 | 26936 |
| L217C | 60.3 | 0.8 | 0.72 | 0.02 | 83.4 | 3.1 | 26932 | 26936 |
| GG36-WT | 153 | 4 | 0.73 | 0.05 | 209 | 15 | 26698 | 26694 |

Kinetic constants determined in duplicate by method of initial rates in 0.1M TRIS buffer, pH 8.6, 0.005% Tween 80, 1% DMSO. [S] = 0.125 mM to 3 mM, [E] = 1.4 10$^{-8}$ M to 2.4 10$^{-8}$ M.

All biotin-CMMs had a smaller catalytic activity than SBL-WT (k$_{cat}$/K$_M$=209 15).

The values for the S156C-S-Biotin CMM and the L217C-S-Biotin CMM were similar and showed a decreased k$_{cat}$ compared to SBL-WT, whereas the change in K$_M$ is negligible.

Modification of the S166C mutant with the biotin-MTS reagent gave, compared to SBL-WT, a four times lower k$_{cat}$/K$_M$. The S166C-S-Biotin CMM also had the lowest k$_{cat}$/K$_M$ of all the biotinylated CMMs. Both k$_{cat}$ and K$_M$ are altered for this CMM.

The N62C-S-Biotin CMM had a slightly decreased k$_{cat}$ compared to SBL-WT and has the highest K$_M$ of all the biotin-CMMs, however it was still the most active of these biotinylated CMMs.

Esterase Kinetics of the Biotin-CMMs

Esterase kinetics was carried out for the biotin-CMMs according to the standard protocol with suc-AAPF-SBn as substrate. The results are shown in Table 31.

TABLE 31

Esterase Kinetics for Biotin-CMMs

| (+)-Biotin- CMM | Esterase Kinetics | | |
|---|---|---|---|
| | K$_{cat}$ | K$_M$ | k$_{cat}$/K$_M$ |
| S166C | 489 | 41.0 | 0.59 | 0.14 | 830 | 212 |
| S156C | 825 | 42.7 | 0.68 | 0.10 | 1221 | 187 |
| N62C | 422 | 27.3 | 0.21 | 0.05 | 1973 | 497 |
| L217C | 432 | 52.5 | 0.35 | 0.15 | 1229 | 559 |
| GG36-WT | 1940 | 180 | 0.54 | 0.07 | 3560 | 540 |

Kinetic constants determined in duplicate by method of initial rates in 0.1M TRIS buffer, pH 8.6, 0.005% Tween 80, 1% DMSO. [S] = 0.015 mM to 3 mM, [E] = 0.8 × 10$^{-9}$ M to 1.2 × 10$^{-9}$ M.

The k$_{cat}$/K$_M$ results for esterase activity follow the same trend compared to amidase kinetics.

The S166C-S-Biotin CMM shows the smallest k$_{cat}$/K$_M$, which is about four times lower than for SBL-WT.

The biotin-CMMs have an approximately four fold lower k$_{cat}$ compared to SBL-WT with the S156C-S-Biotin CMM as the only exception. The k$_{cat}$ of the S156C-S-Biotin CMM is about two fold lower than for SBL-WT and therefore two fold higher compared to the other biotin-CMMs. However, S156C-S-Biotin CMM is not the most active of all biotinylated CMMs since it has also the highest K$_M$ value. The k$_{cat}$/K$_M$ of S156C-S-Biotin CMM and L217C-S-Biotin CMM are very similar, about 3-fold lower than for SBL-WT, although k$_{cat}$ and K$_M$ show big differences.

The K$_M$ values of the biotin-CMMs were slightly higher for the S166C-S-Biotin CMM and the S156C-S-Biotin CMM compared to SBL-WT. Whereas, the values for the N62C-S-Biotin CMM and the L217C-S-Biotin CMM are about two times smaller compared to SBL-WT.

The N62C-S-Biotin CMM has the lowest K$_M$ of all the biotinylated CMMs, and is 2.6 fold lower than SBL-WT. Although it also has the lowest k$_{cat}$ of the biotin-CMMs, it has the highest catalytic activity, which is still 1.8 fold lower then SBL-WT.

Example 10

Targeting a Binding Protein

Targeting and Hydrolysis of Avidin with Biotin-CMMs

It is known from the literature that biotinylated proteins will bind to avidin only when the biotin is separated from the surface of the macromolecule to which it is covalently linked by at least five methylene groups (Green (1970) *Meth. Enzymol.* 18A: 418-424). Furthermore, Wilchek et al. observed that proteolytic enzymes are not able to cleave avidin. Even when the proteases is biotinylated, avidin is not cleaved (Bayer et al. (1990) *Biochemistry*, 29: 11274-11279).

Our goal in this project is not only to establish targeting of our new biotin-CMMs to avidin but also to demonstrate that the CMMs are capable of catalyzing avidin proteolysis. SBL-WT, which it is not able to complex avidin but may hydrolyze avidin in an unselective process, is used for comparison.

The colorimetric method previously used to demonstrate lectin degradation with glycosylated CMMs was adapted, to assay the ability of the synthesized biotin-CMMs to target avidin. We measured the release of HABA from HABA/avidin reagent which was detected by an increase of absorbance at 500 nm. All biotinylated CMMs were examined and the amount of CMM used was corrected for equal catalytic activity compared to each other based on k$_{cat}$/K$_M$ with suc-AAPF-pNA. Therefore, differences between the capability of our biotin-CMMs to target to avidin can be discussed.

In order to investigate the ability of our biotin-CMMs not only to target avidin but also to hydrolyze, we decided to separate the assay for targeting and the assay for hydrolysis of avidin with our biotinylated CMMs.

As already mentioned, targeting can be clearly proven by measuring HABA release from a HABA/avidin solution at 500 nm. Since we were now only interested in using this method as a targeting assay for avidin we measured the HABA release over a 5 min period. Despite the fact that only for S156C-S-Biotin the introduced biotin-side-chain is surface exposed and therefore easily accessible for binding to avidin, surprisingly all biotin-CMMs caused immediate HABA release when added to a buffered solution of HABA/avidin. Due to its surface exposure S156C-S-Biotin resulted in the highest HABA release compared to the other CMMs.

We controlled the targeting process by comparison with solutions of SBL-WT (concentration calculated for same catalytic activity) and addition of (+)-biotin [diluted to the same concentration as expected in each one of the biotin-CMMs (by determination of PMSF-value).

Since, for steric reasons, (+)-biotin should be better available to bind to avidin than the biotinylated side-chain of our CMMs we expected a smaller or, for the best case, the same HABA release for all biotin-CMMs compared to the biotin/WT mixture.

S166C-, N62C- and L217C-S-Biotin confirmed our predictions, the S156C CMM however gave a drastically higher HABA release.

We determined therefore the whole protein amount of the S156C-S-Biotin solution by lyophilization and calculated the biotin amount again (B2a). In this case the HABA release for a biotin/NWT mixture is higher than for the S156C CMM, and we suggest that there might be inactive enzyme bearing the biotin group in the CMM solution which also binds avidin and causes therefore additional HABA release.

For determination of avidin hydrolysis catalyzed by SBL-WT and the biotin-CMMs, respectively, we adopted the lectin assay method and measured $A_{280}$ for hydrolysis fragments <3000 Da. The assay was carried out for S156C-S-Biotin since this CMM proved to be the best enzyme in the targeting assay. To allow comparison and demonstrate unselective hydrolysis, the SBL-WT was used as a solution diluted to the same catalytic activity as the biotin-CMM solution.

The initial measurements with HABA/avidin and the enzyme revealed anomalies presumably caused by HABA, therefore we decided to do this assay with avidin alone. To determine the selectivity of avidin hydrolysis, a decoy protein, disulfide scrambled-RNAse A, was used, similar to the lectin assay described above. The solutions were incubated for 1 h and 4 h, respectively, and small protein fragments (<3000 Da), the products of hydrolysis, were separated using a size-exclusion membrane. Measurement of $A_{280}$ furnished the total protein fragment concentration and is therefore an indicator of avidin hydrolysis.

Both SBL-WT and S156C-S-Biotin are able to hydrolyze avidin. Since the enzyme concentrations were calculated for equal catalytic activity with the standard amidase substrate suc-AAPF-pNA the hydrolysis values can be compared directly. Therefore we are able to demonstrate not only that avidin is hydrolyzed by SBL-proteases but is also more efficiently hydrolyzed by a biotinylated protease. S156C-S-Biotin produces 45% more protein fragments after 240 min than GG36-WT. In the presence of decoy protein [0.05 mg, Decoy (1)] the amount of total protein produced increased drastically for the WT enzyme (27% after 240 min) whereas the production of total protein did not change significantly for the biotin-CMM. However a 3-fold higher level of decoy protein [0.15 mg, Decoy (2)] resulted also for S156C-S-Biotin in increasing production of total protein (38% after 240 min) which indicates a decreased selectivity for avidin. In studies run with controls for GG36-WT with different amounts of biotin added, the differences were fairly small.

Experimental

Avidin Targeting Assay (Displacement of HABA) 12 disposable cuvettes were filled as shown in Table 32 (before biotin and enzyme addition measurement of $A_{500}$):

TABLE 32

Avidin targeting assay

| Cuvette Number | Buffer[a]/ μL | HABA/ Avidin[b]/ μL | d-Biotin/ μL (conc. [mg/mL]) | Enzyme/ μL (conc. [mg/mL]) |
|---|---|---|---|---|
| 1 | 400 | 400 | — | —[c] |
| 2 | 400 | 400 | — | —[c] |
| 3 | 400 | 400 | — | —[c] |
| 4 | 390 | 400 | 10 (0.060)[d] | —[c] |
| 5 | 400 | 400 | — | 200 of S156C-S-Biotin (0.329) |
| 6 | 400 | 400 | — | 200 of S166C-S-Biotin (0.534) |
| 7 | 400 | 400 | — | 200 of N62C-S-Biotin (0.260) |
| 8 | 400 | 400 | — | 200 of L217C-S-Biotin (0.359) |
| 9 | 400 | 400 | — | 200 of WT (0.143)[e] |
| 10 | 390 | 400 | 10 (0.060)[d] | 200 of WT (0.143)[e] |
| 11 | 390 | 400 | 10 (0.097)[f] | 200 of WT (0.143)[e] |
| 12 | 390 | 400 | 10 (0.047)[g] | 200 of WT (0.143)[e] |
| 13 | 390 | 400 | 10 (0.065)[h] | 200 of WT (0.143)[e] |
| 14 | 390 | 400 | 10 (0.649)[i] | 200 of WT (0.143)[e] |

[a]Assay Buffer: 20 mM Tris•HCl, 2 mM $CaCl_2$, pH 8.6.
[b]HABA/avidin reagent (Sigma) prepared with 10 mL of Milli-Q water.
[c]200 μL of MES buffer (10 mM MES, 1 mM $CaCl_2$, pH 5.8).
[d]Solution of d-biotin (Sigma) diluted to the same concentration (in 10 μL) as in 200 μL of active S156C-S-Biotin (0.329 mg/mL) in Assay Buffer.
[e]Solution of lyophilized GG36-WT in 10 mM MES, 1 mM $CaCl_2$, pH 5.8 (PMSF corrected).
[f]Solution of d-biotin (Sigma) diluted to the same concentration (in 10 μL) as in 200 μL of active S166C-S-Biotin (0.534 mg/mL) in Assay Buffer.
[g]Solution of d-biotin (Sigma) diluted to the same concentration (in 10 μL) as in 200 μL of active N62C-S-Biotin (0.260 mg/mL) in Assay Buffer.
[h]Solution of d-biotin (Sigma) diluted to the same concentration (in 10 μL) as in 200 μL of active L217C-S-Biotin (0.359 mg/mL) in Assay Buffer.
[i]Solution of d-biotin (Sigma) diluted to the same concentration (in 10 μL) as for protein amount of 200 μL of S156C-S-Biotin (as determined by lyophilization) in Assay Buffer.

Before addition of biotin and enzyme the cuvette was equilibrated in the spectrophotometer until $A_{500}$ stabilized (5-10 min). Biotin and enzyme, respectively, were added and $A_{500}$ was measured over a period of 5 min. Table 33 shows the assay results:

TABLE 33

Results of assay.

| Cuvette Number | HABA/ Avidin Before[a]/ Abs | HABA/ Avidin After[b]/ Abs | HABA/ Avidin Diff.[b]/ Abs | HABA Release/ Abs[b,c] | % of Max HABA Release[b]/ Abs |
|---|---|---|---|---|---|
| 1 | 0.535 | 0.382 | 0.153 | — | — |
| 2 | 0.487 | 0.344 | 0.143 | — | — |
| 3 | 0.482 | 0.353 | 0.129 | — | — |
| 4 | 0.563 | 0.304 | 0.259 | 0.117 | 40 |
| 5 | 0.545 | 0.121 | 0.424 | 0.282 | 95 |
| 6 | 0.547 | 0.267 | 0.280 | 0.138 | 47 |
| 7 | 0.545 | 0.347 | 0.198 | 0.056 | 19 |
| 8 | 0.545 | 0.331 | 0.214 | 0.072 | 24 |
| 9 | 0.493 | 0.349 | 0.144 | 0.002 | 1 |
| 10 | 0.513 | 0.272 | 0.242 | 0.100 | 34 |
| 11 | 0.522 | 0.218 | 0.304 | 0.162 | 55 |
| 12 | 0.513 | 0.289 | 0.224 | 0.082 | 28 |
| 13 | 0.501 | 0.255 | 0.246 | 0.104 | 35 |
| 14 | 0.522 | 0.084 | 0.438 | 0.296 | 100 |

[a]Mixture of HABA/avidin and buffer before addition of enzyme (and biotin).
[b]Value 5 min after addition of enzyme (and biotin).
[c]Calculated from difference between HABA/Avidin drop in Abs. for sample and the drop in Abs. caused by dilution alone (controls).

Avidin Hydrolysis Assay (Via $A_{280}$ Measurement)—Measured for S156C-Biotin Only Twenty, disposable eppendorf vials were filled as shown in Table 34.

TABLE 34

Avidin hydrolysis assay.

| Vial Number | Buffer[a]/ μL | Avidin[b]/ μL | Decoy Protein[c]/ μL | Biotin/ μL | Enzyme/ μL |
|---|---|---|---|---|---|
| 1 | 700 | 100 | — | — | —[d] |
| 2 | 600 | 100 | 100 | — | —[d] |
| 3 | 700 | 100 | — | — | 200 of WT[e] |
| 4 | 700 | 100 | — | — | 200 of WT[e] |
| 5 | 600 | 100 | 100 | — | 200 of WT[e] |
| 6 | 600 | 100 | 100 | — | 200 of WT[e] |
| 7 | 690 | 100 | — | 10[f] | 200 of WT[e] |
| 8 | 690 | 100 | — | 10[f] | 200 of WT[e] |
| 9 | 590 | 100 | 100 | 10[f] | 200 of WT[e] |
| 10 | 590 | 100 | 100 | 10[f] | 200 of WT[e] |
| 11 | 690 | 100 | — | 10[g] | 200 of WT[e] |
| 12 | 690 | 100 | — | 10[g] | 200 of WT[e] |
| 13 | 590 | 100 | 100 | 10[g] | 200 of WT[e] |
| 14 | 590 | 100 | 100 | 10[g] | 200 of WT[e] |
| 15 | 700 | 100 | — | — | 200 of S156CMM |
| 16 | 700 | 100 | — | — | 200 of S156CMM |
| 17 | 600 | 100 | 100 | — | 200 of S156CMM |
| 18 | 600 | 100 | 100 | — | 200 of S156CMM |
| 19 | 400 | 100 | 300 | — | 200 of S156CMM |
| 20 | 400 | 100 | 300 | — | 200 of S156CMM |

[a] Assay Buffer: 20 mM Tris•HCl, 2 mM CaCl$_2$, pH 8.6.
[b] 5 mg/mL solution of avidin (Sigma) in Milli-Q water.
[c] 0.5 mg/mL solution of Ribonuclease A with Scrambled Bisulfide Bonds (Sigma) in Milli-Q water.
[d] 200 μL of MES buffer (10 mM MES, 1 mM CaCl$_2$, pH 5.8).
[e] Solution of lyophilized GG36-WT diluted to the same catalytic activity as the biotin-CMM (as determined by initial rate kinetics with sAAPFpNA) in 10 mM MES, 1 mM CaCl$_2$, pH 5.8.
[f] Solution of d-biotin (Sigma) diluted to the same concentration (in 10 μL) as in 200 μL of active S156C-S-Biotin (0.329 mg/mL) in Assay Buffer.
[g] Solution of d-biotin (Sigma) diluted to the same concentration (in 10 μL) as for protein amount of 200 μL of S156C-S-Biotin (as determined by lyophilization) in Assay Buffer.

These solutions were incubated at 35° C. in a thermostat-controlled water bath for the indicated time. The contents of the appropriate vials were then each placed in the top of a Centricon-SR3 Concentrator (Amicon, MWCO 3000, previously cleaned by 2 mL of Milli-Q water centrifuged at 3750 rpm for 90 min) and centrifuged at 3750 rpm for 60 min. The resulting filtrates were then assayed as shown in Table 35.

TABLE 35

Assay. S156C-S-d-Biotin (0.329 mg/mL = 2.4 μM)

| Vial Number | Incub. Time/min | $A_{280}$[a] | Total Protein/ Abs | % of Max Total Protein/Abs |
|---|---|---|---|---|
| 1 | 60 | 0.002 | — | — |
| 2 | 60 | 0.014 | — | — |
| 3 | 60 | 0.013 | 0.005 | 4 |
| 4 | 240 | 0.028 | 0.020 | 17 |
| 5 | 60 | 0.040 | 0.032 | 27 |
| 6 | 240 | 0.059 | 0.051 | 44 |
| 7 | 60 | 0.015 | 0.007 | 6 |
| 8 | 240 | 0.030 | 0.022 | 19 |
| 9 | 60 | 0.043 | 0.035 | 30 |
| 10 | 240 | 0.059 | 0.051 | 44 |
| 11 | 60 | 0.013 | 0.005 | 4 |
| 12 | 240 | 0.029 | 0.021 | 18 |
| 13 | 60 | 0.035 | 0.027 | 23 |
| 14 | 240 | 0.046 | 0.038 | 32 |
| 15 | 60 | 0.054 | 0.046 | 39 |
| 16 | 240 | 0.081 | 0.073 | 62 |
| 17 | 60 | 0.058 | 0.050 | 43 |
| 18 | 240 | 0.080 | 0.072 | 62 |
| 19 | 60 | 0.103 | 0.095 | 81 |
| 20 | 240 | 0.125 | 0.117 | 100 |

[a] Value for 700 μL of Avidin Hydrolysis Assay filtrate diluted with 300 μL of Milli-Q as compared with Milli-Q water blank (1 mL).

Controls without Avidin

Assay performed as Avidin Hydrolysis Assay except 100 μL aliquots of avidin replaced by 100 μL of Milli-Q water; the measurement for S156C-S-Biotin and a higher decoy protein amount [0.15 mg, Decoy (2)] was not repeated as control without avidin (see Table 36).

TABLE 36

Control hydrolysis assay without avidin.

| Vial Number | Incub. Time/min | $A_{280}$[a] | Total Protein/ Abs | % of Max Total Protein-Abs |
|---|---|---|---|---|
| 1 | 60 | −0.001 | — | — |
| 2 | 60 | 0.018 | — | — |
| 3 | 60 | 0.000 | −0.008 | −7 |
| 4 | 240 | 0.009 | 0.001 | 0.9 |
| 5 | 60 | 0.020 | 0.012 | 10 |
| 6 | 240 | 0.035 | 0.027 | 23 |
| 7 | 60 | 0.003 | −0.005 | −4 |
| 8 | 240 | 0.010 | 0.002 | 2 |
| 9 | 60 | 0.024 | 0.016 | 14 |
| 10 | 240 | 0.029 | 0.021 | 18 |
| 11 | 60 | 0.001 | −0.007 | −6 |
| 12 | 240 | 0.012 | 0.004 | 3 |
| 13 | 60 | 0.026 | 0.018 | 15 |
| 14 | 240 | 0.029 | 0.021 | 18 |
| 15 | 60 | 0.028 | 0.020 | 17 |
| 16 | 240 | 0.024 | 0.016 | 14 |
| 17 | 60 | 0.039 | 0.031 | 26 |
| 18 | 240 | 0.052 | 0.044 | 38 |

[a] as above.

Avidin Hydrolysis Assay (Via $A_{280}$ Measurement) Using S166C-Biotin, L217C-Biotin and N62C-Biotin The Avidin Hydrolysis Assay was also performed for N62C-S-Biotin and S166C-S-Biotin in addition to S156C-S-Biotin reported earlier. For comparison, we report the results for the S156C CMM again.

S156C-S-Biotin produces 72% more protein fragments after 240 min than SBL-WT. In the presence of decoy protein [0.05 mg] the amount of total protein produced increases drastically for the WT enzyme (23% after 240 min) whereas the production of total protein does not change significantly for the biotin-CMM.

N62C-S-Biotin provides nearly the same amount of protein fragments as SBL-WT after 240 min. However, in the presence of a decoy the N62C CMM gives only 5% more protein release after 240 min and is therefore clearly more selective than SBL-WT (23% more protein fragments after 240 min). Those results suggests that the biotin side-chain of the N62C CMM is less available since overall protein hydrolysis is less effective by this CMM compared to S156C CMM which contains a surface exposed biotin moiety. However, since in the N62 CMM the biotin side-chain is adjacent to the catalytic center its avidin hydrolysis selectivity is nearly as effective as for S156C-S-Biotin.

The S166C CMM gives a 7% higher protein release compared to SBL-WT but is fairly unselective in the presence of a decoy protein [18% protein fragments compared to 23% for SBL-WT after 240 min]. Although this enzyme proved to be the second best of the biotin-CMMs in the "Avidin Targeting Assay", it is less selective than the N62C CMM with respect to the "Avidin Hydrolysis Assay". Presumably the biotin side chain buried in the $S_1$ pocket is available for avidin targeting but conformationally not very favorable for the effective and selective catalysis of avidin hydrolysis.

Experimental

Fourteen disposable eppendorf vials were filled as shown in Table 37.

TABLE 37

Setup for avidin hydrolysis assay.

| Vial Number | Buffer[a]/ μL | Avidin[b]/ μL | Decoy Protein[c]/ μL | Biotin/ μL | Enzyme/ μL |
|---|---|---|---|---|---|
| 1 | 700 | 100 | — | — | —[d] |
| 2 | 600 | 100 | 100 | — | —[d] |
| 3 | 700 | 100 | — | — | 200 of WT[e] |
| 4 | 700 | 100 | — | — | 200 of WT[e] |
| 5 | 600 | 100 | 100 | — | 200 of WT[e] |
| 6 | 600 | 100 | 100 | — | 200 of WT[e] |
| 7 | 700 | 100 | — | — | 200 of biotin-CMM[f] |
| 8 | 700 | 100 | — | — | 200 of biotin-CMM[f] |
| 9 | 600 | 100 | 100 | — | 200 of biotin-CMM[f] |
| 10 | 600 | 100 | 100 | — | 200 of biotin-CMM[f] |
| 11 | 690 | 100 | — | 10[g] | 200 of WT[e] |
| 12 | 690 | 100 | — | 10[g] | 200 of WT[e] |
| 13 | 590 | 100 | 100 | 10[g] | 200 of WT[e] |
| 14 | 590 | 100 | 100 | 10[g] | 200 of WT[e] |

[a]Assay Buffer: 20 mM Tris•HCl, 2 mM $CaCl_2$, pH 8.6.
[b]5 mg/mL solution of avidin (Sigma) in Milli-Q water.
[c]0.5 mg/mL solution of Ribonuclease A with Scrambled Disulfide Bonds (Sigma) in Milli-Q water.
[d]200 μL of MES buffer (10 mM MES, 1 mM $CaCl_2$, pH 5.8).
[e]Solution of lyophilized GG36-WT diluted to the same catalytic activity as the biotin-CMMs (as determined by initial rate kinetics with succ-AAPF-pNA) in 10 mM MES, 1 mM $CaCl_2$, pH 5.8 (concentrations of biotin-CMMs see[f]).
[f]S156C-S-Biotin (0.329 mg/mL), N62C-S-Biotin (0.260 mg/mL), S166C-S-Biotin (0.534 mg/mL); concentrations of biotin-CMMs calculated for same catalytic activity (as determined by initial rate kinetics with succ-AAPF-pNA); solutions in 10 mM MES, 1 mM $CaCl_2$, pH 5.8.
[g]Solution of d-biotin (Sigma) diluted to the same concentration (in 10 μL) as in 200 μL of active biotin-CMM (0.060 mg/mL biotin for S156C-S-Biotin, 0.047 mg/mL biotin for N62C-S-Biotin, 0.097 mg/mL biotin for S166C-S-Biotin) or as for protein amount of 200 μL of S156C-S-Biotin (as determined by lyophilization; 0.649 mg/mL biotin) in Assay Buffer.

These solutions were incubated at 35° C. in a thermostat-controlled water bath for the indicated time. The contents of the appropriate vials were then each placed in the top of a Centricon SR3 or Centricon YM-3 Concentrator (Amicon, MWCO 3000, previously cleaned with 2 mL of Milli-Q water centrifuged at 3750 rpm for 90 min) and centrifuged at 3750 rpm for 60 min. The resulting filtrates were then assayed and the results are shown in: Table 38, Table 39; Table 40, Table 41, and Table 42.

TABLE 38

Results for avidin hydrolysis assay for controls and WT

| Vial Number | Incub. Time/min | $A_{280}$[a] | Total Protein/ Abs | % of Max Total Protein/Abs |
|---|---|---|---|---|
| 1 | 60 | 0.004 | — | — |
| 2 | 60 | 0.013 | — | — |
| 3 | 60 | 0.023 | 0.014 | 19 |
| 4 | 240 | 0.029 | 0.020 | 28 |
| 5 | 60 | 0.035 | 0.026 | 36 |
| 6 | 240 | 0.046 | 0.037 | 51 |

[a]Value determined in triplicate for 700 μL of Avidin Hydrolysis Assay filtrate diluted with 300 μL of Milli-Q as compared with Milli-Q water blank (1 mL).

TABLE 39

Results of avidin hydrolysis assay for S156C-S-Biotin.

| Vial Number | Incub. Time/min | $A_{280}$[a] | Total Protein/ Abs | % of Max Total Protein/Abs |
|---|---|---|---|---|
| 7 | 60 | 0.054 | 0.045 | 62 |
| 8 | 240 | 0.081 | 0.072 | 100 |
| 9 | 60 | 0.058 | 0.049 | 68 |
| 10 | 240 | 0.080 | 0.071 | 99 |
| 9[b] | 60 | 0.103 | 0.094 | 131 |
| 10[b] | 240 | 0.125 | 0.116 | 161 |

[a]Value for 700 μL of Avidin Hydrolysis Assay filtrate diluted with 300 μL of Milli-Q as compared with Milli-Q water blank (1 mL).
[b]300 μL instead of 100 μL of decoy protein used.

TABLE 40

Results of avidin hydrolysis assay for N62C-S-Biotin.

| Vial Number | Incub. Time/min | $A_{280}$[a] | Total Protein/ Abs | % of Max Total Protein/Abs |
|---|---|---|---|---|
| 7 | 60 | 0.018 | 0.009 | 12 |
| 8 | 240 | 0.032 | 0.023 | 32 |
| 9 | 60 | 0.029 | 0.020 | 28 |
| 10 | 240 | 0.036 | 0.027 | 37 |

[a]As above.

TABLE 41

Results of avidin hydrolysis assay for S166C-S-Biotin

| Vial Number | Incub. Time/min | $A_{280}$[a] | Total Protein/ Abs | % of Max Total Protein/Abs |
|---|---|---|---|---|
| 7 | 60 | 0.026 | 0.017 | 24 |
| 8 | 240 | 0.034 | 0.025 | 35 |
| 9 | 60 | 0.033 | 0.024 | 33 |
| 10 | 240 | 0.047 | 0.038 | 53 |

[a]As above.

TABLE 42

Controls of avidin hydrolysis by SBL-WT with different amounts of biotin added

| Vial Number | Incub. Time/min | $A_{280}$[a] | Total Protein/ Abs | % of Max Total Protein/Abs |
|---|---|---|---|---|
| 11[b] | 60 | 0.015 | 0.006 | 8 |
| 12[b] | 240 | 0.030 | 0.021 | 29 |
| 13[b] | 60 | 0.045 | 0.036 | 50 |
| 14[b] | 240 | 0.051 | 0.042 | 58 |
| 11[c] | 60 | 0.014 | 0.005 | 7 |
| 12[c] | 240 | 0.026 | 0.017 | 24 |
| 13[c] | 60 | 0.030 | 0.021 | 29 |
| 14[c] | 240 | 0.039 | 0.030 | 42 |
| 11[d] | 60 | 0.021 | 0.012 | 17 |
| 12[d] | 240 | 0.032 | 0.023 | 32 |
| 13[d] | 60 | 0.036 | 0.027 | 37 |
| 14[d] | 240 | 0.047 | 0.038 | 53 |
| 11[e] | 60 | 0.013 | 0.004 | 5 |
| 12[e] | 240 | 0.029 | 0.020 | 28 |
| 13[e] | 60 | 0.035 | 0.026 | 36 |
| 14[e] | 240 | 0.046 | 0.037 | 51 |

[a]As above.
[b]Same biotin amount as in active S156C-S-Biotin.
[c]Same biotin amount as in active N62C-S-Biotin.
[d]Same biotin amount as in active S166C-S-Biotin.
[e]Same biotin amount as in S156C-S-Biotin calculated for whole protein amount (active and inactive enzyme).

Example 11

Targeting Antibodies using a Hapten Modified Subtilisin

As an extension of the targeted degradation of enzymes, we have now focused on hapten directed degradation of antibodies by SBL. This example demonstrates antibody targeting using an anti-biotin antibody/biotin system.

Preparation of Biotin-MTS and Biotinylated CMMs

In order to target anti-biotin with SBL, we have attached the biotin-MTS reagent to our mutant enzymes. The synthesis of the biotin-MTS was accomplished as outlined in Example 8. Each of the CMMs was prepared according to standard protocol, e.g., as described in Example 9. All CMMs were characterized using MALDI technique which has an method-dependent error in the magnitude of +0.2-0.5%. The results are shown in Table 43 and Table 44.

TABLE 43

MALDI-MS for biotinylated CMMs

| Enzyme | Calculated mass | Found | % error |
|---|---|---|---|
| N62C-Biotin | 26931 | 26943.7 | 0.04 |
| S156C-Biotin | 26958 | 26980.4 | 0.08 |
| S166C-Biotin | 26958 | 26977.5 | 0.07 |
| L217C-Biotin | 26932 | 26971.7 | 0.14 |

The amidase activities of the new biotinylated CMMs were determined and show the same trend as described above in Example 9. The results are shown in Table 36.

TABLE 44

Amidase Activity for Biotinylated CMMs

| | Amidase activity | | |
|---|---|---|---|
| Enzyme | $k_{cat}$ | $K_M$ | $k_{cat}/K_M$ |
| WT[a] | 153 | 0.73 | 209 |
| N62C-Biotin | 108.86 | 0.96 | 113.40 |
| S156C-Biotin | 59.46 | 0.78 | 76.46 |
| S166C-Biotin | 46.00 | 0.999 | 45.83 |
| L217C-Biotin | 55.35 | 1.07 | 51.73 |

Targeting Assay for Biotinylated CMMs to Anti-Biotin

Antibodies to biotin (anti-Biotin) are commercially available as either free antibody or as an enzyme-conjugate. We chose an anti-biotin conjugated to alkaline phosphatase as our model target antibody. Using the standard Enzyme Linked Immuno-sorbent Assay (ELISA)-technique, we could demonstrate the ability of our CMMs to target the antibody. The experiment is outlined schematically in FIG. 17.

Figure 17:
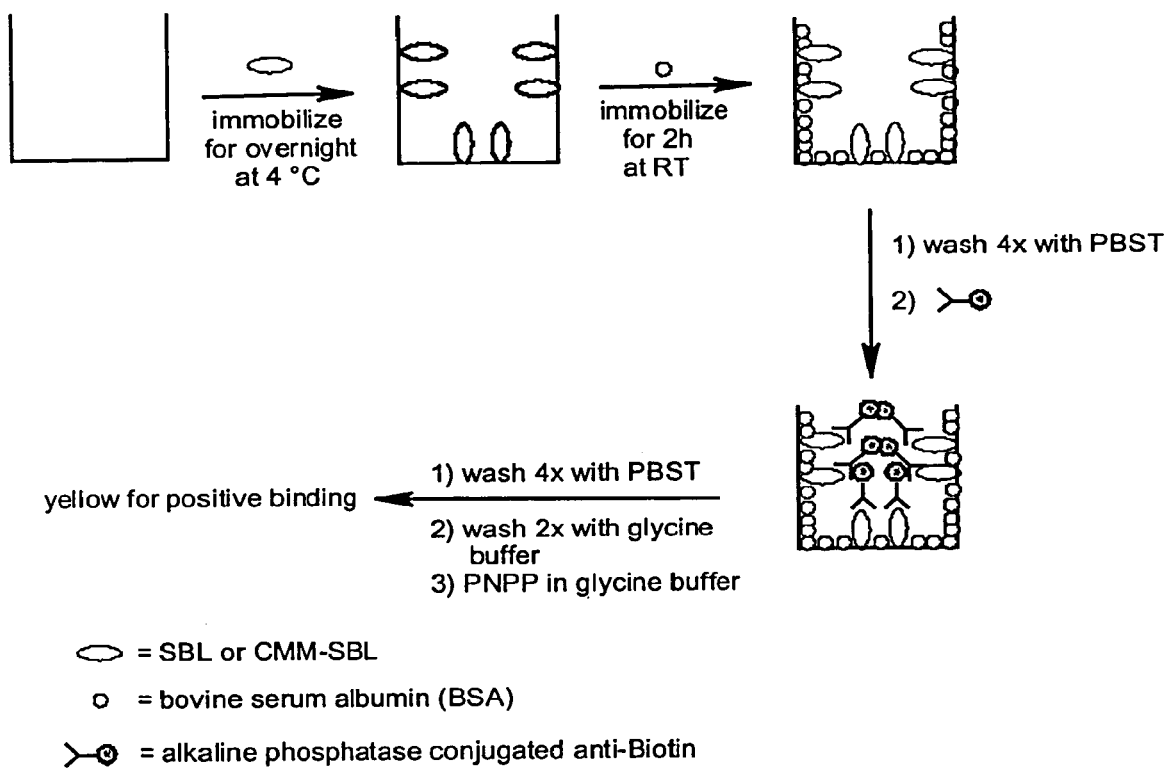
FIG. 17 illustrates a standard enzyme linked immunosorbent assay (ELISA)-technique for assaying targeting of biotinylated CMMs to anti-biotin.

Our first assay series was carried out using the ELISA-technique (FIG. 17) with polystyrene 96-well plates (Harlow and Lane (1988) Antibodies: A laboratory Manual: Cold Spring Habour Laboratory, USA, p. 564-597). The CMM was immobilized on the plate surface overnight at 4° C. [typical binding of protein to a polystyrene plate is approximately 100 ng/well (300 ng/cm²). In our case, we attached less protein as we did not fully fill each well with enzyme solution]. After blocking the remaining binding sites on the plate with BSA, unbound protein (loosely antibody and BSA) was washed out twice with phosphate-buffered saline containing Tween, pH 7.2 (PBST). (Tween was used in this buffer to prevent the unbound polystyrene surface from the attachment of antibody.) Then the anti-Biotin was added to each well and incubated at 4° C. for 2 h. The plate was washed with PBST (4 times) to remove the loosely, unbound protein, and then with glycine buffer pH 10.4 (2 times) to wash away the phosphate buffer and to optimize the pH for alkaline phosphatase activity. To assay the biotin-CMM/anti-biotin binding the enzyme activity of the antibody-linked alkaline phosphatase was used. The phosphatase substrate [a solution of p-nitrophenylphosphate disodium salt (PNPP) in glycine buffer pH 10.4] was added and the reaction was carried out at 4° C. The release of p-nitrophenolate was determined visually using a 96-well plate (FIG. 17).

From the 96-well results, we found that the amount of PNPP substrate is very important for demonstrating the differences of the targeting abilities of our biotin-CMMs to anti-biotin. Using a high amount of substrate we were unable to distinguish between different CMMs, as all gave a bright yellow colour within 30 min. However, we were still able to discern the location of the S156C-biotin on the plate since the color change was extremely rapid in this case.

We also carried out a control reaction, using PMSF as an inhibitor for WT- and CMM-SBL (as SBL might hydrolyze anti-biotin leading to a negative result). No difference between the reactions with and without PMSF could be found. Therefore we excluded this reagent from our following experiments.

Using the same protocol and conditions as for the 96-well plate experiments, later experiments were carried out in polystyrene cuvettes and the absorption ($A_{405}$) of released p-nitrophenolate from PNPP (150 μL in 1 mL) was monitored spectrometrically (Table 45). Because of the high dilution of PNPP used, the reaction had to be monitored for a long time. It should be noted that the results of the assay using cuvettes are not always as consistent as those from 96-well plates. This was probably due to the fact that 96-well plates have been developed for protein attachment. The assay results are shown in Table 37.

TABLE 45

$A_{405}$ assay (p-nitrophenolate release, low PNPP concentration)

| | $A_{405}$ | | | | |
|---|---|---|---|---|---|
| time (h) | WT | N62C-Biotin | S156C-Biotin | S166C-Biotin | L217C-Biotin |
| 18 | 0.145 | 1.018 | 1.111 | 0.483 | 0.292 |
| 24 | 0.173 | 1.191 | 1.322 | 0.569 | 0.348 |
| 27 | 0.222 | 1.522 | 1.689 | 0.736 | 0.451 |
| 30 | 0.259 | 1.739 | 1.915 | 1.065 | 0.526 |

All CMMs caused a higher release of p-nitrophenolate as compared to WT. S156C-biotin was found to induce the greatest p-nitrophenolate release (up to 86.5% more than WT after 30 h), showing it to be the most proficient CMM for Anti-biotin IgG targeting.

Further experiments suggested that the concentration of PNPP can be increased (300 μL in 1 mL) to shorten the observation time. The trend of the p-nitrophenolate release is the same as in the low PNPP concentration assay. The results are shown in Table 46.

TABLE 46

A_405 Assay (p-Nitrophenolate Release, high PNPP concentration)

| | | | $A_{405}$ | | |
|---|---|---|---|---|---|
| time (h) | WT | N62C-Biotin | S156C-Biotin | S166C-Biotin | L217C-Biotin |
| 6 | 0.214 | 0.667 | 1.040 | 0.647 | 0.483 |
| 12 | 0.398 | 0.969 | 1.400 | 0.908 | 0.577 |

All biotinylated CMMs gave an increased p-nitrophenolate release compared to WT. Therefore binding of the biotin-CMMs to anti-biotin must have been occurred. The assay results (Tables 37 and 38) clearly demonstrate the ability of our biotinylated CMMs to target a biotin-antibody.

"Hydrolysis" Assay of Anti-Biotin by Biotinylated CMMs

Next, we were interested in demonstrating the ability of our CMMs to hydrolyze the anti-biotin selectively. We adopted the approach used successfully to monitor the release of protein fragments during SBL-mediated avidin hydrolysis. It should be noted that equal concentrations of active enzymes (as determined by PMSF titration) were used in these experiments. The enzymes and anti-biotin IgG were incubated in Tris buffer (20 mM Tris.HCl, 2 mM $CaCl_2$, pH 8.6) at 35° C. for 60 and 240 min. The protein fragments were separated from the crude hydrolysate using size exclusion-membranes as reported previously. Measurement of the absorption at 280 nm afforded the concentration of the released protein fragments. The results are shown in Table 47.

TABLE 47

Anti-biotin hydrolysis assay ($A_{280}$).

| Enzyme | $A_{280}$ (60 min) | $A_{280}$ (240 min) |
|---|---|---|
| anti-Biotin + Tris (blank) | 0.004 | 0.008 |
| WT | 0.086 | 0.087 |
| N62C-Biotin | 0.102 | 0.112 |
| S156C-Biotin | 0.140 | 0.177 |
| S166C-Biotin | 0.115 | 0.127 |
| L217C-Biotin | 0.069 | 0.125 |

The results, except for one (L217C-Biotin), demonstrate clearly that our CMMs are able to hydrolyze anti-Biotin better than WT. These results also correspond to the targeting results ($A_{405}$ assay for p-nitrophenolate release) which show that all biotinylated CMMs target anti-biotin and therefore give a higher p-nitrophenolate release than WT.

To determine whether or not the hydrolysis was specifically towards anti-biotin, we adopted the biotin assay experiment again which uses RNAase as a decoy protein. The results for each CMM hydrolysis compared to WT are shown in Table 48, Table 49, Table 50, and Table 51.

TABLE 48

Assay ($A_{280}$) for selective hydrolysis of anti-biotin by biotin-CMM N62C-biotin and by WT[a]

| | | $A_{280}$ | | | | |
|---|---|---|---|---|---|---|
| time (min) | WT | WT + decoy | difference | N62C-Biotin | N62C-Biotin + decoy | difference |
| 60 | 0.040 | 0.148 | 0.108 | 0.045 | 0.068 | 0.023 |
| 240 | 0.040 | 0.148 | 0.108 | 0.052 | 0.075 | 0.023 |

TABLE 49

Assay ($A_{280}$) for selective hydrolysis of anti-biotin by biotin-CMM S156C-biotin and by WT[a]

| | | $A_{280}$ | | | | |
|---|---|---|---|---|---|---|
| time (min) | WT | WT + decoy | difference | S156C-Biotin | S156C-Biotin + decoy | difference |
| 60 | 0.040 | 0.148 | 0.108 | 0.110 | 0.112 | 0.002 |
| 240 | 0.040 | 0.148 | 0.108 | 0.134 | 0.148 | 0.014 |

TABLE 50

Assay ($A_{280}$) for selective hydrolysis of anti-biotin by biotin-CMM S166C-biotin and by WT[a]

| | | $A_{280}$ | | | | |
|---|---|---|---|---|---|---|
| time (min) | WT | WT + decoy | difference | S166C-Biotin | S166C-Biotin + decoy | difference |
| 60 | 0.040 | 0.148 | 0.108 | 0.074 | 0.085 | 0.011 |
| 240 | 0.040 | 0.148 | 0.108 | 0.087 | 0.090 | 0.003 |

TABLE 51

Assay ($A_{280}$) for selective hydrolysis of anti-biotin by biotin-CMM L217C-biotin and by WT[a]

| | | $A_{280}$ | | | | |
|---|---|---|---|---|---|---|
| time (min) | WT | WT + decoy | difference | L217C-Biotin | L217C-Biotin + decoy | difference |
| 60 | 0.040 | 0.148 | 0.108 | 0.037 | 0.060 | 0.023 |
| 240 | 0.040 | 0.148 | 0.108 | 0.053 | 0.065 | 0.012 |

[a]The numbers in the table are corrected with $A_{280}$ of the background reaction.

The experiments reveal that the differences in extend of hydrolysis between the reactions carried out in the presence and absence of decoy protein for CMMs catalyzed reactions are much smaller than for WT catalyzed reactions. Hence, as expected, our biotinylated CMMs hydrolyze anti-biotin more specifically than WT. Control experiments were carried out without anti-biotin (only SBL-CMM and RNAase) as well as with SBL-CMM and Tris buffer alone (without RNAase and anti-Biotin). The background absorption was insignificant in all cases.

Experimental 5-([3aS-(3aα,4β,6aα)]-Hexahydro-2-oxo-1H-thieno[3,4-d]imidazol-4-yl)pentyl methanethiosulfonate [(+)-Biotin-MTS]

The Biotin-MTS was prepared according to the procedure described in Example 8.

Materials

Phosphate buffered saline (PBS) solution was prepared from 8 g NaCl, 0.2 g KCl, 1.44 g $Na_2HPO_4$, 0.24 g $KH_2PO_4$ in 1 L water, adjust pH to 7.2 with 1N HCl and was stored at room temperature. 10% Sodium azide solution was prepared from 10 g $NaN_3$ in 100 mL water and was stored at room temperature. 3% BSA in PBS solution was prepared from 3 g bovine serum albumin (fraction V) in 100 mL water, then 0.2 mL 10% $NaN_3$ solution added and was stored at 4° C. Phosphate buffered saline with Tween (PBST) solution was prepared from 0.5 mL of Tween 80 in 1 L PBS solution. Anti-biotin solution (1:30,000) solution was prepared from 16.67

μL anti-biotin (Sigma A-6561 clone BN-34, conc. 1.15 mg/mL) in 50 mL 3% BSA/PBS and was stored at 4° C. 0.1 M glycine buffer pH 10.4 solution was prepared from 7.51 g glycine, 203 mg MgCl$_2$H$_2$O, 136 mg ZnCl$_2$ in 1 L water. The pH was adjusted to pH 10.4 with 10 N NaOH. p-Nitrophenylphosphate 1 mg/mL solution was prepared from 1 tablet PNPP (Sigma N-2765) (20 mg) in 20 mL of 0.1 M glycine buffer and was stored at 4° C. 0.06 M PMSF solution was prepared from 47.2 mg α-toluenesulfonyl fluoride (PMSF) in 449.2 μL EtOH and was stored at 0° C. The following enzymes were used: WT (1 mg/mL), N62C-Biotin (0.97 mg/mL), S156C-Biotin (0.71 mg/mL), S166C-Biotin (1.09 mg/mL) and L217C-Biotin (1.0 mg/mL). All enzymes were dissolved in MES buffer (20 mM MES, 1 mM CaCl$_2$, pH 5.8). 0.1 M Tris Buffer pH 8.6 consisted of 1.21 mg Tris in 100 mL water. The pH was adjusted to pH 8.6 with conc. HCl. Ribonuclease A, 5 mg/mL consisted of 5 mg of ribonuclease A (with scrambled disulfide bonds, Sigma R-2638) in 1 mL water.

Targeting Assay of CMM-SBL to Anti-Biotin using Polystyrene 96-Well Plate

Figure 18:
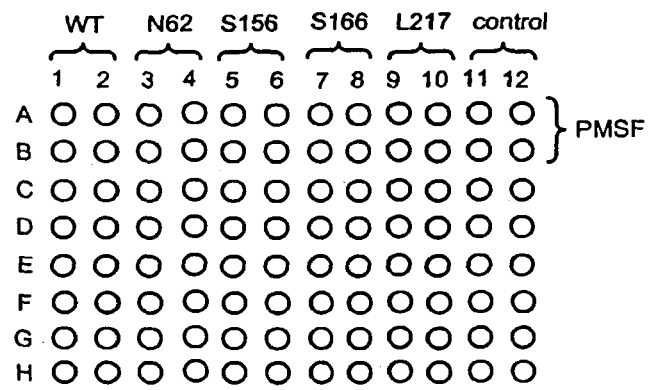
FIG. 18 illustrates a targeting assay for anti-biotin using hapten modified subtilisins in a 96-well plate.
Figure 19:
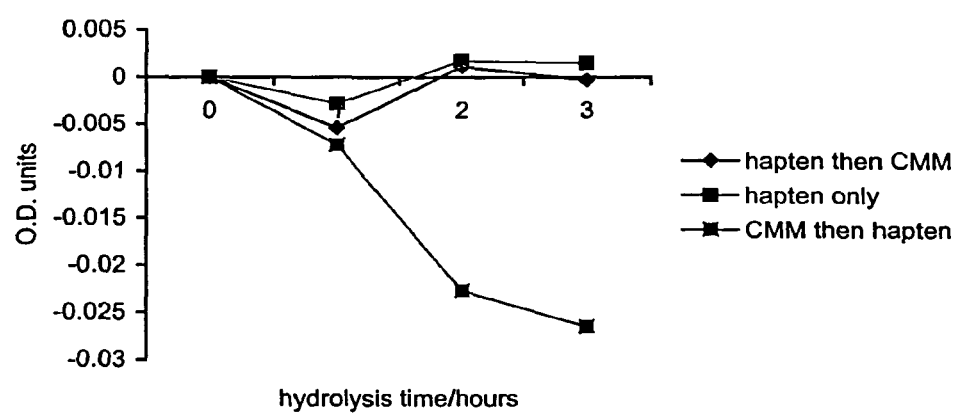
FIG. 19 plot of anti-biotin degradation by biotin-CMM as a function of time.

50 μL of each enzyme solution was added to each well of a polystyrene 96-well plate as shown in FIG. 18. All reactions were conducted twice to verity the reproducibility of the results.

The plate was incubated at 4° C. overnight. The remaining enzyme solutions were removed using a pipette. Then, BSA/PBS (3%, 100 μL) was added to each well and the plate was incubated at RT for 1 h. The BSA solution was removed and the plate was dried by flicking and banging it on layers of paper towel. PMSF (10 μL) was added to columns 1, 3, 5, 7, 9, 11 row A and B. After this procedure the plate was washed with PBST (2×) and dried as described previously. Anti-Biotin solution (30 μL) was added to each well, except for 1, 3, 5, 7, 9, 11 C and D, and the plate was kept for 2 h at 4° C. to minimize the proteolysis of antibody by the enzymes. The anti-Biotin solution was removed, the plate was washed with PBST (4×) to remove unbound antibody, and was dried in order to remove unbound antibody. The phosphate buffer was removed and the pH was adjusted for alkaline phosphatase activity by washing the plate with glycine buffer (0.1 M, pH 10.4) (2×) and drying afterwards. Then, glycine buffer and PNPP solution were added to the wells in the following manner:
1. Column 1, 3, 5, 7, 9, 11 row A and B (already treated with 10 μL PMSF solution) were filled with 40 μL 1 mg/mL PNPP.
2. Column 2, 4, 6, 8, 10, 12 row A and B were filled with 50 μL 1 mg/mL PNPP.
3. Column 2, 4, 6, 8, 10, 12 row C and D were filled with 25 μL 1 mg/mL PNPP+25 μL glycine buffer.
4. Column 2, 4, 6, 8, 10, 12 row E and F were filled with 12.5 μL 1 mg/mL PNPP+37.5 μL glycine buffer.
5. Column 2, 4, 6, 8, 10, 12 row G and H were filled with 6 μL 1 mg/mL PNPP+44 μL glycine buffer.
6. Column 1, 3, 5, 7, 9, 11 row C and D were filled with 50 μL 1 mg/mL PNPP.

The assay results can be summarized as follows:
The reactions in columns 1, 2 and 3 turned yellow in color almost instantly for all enzymes. After 15 min, the reactions in 4 for S156C-Biotin started to visibly change their color to pale yellow. S166C- started changing color after 20 min. N62C- started changing color after 1 h. After 1.5 h, there was no color change for WT and L217C-. The reactions in 6 for S156C- gave a color change after 2 h. All the reactions had strong yellow color after incubation overnight at 4° C.

Targeting Assay of CMM-SBL to Anti-Biotin using Polystyrene Cuvettes

The immobilization of the enzymes and anti-biotin and the washing processes for the cuvettes were conducted in the manner similar to that described for the 96-well plate. Two different concentrations of PNPP were used. The experiments were carried out in duplicate and the data shown in Table 52 below are the average results:

TABLE 52

Targeting assay in polystyrene cuvettes

| Enzyme | PNPP μL | Glycine Buffer μL | $A_{405}{}^a$ time (h) | | | | | |
|---|---|---|---|---|---|---|---|---|
| | | | 6 | 12 | 18 | 24 | 27 | 30 |
| WT | 150 | 850 | — | — | 0.145 | 0.173 | 0.222 | 0.259 |
| N62C- | 150 | 850 | — | — | 1.108 | 1.191 | 1.522 | 1.739 |
| S156C- | 150 | 850 | — | — | 1.111 | 1.322 | 1.689 | 1.915 |
| S166C- | 150 | 850 | — | — | 0.483 | 0.569 | 0.736 | 1.065 |
| L217C- | 150 | 850 | — | — | 0.292 | 0.348 | 0.451 | 0.526 |
| WT | 300 | 700 | 0.214 | 0.398 | — | — | — | — |
| N62C- | 300 | 700 | 0.667 | 0.969 | — | — | — | — |
| S156C- | 300 | 700 | 1.040 | 1.400 | — | — | — | — |
| S166C- | 300 | 700 | 0.647 | 0.908 | — | — | — | — |
| L217C- | 300 | 700 | 0.483 | 0.577 | — | — | — | — |

$^a$Glycine buffer was used to autozero the background absorption.

"Hydrolysis Assay" of Anti-Biotin with Biotin-CMMs and WT

Eppendorf vials were filled according to Table 43. The vials were then incubated at 35° C. in a thermostat-controlled water bath for 60 and 240 min. The contents of each vial were then placed in the top of a Centricon YM-3 filter (Amicon, MWCO 3000, pre-rinsed with 2 mL Milli-Q water centrifuged at 3750 rpm for 90 min) and centrifuged at 3750 rpm for 60 min. The filtrates were then assayed by measuring $A_{280}$ (zeroed against with Milli-Q water). The results are as shown in Table 53.

TABLE 53

Hydrolysis assay of anti-niotin with niotin-CMMs and WT

| Enzyme$^a$ | Anti-Biotin μL | Tris Buffer μL | RNAase μL | $A_{280}{}^b$ time (min) | |
|---|---|---|---|---|---|
| | | | | 60 | 240 |
| — | 50 | 940 | — | 0.004 | 0.008 |
| — | 50 | 930 | 10 | 0.005 | 0.007 |
| WT | — | 990 | — | 0.046 | 0.050 |
| N62C- | — | 990 | — | 0.057 | 0.060 |
| S156C- | — | 990 | — | 0.028 | 0.029 |
| S166C- | — | 990 | — | 0.041 | 0.040 |
| L217C- | — | 990 | — | 0.072 | 0.072 |
| WT | — | 980 | 10 | 0.025 | 0.036 |
| N62C- | — | 980 | 10 | 0.055 | 0.060 |
| S156C- | — | 980 | 10 | 0.045 | 0.054 |
| S166C- | — | 980 | 10 | 0.040 | 0.045 |
| L217C- | — | 980 | 10 | 0.051 | 0.059 |
| WT | 50 | 940 | — | 0.086 | 0.087 |
| N62C- | 50 | 940 | — | 0.102 | 0.112 |
| S156C- | 50 | 940 | — | 0.140 | 0.117 |
| S166C- | 50 | 940 | — | 0.115 | 0.177 |
| L217C- | 50 | 940 | — | 0.069 | 0.125 |
| WT | 50 | 930 | 10 | 0.173 | 0..184 |
| N62C- | 50 | 930 | 10 | 0.123 | 0.135 |
| S156C- | 50 | 930 | 10 | 0.155 | 0.188 |

TABLE 53-continued

Hydrolysis assay of anti-niotin with niotin-CMMs and WT

| Enzyme[a] | Anti-Biotin µL | Tris Buffer µL | RNAase µL | $A_{280}$[b] time (min) 60 | 240 |
|---|---|---|---|---|---|
| S166C- | 50 | 930 | 10 | 0.125 | 0.135 |
| L217C- | 50 | 930 | 10 | 0.114 | 0.124 |

[a]1 mg of active enzyme was used for each experiment (WT = 11.5 µL, N62C- = 11.8 µL, S156C- = 16.2 µL, S166C- = 10.6 µL, L217C- = 11.5 µL). The concentration of each enzyme as determined by PMSF titration is described in the *Materials Section*.
[b]The data show the actual absorption (data are corrected by subtracting the actual absorption from the corresponding background absorption).

Example 12

Assay for Residual Binding Capabilities of Anti-Biotin after Exposure to Biotinyl-CMMs Anti-Biotin Degradation The ability of S156C-biotin to destroy anti-biotin IgG was examined using micro-partition experiments. Two control experiments were also performed to validate the data.

Aliquots of an antibody-CMM (1:1, molecule:molecule) mixture were periodically withdrawn from an incubated vial (pH 8.6, 35° C.), and biotin solution was added to the aliquot. It was anticipated that only one CMM molecule would bind to each antibody molecule, as the steric bulk of the CMM would block the approach of a second CMM molecule to the other available binding site of the antibody. However, molecular biotin should be sufficiently small to allow it to bind to the second antibody binding site. As the antibody binding sites are degraded, fewer binding sites will be available resulting in more unbound biotin. Using a 3000 MWCO membrane, unbound biotin was separated from the macromolecules, and the biotin concentration was assayed using the HABA/avidin system.

Additionally, control experiments were performed containing biotin (hapten) only. Experiments where the antibody had been pre-incubated with biotin (hapten) before addition of the CMM were also studied. Reduction in the observed value of $A_{500}$ corresponds to diminution of the antibody's binding ability (FIG. 19).

Assay to prove Destruction of Anti-Biotin Binding Sites

Experimental

Monoclonal anti-biotin IgG (clone BN-34, Sigma, immunoglobulin concentration 1.3 mg/mL) conjugated to alkaline phosphatase was used for all studies. The TRIS buffer employed for these studies was the standard buffer employed for our amidase kinetic studies (0.1 M, pH 8.6, 0.005% Tween).

A solution of biotin (1.94 mg/mL) in TRIS (pH 8.6) was prepared. 10 μL of this solution was added to 779.5 μL of TRIS (this solution will be referred to as B/79 throughout). An Eppendorf vial containing TRIS (700.5 μL) and anti-biotin (37.5 μL, 1.3 mg/mL immunoglobulin, alkaline phosphatase labelled) was prepared. S156C-biotin (12.15 μL, 0.71 mg/mL) was added to the vial. The vial was vortexed, and was placed in a water bath (35° C.). Aliquots (170 μL) were periodically withdrawn from the vial, B/79 (20 μL) was added to each aliquot, and the mixture was then transferred to a pre-rinsed Centricon filter. The filters were centrifuged (2×1 h, 3750 rpm, 4° C.), and the filtrate was collected. The filtrate was assayed for biotin content using the HABA/avidin system: 70 μL of the filtrate was added to 70 μL of HABA/avidin reagent, and the $A_{500}$ reading of the mixture was observed using a 130 μL cuvette. The results are tabulated below in Table 54.

TABLE 54

| $A_{500}$ results from anti-biotin binding site degradation assay. | |
|---|---|
| Incubation time/h | $A_{500}$ CMM then hapten |
| 0 | 0.3172 |
| 1 | 0.31 |
| 2 | 0.2945 |
| 3 | 0.2907 |

Control Experiments

A solution of biotin (1.94 mg/mL) in TRIS (pH 8.6) was prepared. The solution was diluted twenty-fold (referred to throughout as B/20). Eppendorf vials were filled according to Table 55, and incubated for varying times at 35° C.

TABLE 55

| Volumes used for control experiments (each prepared in quadruplicate) | | | | |
|---|---|---|---|---|
| | Contents of each vial for each time point | | | |
| Experiment | TRIS (μL) | anti-biotin (μL) | S156C-biotin (μL) | B/20 (μL) |
| Ab then B/20. Incubate | 693 | 37.5 | 0 | 20 |
| Ab then B/20, then CMM. Incubate | 681 | 37.5 | 12.15 | 20 |

After incubation, the contents of each vial were transferred to a pre-rinsed Centricon filter (MWCO 3000), and the filters were centrifuged. The filtrates were assayed spectrophotometrically using the HABA/avidin reagent: 500 μL of filtrate was added to 500 μL of HABA/avidin reagent, and the $A_{500}$ value was determined using a 1 mL cuvette. The results are shown in Table 56.

TABLE 56

| $A_{500}$ results for control experiments | | |
|---|---|---|
| Incubation time/h | hapten then CMM | hapten only |
| 0 | 0.252 | 0.2687 |
| 1 | 0.2466 | 0.2659 |
| 2 | 0.2531 | 0.2704 |
| 3 | 0.2517 | 0.2702 |

Example 13

Stoichiometry of the Targeted Degradation Examples Above

In various experiments the following catalytic antagonists were found to function substoichoimetrically: Pyrazole CMM-HLADH (Example 2), pyrazole CMM-HLADH in the presence of AP (Example 3), substoichiometric pyrazole CMM-HLADH (Example 4), sugar CMM-biotinylated Con A (Examples 7 and 8), biotin CMM-Avidin, and biotin CMM-anti-biotin IgG.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of degrading a target molecule, said method comprising contacting said target molecule with a catalytic antagonist comprising a carbohydrate targeting moiety attached to a subtilisin-type serine protease, wherein said targeting moiety specifically binds to said target molecule and said protease degrades said target molecule, resulting in the release of said antagonist, thereby allowing said antagonist to bind and degrade another target molecule.

2. The method of claim 1, wherein said targeting moiety is joined to said serine protease through the sulfur group on a cysteine.

3. The method of claim 2, wherein said cysteine is a cysteine that is introduced into said serine protease by substituting a native amino acid other than cysteine with said cysteine.

4. The method of claim 3, wherein said cysteine is a cysteine that is substituted for a native amino acid other than cysteine in or near a subsite comprising a substrate binding site of said serine protease.

5. The method of claim 4, wherein said cysteine is a subsite selected from the group consisting of an S1 subsite, an S1' subsite, and an S2 subsite.

6. The method of claim 5, wherein said serine protease is a *Bacillus lentos* subtilisin.

7. The method of claim 5, wherein said cysteine is substituted for an amino acid corresponding to a reference residue in a *Bacillus lentos* subtilisin, where said reference residue is at a residue selected from the group consisting of residue 156, residue 166, residue 217, residue 222, residue 62, residue 96, residue 104, residue 107, residue 189, and residue 209.

8. The method of claim 1, wherein said target is a molecule present on the surface of a cell.

9. The method of claim 8, wherein said molecule present on the surface of a cell is a molecule forming a receptor.

10. The method of claim 8, wherein said molecule present on the surface of a cell is a ligand.

11. The method of claim 8, wherein said molecule present on the surface of a cell is component of a cell wall.

12. The method of claim 8, wherein said molecule present on the surface of a cell is component of a cell membrane.

13. The method of claim 1, wherein said targeting moiety is -thioethyl D-mannopyranoside.

* * * * *